US011098088B2

(12) United States Patent
Lightfoot et al.

(10) Patent No.: US 11,098,088 B2
(45) Date of Patent: Aug. 24, 2021

(54) ***LACTOBACILLUS ACIDOPHILUS* SURFACE LAYER PROTEIN A (SLPA) AS A THERAPEUTIC AGENT FOR THE TREATMENT OF INFLAMMATORY DISEASES**

(71) Applicant: UNIVERSITY OF FLORIDA RESEARCH FOUNDATION, INCORPORATED, Gainesville, FL (US)

(72) Inventors: Yaima L. Lightfoot, Washington, DC (US); Bikash Sahay, Gainesville, FL (US); Mansour Mohamadzadeh, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 16/790,793

(22) Filed: Feb. 14, 2020

(65) Prior Publication Data

US 2020/0172582 A1 Jun. 4, 2020

Related U.S. Application Data

(62) Division of application No. 15/521,418, filed as application No. PCT/US2015/055620 on Oct. 15, 2015, now Pat. No. 10,562,943.

(60) Provisional application No. 62/068,338, filed on Oct. 24, 2014.

(51) Int. Cl.

| | |
|---|---|
| ***A61K 35/747*** | (2015.01) |
| ***C12N 15/74*** | (2006.01) |
| ***C07K 14/335*** | (2006.01) |
| ***A61K 38/16*** | (2006.01) |
| ***A61K 38/13*** | (2006.01) |
| ***C12N 1/20*** | (2006.01) |
| ***A61K 9/00*** | (2006.01) |

(52) U.S. Cl.

CPC .......... *C07K 14/335* (2013.01); *A61K 9/0053* (2013.01); *A61K 35/747* (2013.01); *A61K 38/13* (2013.01); *A61K 38/164* (2013.01); *C12N 1/20* (2013.01); *C12N 15/746* (2013.01)

(58) Field of Classification Search

None

See application file for complete search history.

(56) References Cited

U.S. PATENT DOCUMENTS

| | | | |
|---|---|---|---|
| 7,348,420 | B2 | 3/2008 | Klaenhammer et al. |
| 10,562,943 | B2 | 2/2020 | Lightfoot et al. |
| 2005/0112612 | A1 | 5/2005 | Klaenhammer et al. |
| 2012/0308994 | A1 | 12/2012 | Scholz et al. |

OTHER PUBLICATIONS

Skolnick et al. Trends in Biotechnology, 18: 34-39, 2000.*

Rudinger J. In: Peptide Hormones. (Ed) JA Parsons, University Park Press, pp. 1-7, 1976.*

Greenspan et al. Nature Biotechnology 17: 936-937, 1999.*

Ahern, P. P. et al. "Mining the human gut microbiota for effector strains that shape the immune system" *Immunity*, Jun. 19, 2014, pp. 1-18, vol. 40, No. 6.

Åvall-Jääskeläinen, S. et al. "Surface Display of the Receptor-Binding Region of the *Lactobacillus brevis* S-Layer Protein in *Lactococcus lactis* Provides Nonadhesive *Lactococci* with the Ability To Adhere to Intestinal Epithelial Cells" *Applied and Environmental Microbiology*, Apr. 2003, pp. 2230-2236, vol. 69, No. 4.

Åvall-Jääskeläinen, S. et al. "*Lactobacillus* surface layers and their applications" *FEMS Microbiology Reviews*, Aug. 28, 2005, pp. 511-529, vol. 29.

Belkaid, Y. et al. "Role of the Microbiota in Immunity and Inflammation" *Cell*, Mar. 27, 2014, pp. 121-141, vol. 157.

Goh, Y. J. et al. "Development and Application of a upp-Based Counterselective Gene Replacement System for the Study of the S-Layer Protein SlpX of *Lactobacillus acidophilus* NCFM" *Applied and Environmental Microbiology*, May 2009, pp. 3093-3105, vol. 75, No. 10.

Hold, G. L. et al. "Role of the gut microbiota in inflammatory bowel disease pathogenesis: What have we learnt in the past 10 years?" *World Journal of Gastroenterology*, Feb. 7, 2014, pp. 1192-1210, vol. 20, No. 5.

Huttenhower, C. et al. "Inflammatory bowel disease as a model for translating the microbiome" *Immunity*, Jun. 19, 2014, pp. 1-23, vol. 40, No. 6.

Ivanov, I. I. et al. "Intestinal commensal microbes as immune modulators" *Cell Host Microbe.*, Oct. 18, 2012, pp. 1-22, vol. 12, No. 4.

Johnson, B. et al. "Identification of extracellular surface-layer associated proteins in *Lactobacillus acidophilus* NCFM" *Microbiology*, 2013, pp. 2269-2282, vol. 159.

Khan, M. W. et al. "Modulating intestinal immune responses by lipoteichoic acid-deficient *Lactobacillus acidophilus*" *Immunotherapy*, Feb. 2012, pp. 1-17, vol. 4, No. 2.

(Continued)

*Primary Examiner* — Sarvamangala Devi

(74) *Attorney, Agent, or Firm* — Saliwanchik, Lloyd & Eisenschenk

(57) ABSTRACT

The current invention provides a recombinant bacterium, the recombinant bacterium being genetically modified to decrease or eliminate the display of lipoteichoic acid (LTA), surface layer protein B (SlpB) and surface layer protein X (SlpX) on the surface of said bacterium. Efficacious therapies for a subject suffering from an inflammation mediated disease are also provided. The methods of the current invention comprise administering to a subject in need thereof a therapeutically effective amount of the recombinant *L. acidophilus* cells or a therapeutically effective amount of the isolated surface layer protein A (SlpA) or a non-naturally occurring derivative thereof. The recombinant *L. acidophilus* cells or SlpA isolated from *L. acidophilus* can be in a pharmaceutical composition comprising a pharmaceutically acceptable carrier and/or excipient. In an embodiment of the invention, the pharmaceutical composition is administered orally.

5 Claims, 47 Drawing Sheets
(41 of 47 Drawing Sheet(s) Filed in Color)

Specification includes a Sequence Listing.

(56) References Cited

OTHER PUBLICATIONS

Khazaie, K. et al. "Abating colon cancer polyposis by *Lactobacillus acidophilus* deficient in lipoteichoic acid" *Proceedings of the National Academy of Sciences of the United States of America*, Jun. 26, 2012, pp. 10462-10467, vol. 109, No. 26.

Konstantinov, S. R. et al. "S layer protein A of *Lactobacillus acidophilus* NCFM regulates immature dendritic cell and T cell functions" *Proceedings of the National Academy of Sciences of the United States of America*, Dec. 9, 2008, pp. 19474-19479, vol. 105, No. 49.

Lightfoot, Y. L. et al. "Tailoring gut immune responses with lipoteichoic acid-deficient *Lactobacillus acidophilus*" *Frontiers in Immunology*, Feb. 6, 2013, pp. 1-6, vol. 4, No. 25.

Lightfoot, Y. L. et al. "SIGNR3-dependent immune regulation by *Lactobacillus acidophilus* surface layer protein A in colitis" *The EMBO Journal*, 2015, pp. 881-895, vol. 34, No. 7.

Major, G. et al. "Irritable bowel syndrome, inflammatory bowel disease and the microbiome" *Current Opinion in Endocrinology, Diabetes, and Obesity*, Feb. 2014, pp. 15-21, vol. 21, No. 1.

Maslowski, K. M. et al. "Diet, gut microbiota and immune responses" *Nature Immunology*, Jan. 2011, pp. 5-9, vol. 12, No. 1.

Mcdermott, A. J. et al. "The microbiome and regulation of mucosal immunity" *Immunology*, 2013, pp. 24-31, vol. 142.

Mohamadzadeh, M. et al. "Regulation of induced colonic inflammation by *Lactobacillus acidophilus* deficient in lipoteichoic acid" *Proceedings of the National Academy of Sciences of the United States of America*, Mar. 15, 2011, pp. 4623-4630, vol. 108, No. 1.

Sára, M. et al. "S-Layer Proteins" *Journal of Bacteriology*, Feb. 2000, pp. 859-868, vol. 182, No. 4.

Saber, R. et al. "Lipoteichoic acid-deficient *Lactobacillus acidophilus* regulates downstream signals" *Immunotherapy*, 2011, pp. 1-11, vol. 3, No. 3.

Sahay, B. et al. "Advancing the use of *Lactobacillus acidophilus* surface layer protein A for the treatment of intestinal disorders in humans" *Gut Microbes*, 2015, pp. 392-397, vol. 6, No. 6.

Saunders, S. P. et al. "C-Type Lectin SIGN-R1 Has a Role in Experimental Colitis and Responsiveness to Lipopolysaccharide" *The Journal of Immunology*, Feb. 2010, pp. 2627-2637, Supp p. 1, vol. 184.

Wang, F-J. et al. "Tandem Multimer Expression and Preparation of Hypoglycemic Peptide MC6 from *Momordica charantia* in *Escherichia coli*" 2012, pp. 612-619, vol. 166.

Zadeh, M. et al. "Induction of intestinal pro-inflammatory immune responses by lipoteichoic acid" *Journal of Inflammation*, 2012, pp. 1-12, vol. 9, No. 7.

Written Opinion in International Application No. PCT/US2015/055620, dated Mar. 31, 2016, pp. 1-5.

* cited by examiner gi|58336516 (100%), 46,569.0 Da
S-layer protein [Lactobacillus acidophilus NCFM]
29 exclusive unique peptides, 49 exclusive unique spectra, 218 total spectra, 238/444 amino acids (54% coverage)

```
MKKNLRIVSA AAAALLAVAP VAASAVSTVS AATTINASSS AINTNTNAKY DVDVTPSVSA VAANTANNTP AIAGNLTGTI
SASYNGKTYT ANLKADTENA TITAAGSTTA VKPAELAAGV AYTVTVNDVS FNFGSENAGK TVTLGSANSN VKFTGTNSDN
QTETNVSTLK VKLDQNGVAS LTNVSIANVY AINTTDNSNV NFYDVTSGAT VTNGAVSVNA DNQGQVNVAN VVAAINSKYF
AAQYADKKLN TRTANTEDAI KAALKDQKID VNSVGYFKAP HTFTVNVKAT SNTNGKSATL PVVVTVPNVA EPTVASVSKR
INHNAYYYDK DAKRVGTDSV KRYNSVSVLP NTTTINGKTY YQVVENGKAV DKYINAANID GTKRTLKHNA YVYASSKKRA
NKVVLKKGEV VTTYGASYTF KNGQKYYKIG DNTDKTYVKV ANFR
```

gi|362076610 (100%), 49,364.6 Da
surface layer protein [Lactobacillus acidophilus]
1 exclusive unique peptides, 2 exclusive unique spectra, 118 total spectra, 85/467 amino acids (18% coverage)

```
MKKNLRIVSA AAAALLAVAP VAASAVSTVS AADATTTTTA TTTTNKPTVD LTGAGAVTNA AKTVTVTPNF TLTAAIAKDG
KVTASATLQG TITASLNGTS VTANVIDAAK GITLKSNSGY TTIYKYDANT NTTENNLGKW NEKTNDVYVK AGNDYQVELT
GVGFSFGSAN ANKEVSLKLP SNVTVKGVKD NKVTLDQYGN VTNLTFIVKD IKAYDATNTS AVQFYNTNSG LIESKATYMA
LADNNGNLNV NTLLNGLNKQ YKAVQLQNGE LKDVTVTTTA ADLTAELTKA GIKVNAAGDF EAPASFTATL TAKSEVNGKV
ATLPVTVTVP NGKVTTVDSV SKRIMHNAYF YDKDAKRVGT DSVKRYASVS VLPNTTTING KAYYQVVENG KAVDKYINAA
NIDGTKRTLK HNAYVYASSK KRANKVVLKK GEVVTTYGAS YTFKNGQKYY KIGNNTDKTY VKVANFR
```

FIG. 15C

*LACTOBACILLUS ACIDOPHILUS* SURFACE LAYER PROTEIN A (SLPA) AS A THERAPEUTIC AGENT FOR THE TREATMENT OF INFLAMMATORY DISEASES

CROSS-REFERENCE TO RELATED APPLICATIONS

This application is a divisional of U.S. application Ser. No. 15/521,418, filed Apr. 24, 2017, now U.S. Pat. No. 10,562,943, which is the U.S. national stage application of International Patent Application No. PCT/US2015/055620, filed Oct. 15, 2015, which claims the benefit of U.S. Provisional Application Ser. No. 62/068,338, filed Oct. 24, 2014, the disclosures of which are hereby incorporated by reference in their entirety, including all figures, tables and amino acid or nucleic acid sequences.

The Sequence Listing for this application is labeled "Seq-Liste.txt" which was created on Jan. 12, 2019 and is 63 KB. The entire content of the sequence listing is incorporated herein by reference in its entirety.

This invention was made with government support under AI093370 awarded by The National Institutes of Health and under W81XWH-12-1-0368 awarded by the United States Department of Defense. The government has certain rights in the invention.

BACKGROUND OF THE INVENTION

The gastrointestinal (GI) microbiota plays a critical role in determining the immunologic outcome of various signaling events in host cells via their gene products, exceeding the human genome by a hundredfold (Ley et al., 2006; Qin et al., 2010). As such, the composition of the GI microbiota and host immunity are mutualistic and continuously influence each other (Maslowski and Mackay, 2011; McDermott and Huffnagle, 2014).

Intestinal homeostasis is tightly controlled by regulatory immune mechanisms, which are established by the interactions of the trillions of microbes and their gene products with numerous pattern recognition receptors (PRRs), including C-type lectin receptors (CLRs), such as SIGNR3 (Konstantinov et al., 2008; Osorio and Reis e Sousa, 2011). Disruption of this delicate balance by inimical signals has devastating consequences that may result in intestinal disorders, including inflammatory bowel disease (IBD). When this occurs, highly activated innate cells trigger intestine-infiltrating pathogenic T cell subsets (e.g., Th1, Th17), and regulatory T cells (Tregs) with pro-inflammatory characteristics (Geremia et al., 2014; Khazaie et al., 2012; Neurath, 2014) that ultimately drive tissue destruction and intestinal disease progression. Innate cells (e.g., dendritic cells, macrophages) are the initial targets of either culpable microbes or their gene products, which subsequently affect the regulation/stimulation of intestinal immunity (Atarashi et al., 2013; Ivanov and Honda, 2012; Yang et al., 2014). Given these entwined relationships, it is not surprising that microbial products have been linked to the pathology of intestinal auto-inflammation (Nicholson et al., 2012). The underlying associations between gut microbes and inflammatory diseases (e.g., IBD) have been well documented; however, the cellular and molecular mechanisms by which intestinal commensal gene product(s) and their molecular receptor(s) impact immune responses remain unclear.

Information regarding the immunobiologic functions of *Lactobacillus acidophilus* surface layer proteins (Slps) is relatively limited. Slps are paracrystalline (glyco) protein arrays that are abundantly present on the cell surfaces of most eubacteria and archaea, including *L. acidophilus* (Johnson et al., 2013). *L. acidophilus* NCFM possesses three Slp-encoding genes: slpA (LBA0169), slpB (LBA0175), and slpX (LBA0512) (Goh et al., 2009). Diverse functional roles have been proposed for Slps, including cell shape determinants, molecular sieves, protective layers against viral infection, anchoring sites for surface-associated enzymes and facilitators of cellular adhesion through PRRs, including C-type lectins (CLECs) (Konstantinov et al., 2008).

CLECs recognize carbohydrate structures on self and non-self antigens (Engering et al., 2002; Osorio and Reis e Sousa, 2011). Eighteen CLECs, including DC-specific ICAM-3-grabbing nonintegrin (DC-SIGN), have been identified on dendritic cells (DCs) and macrophages (MPs) (Ehlers, 2010; van Kooyk and Geijtenbeek, 2003). DC-SIGN, which was previously shown to bind *L. acidophilus*-SlpA in vitro (Konstantinov et al., 2008), is a calcium-dependent carbohydrate-binding protein with specificity for the mannose-containing glycans of microbial surface components and fucose-containing Lewis antigens (Ehlers, 2010). Of the eight murine homologs of DC-SIGN, SIGNR3 (CD209d) exhibits the most biochemical similarity to human DC-SIGN (Powlesland et al., 2006).

SIGNR3 contains a carbohydrate recognition domain (CRD) and signals through a hemi-immunoreceptor tyrosine-based activation motif (hemi-ITAM) pathway (Tanne et al., 2009). Such signaling potentially downregulates the ubiquitously expressed leukotriene $A_4$ hydrolase ($LTA_4H$) (Tobin et al., 2010) that catalyzes proinflammatory leukotriene $B_4$ ($LTB_4$) synthesis from $LTA_4$ (Snelgrove et al., 2010), which consequently activates interleukin (IL)-1β production. Here, we identify SlpA as a key effector molecule expressed by *L. acidophilus*, and demonstrate its in vivo protective role in murine colitis models. Moreover, we provide evidence that protection by *L. acidophilus*-SlpA is conferred via signaling through a single CLR, namely SIGNR3.

As discussed above, normal gut immune responses dictate that resident innate and adaptive immune cells must coexist with the large number of microbes inhabiting the GI tract while still being able to mount an immune response against invading pathogens. Maintenance of immune homeostasis toward commensal bacteria and their microbial gene products is essential in the prevention of chronic inflammation in the gut. Overt intestinal inflammation is a hallmark of IBD. Current therapies for the management of IBD include antibiotic regimens to prevent the outgrowth and systemic dissemination of pathogenic microorganisms, as well as corticosteroids and immunomodulators to decrease the inflammatory response in the intestines. However, these therapies are not without undesirable and harmful side effects, as antibiotics also deplete the beneficial intestinal microflora, and corticosteroids and immunomodulators act as global immune suppressors, thereby increasing the risk of infection and cancer. Thus, there is a need for identifying new therapeutic agents for the treatment of such diseases.

BRIEF SUMMARY OF THE INVENTION

The current invention provides a recombinant bacterium, for example, a recombinant *Lactobacillus acidophilus*, the recombinant bacterium being genetically modified to decrease or eliminate the display of lipoteichoic acid (LTA), surface layer protein B (SlpB) and surface layer protein X (SlpX) on the surface of said bacterium.

The current invention also provides an efficacious therapy for a subject suffering from an inflammation mediated disease (inflammatory diseases), for example, an autoinflammatory disease, such as IBD or other inflammatory diseases, such as allergies, ankylosing spondylitis, Crohn's disease, diabetes, Type I diabetes, gastroesophageal reflux disease, Hashimoto's thyroiditis, hyperthyroidism, hypothyroidism, interstitial cystitis (IC), Lofgren's syndrome, lupus erythematosis, myasthenia gravis, multiple sclerosis, osteoarthritis, polymyalgia rheumatica, prostatitis, psoriasis, psoriatic arthritis, Raynaud's syndrome/phenomenon, reactive arthritis (Reiter syndrome), restless leg syndrome, reflex sympathetic dystrophy (RSD), rheumatoid arthritis, scleroderma, Sjögren's syndrome, ulcerative colitis and uveitis. The methods of the current invention comprise administering to a subject in need thereof a therapeutically effective amount of recombinant *L. acidophilus* cells of the current invention or a therapeutically effective amount of purified surface layer protein A (SlpA), for example, SlpA isolated from *L. acidophilus*. In one embodiment, the *L. acidophilus* cells belong to *L. acidophilus* strain NCK2187 which is a bacterium genetically modified to decrease or eliminate the display of LTA, SlpB and SlpX on the surface. Another embodiment provides for the recombinant expression of SlpA in bacterial cells that are devoid of LTA, SlpB and SlpX expression on the cell surface.

The recombinant bacterial cells (e.g., *L. acidophilus* cells) or SlpA isolated from *L. acidophilus* can be formulated into a pharmaceutical composition comprising a pharmaceutically acceptable carrier and/or excipient (optionally in combination with other therapeutic agents). In an embodiment of the invention, the pharmaceutical composition is administered orally.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

P<0.01 and *P<0.001 representing the specified group by its color compared with PBS.

Figure 14A:
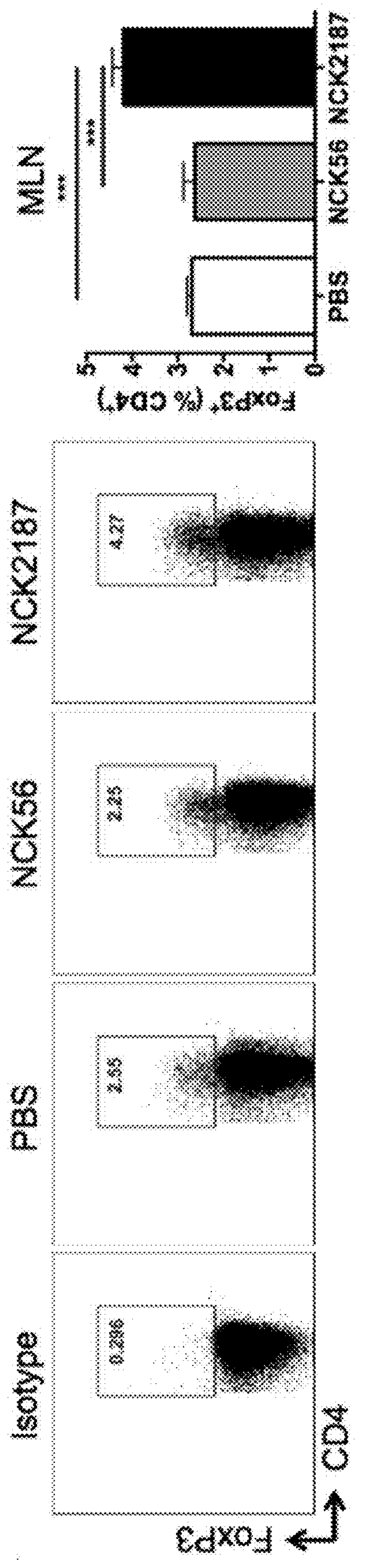
Figure 14B:
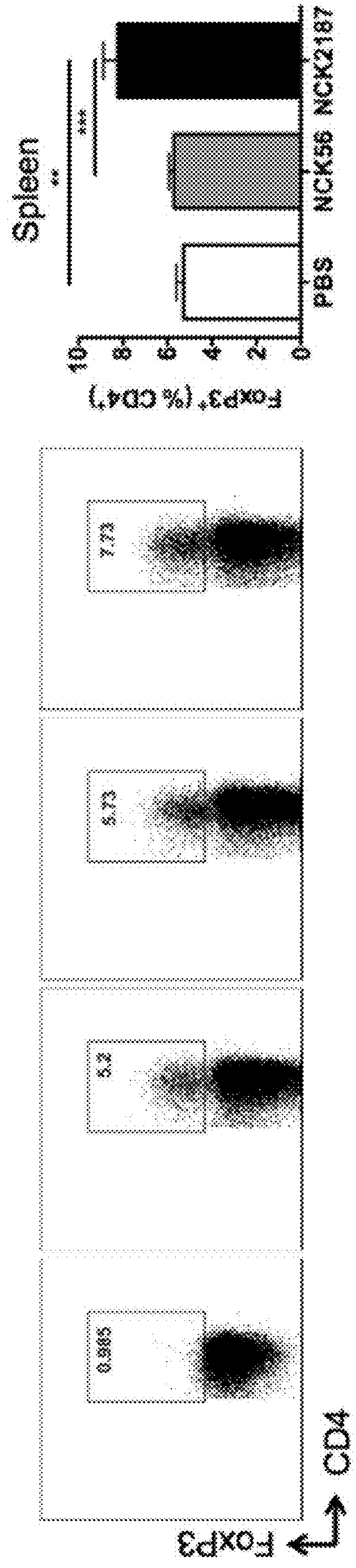

FIGS. 14A-14B. NCK2187 induces the generation of Tregs in healthy controls. C57BL/6 mice were orally gavaged with $10^9$ CFU NCK56 (WT), NCK2187 ($SlpA^+$), or left untreated; immune responses were analyzed by flow cytometry 3 days-post gavage. When compared to untreated or NCK56-treated mice, NCK2187 led to an expansion of total Tregs in the mesenteric lymph nodes (MLN; FIG. 14A) and spleens (FIG. 14B) of the mice tested. P<0.01 and *P<0.001 compared with PBS.

Figure 15A:
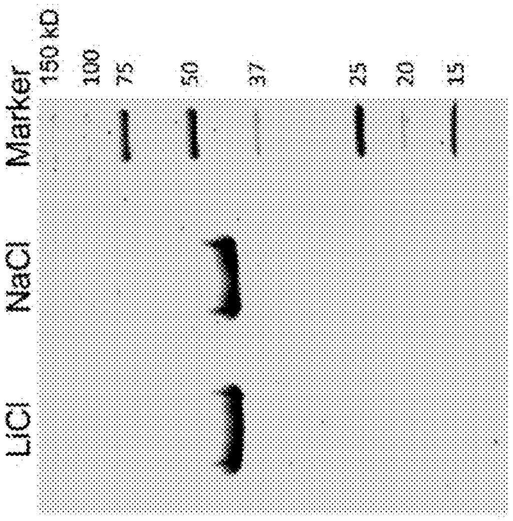
Figure 15B:
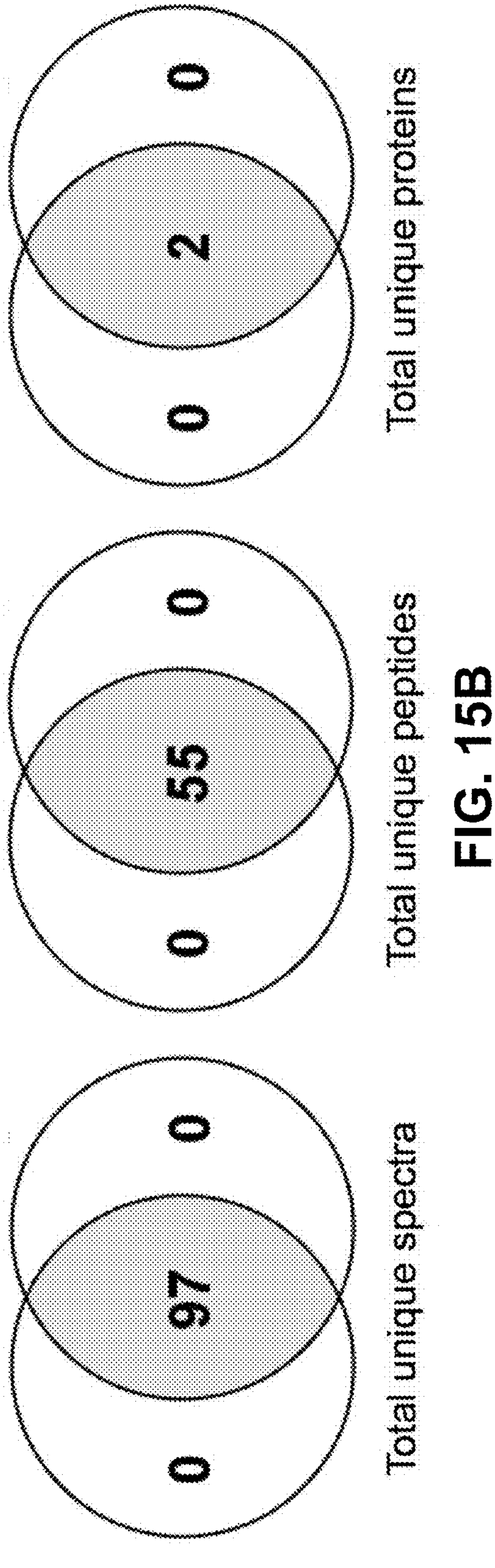

FIGS. 15A-15C. *L. acidophilus*-SlpA isolation by NaCl. *L. acidophilus*-SlpA was isolated and purified using NaCl. A. SDS-PAGE containing 2.5 μg of LiCl- and NaCl-isolated SlpA stained with COOMASSIE BLUE to visualize the purified protein. B-C. Mass spectrometry data analyzed on the Scaffold (Searle 2010) platform showed 97 unique spectra with 55 unique peptides with the possibility of two proteins (B). The predicted protein gi|158336516 (SlpA, SEQ ID NO: 4) shows 54% coverage whereas gi|362076610 (SlpB, SEQ ID NO: 56) reveals only 18% of coverage (highlighted portion. C). The regions of SlpB matching the generated peptides are common between SlpA and SlpB (shown in the red box, C), and no single unique peptide from SlpB was identified.

FIGS. 16A-16E. NaCl-purified SlpA is not toxic to mice. A-E. C57BL/6 mice were treated orally every other day with SlpA (0, 150, 300, 600 μg/100 μL per mouse), for a total of four times. One-week later, mice were sacrificed and a whole blood chemistry profile was generated for each mouse with a comprehensive metabolic chemistry panel, using a VetScan V2S analyzer. All animal experiments were performed under the guidelines of the Animal Welfare Act and the Public Health Policy on Humane Care, and with approval by the Institutional Animal Care and Use Committee (IACUC protocol 201406559) at the University of Florida.

FIGS. 17A-17E. Generated mAb BM1 recognizes *L. acidophilus*-SlpA. C57BL/6 mice were immunized once a week for 3 months with 100 μg of SlpA, and 300 μg of heat-killed *Lactobacillus* gasseri as adjuvant. Polyclonal sera were tested for recognition of isolated SlpA by Western Blot (WB), and splenic cells from SlpA-reactive mice were fused with Sp2/0 myeloma cells at a ratio of 7:1. Hybridomas were seeded on semi-solid medium for clone selection and screening. Subsequently, clones were screened by ELISA for SlpA reactivity. Reactive clones were isotyped and all IgM secretors removed. Clone BM1 (IgG) was selected for its ability to recognize SlpA by WB (A), flow cytometry (B), confocal microscopy (C), and ELISA (D, E). A. *L. acidophilus*-SlpA detection by WB with BM1. 100 ng of purified SlpA, $10^8$ CFU *L. acidophilus* (L. a.), $10^8$ CFU *L. reuteri* (L. r.), or 100 ng of BSA. Proteins separated by SDS-PAGE were transferred onto a PVDF membrane and detected by BM1. B. *L. acidophilus*-SlpA detection with BM1 by flow cytometry. Carboxylated Dynabeads were coated with purified SlpA and reactivity of BM1 mAb confirmed by Canto II flow cytometry. Data were analyzed by FlowJo. Experiments were performed at least three times with similar trends. C. *L. acidophilus*-SlpA detection with BM1 by confocal microscopy. RAW 264.7 cells were pulsed for 1 or 3 hrs with NaCl purified SlpA (10 μg/mL). Subsequently, cells were fixed and stained with BM1 mAb for detection by confocal microscopy. Cells were incubated with BM1 mAb, overnight. Cells were washed and subsequently incubated with a secondary antibody (ALEXA FLUOR 488 anti-mouse IgG1, 1:100) for 4 hrs. Nuclei were stained with DAPI (15 min) and visualized by a Zeiss confocal microscope. D. *L. acidophilus*-SlpA detection with BM1 by ELISA. ELISA plates were coated with 500 ng of purified SlpA overnight, and binding by BM1 was tested thereafter. E. Germ-free (GF) mice were orally treated with $10^9$ CFU *L. acidophilus,* 150 μg of SlpA, or left untreated. Fecal pellets from these mice were used to coat ELISA plates; BSA was used as a negative control. BM1 by ELISA. ELISA plates were coated with 500 ng of purified SlpA overnight, and binding by BM1 was tested thereafter. E. Germ-free (GF) mice were orally treated with $10^9$ CFU *L. acidophilus,* 150 μg of SlpA, or left untreated. Fecal pellets from these mice were used to coat ELISA plates; BSA was used as a negative control. BM1 mAb only bound to plates coated with feces derived from treated mice. All animal experiments were performed under the guidelines of the Animal Welfare Act and the Public Health Policy on Humane Care, and with approval by the Institutional Animal Care and Use Committee (IACUC protocol 201406559) at the University of Florida. *denotes statistical significance p<0.01, *p<0.001.

BRIEF DESCRIPTION OF THE SEQUENCES

SEQ ID NO: 1: Amino acid sequence of phosphoglycerol transferase protein from *L. acidophilus* (Genbank Accession No. AAV42337.1).

SEQ ID NO: 2: Amino acid sequence of SlpB protein from *L. acidophilus* (Genbank Accession No. YP_193105).

SEQ ID NO: 3: Amino acid sequence of SlpX protein from *L. acidophilus* (Genbank Accession No. YP_193425).

SEQ ID NO: 4: Amino acid sequence of SlpA protein from *L. acidophilus* (Genbank Accession No. P35829).

SEQ ID NO: 5 to 46: The list of primer sequences for Real-Time PCR analyses (see Table 1).

SEQ ID NO: 47 to 55: SlpA protein sequences as discussed below.

DETAILED DISCLOSURE OF THE INVENTION

The current invention provides a bacterium lacking on its surface LTA, SlpB and SlpX. The current invention also provides SlpA as an effector molecule expressed by bacteria, for example, *L. acidophilus* and its in vivo protective role in inflammation mediated diseases (inflammatory diseases), for example, inflammation mediated diseases of the gastrointestinal tract such as IBD or other inflammatory diseases, such as allergies, ankylosing spondylitis, Crohn's disease, diabetes, Type I diabetes, gastroesophageal reflux disease, Hashimoto's thyroiditis, hyperthyroidism, hypothyroidism, Irritable Bowel Syndrome (IBS), interstitial cystitis (IC), Löfgren's syndrome, lupus erythematosis, myasthenia gravis, multiple sclerosis, osteoarthritis, polymyalgia rheumatica, prostatitis, psoriasis, psoriatic arthritis, Raynaud's syndrome/phenomenon, reactive arthritis (Reiter syndrome), restless leg syndrome, reflex sympathetic dystrophy (RSD), rheumatoid arthritis, scleroderma, Sjögren's syndrome, ulcerative colitis and uveitis.

A bacterium lacking LTA and methods of preparing such bacterium are described in US Patent Application Publication 20130224153, the contents of which are incorporated by reference herein in its entirety, particularly, paragraphs [0031] to [0034]. In addition to modifications required to decrease or eliminate display of LTA on the surface, the current invention provides a bacterium further modified to decrease or eliminate the display of SlpB and SlpX on the surface. In some embodiments, bacterial cells lacking LTA expression on the cell surface are genetically modified to decrease or eliminate SlpB and SlpX expression on the cell surface. Such cells can be genetically modified to expression SlpA and used in the methods disclosed herein. Yet other embodiments utilize bacterial cells genetically modified to express SlpA but which lack LTA expression on the cell surface and also lack genes encoding SlpB and SlpX or orthologs of SlpB and SlpX (i.e., protein homologs that are present within different species and have very similar or identical function). Non-limiting examples of such bacterial cells include those that lack genes encoding phosphoglycerol transferase protein (Genbank Accession No. AAV42337.1; SEQ ID NO: 1), SlpB and SlpX or orthologs of phosphoglycerol transferase (Genbank Accession No. AAV42337.1), SlpB and SlpX. For example, the cells do not express SEQ ID NO: 2 or the SlpB polypeptides associated with Uniprot access numbers Q48508, C2HR61, Q5FMK0, Q8GFE5, J9W284, J9W905, B1H0V4, H6VTN5, Q09FL7, V7HZR4, S4NDQ7, S4NKH4, S4NL65 and S4NQU9 and SEQ ID NO: 3 or the SlpX polypeptides associated with SlpX protein are provided by Uniprot access numbers C2HMW6, S6E4Y8, S6DRU6, S6DL03, S6E593, S6DQJ3, FOTJ46, Q5FLN0, D4YUC6, R5ZGF3, E4SM72, F2M2V8, C2KB60, D5H1S0, I7KQ44, U6FUJ7, U6FJC0, U6F914, U6F7V6, U6F834, U4QN79, U4QA33, F3MP54, F0NWR2, F0NVR1, F6CEM8, F6CBQ1, I7JYF2 and C2ELK0.

In certain embodiments, the phosphoglycerol transferase protein comprises SEQ ID NO: 1, SlpB protein comprises the amino acid sequence of SEQ ID NO: 2 and SlpX protein comprises the amino acid sequence of SEQ ID NO: 3. Accordingly, in addition to the modifications required to reduce the surface display of LTA, the bacterium of the current invention has been further genetically modified to decrease or eliminate the expression of a polypeptide comprising amino acid sequence of SEQ ID NO: 1, comprising amino acid sequence of SEQ ID NO: 2 and a polypeptide comprising the amino acid sequence of SEQ ID NO: 3. In an embodiment, in addition to the modifications required to reduce or eliminate the surface display of LTA, the bacterium of the current invention has decreased or eliminated expression of a polypeptide comprising the amino acid sequence having at least 70%, 80%, 90%, 95%, 97%, 98%, or 99% sequence identity to the amino acid sequence of SEQ ID NO: 1, at least 70%, 80%, 90%, 95%, 97%, 98%, or 99% sequence identity to the amino acid sequence of SEQ ID NO: 2 and a polypeptide comprising the amino acid sequence having at least 70%, 80%, 90%, 95%, 97%, 98%, or 99% sequence identity to the amino acid sequence of SEQ ID NO: 3.

Certain examples of phosphoglycerol transferase protein from *L. acidophilus* (Genbank Accession No. AAV42337.1) protein are provided by Uniprot access numbers Q5FLT7, A0A0D5MGR2, F3MQQ2, U6F845, U6FPM2, U6FK51, A8YTT6, U6F7B9, C7XM54, E3R4H1, C2KGR7, D0DKS2 and K1NT37 (each of which is hereby incorporated by reference in their entireties). Additional examples of phosphoglycerol transferase proteins are well known to a person of ordinary skill in the art and such embodiments are within the purview of the current invention.

Certain examples of SlpB protein are provided by Uniprot access numbers Q48508, C2HR61, Q5FMK0, Q8GFE5, J9W284, J9W905, B1H0V4, H6VTN5, Q09FL7, V7HZR4, S4NDQ7, S4NKH4, S4NL65 and S4NQU9 (each of which is hereby incorporated by reference in their entireties). Additional examples of SlpB proteins are well known to a person of ordinary skill in the art and such embodiments are within the purview of the current invention.

Certain examples of SlpX protein are provided by Uniprot access numbers C2HMW6, S6E4Y8, S6DRU6, S6DL03, S6E593, S6DQJ3, F0TJ46, Q5FLN0, D4YUC6, R5ZGF3, E4SM72, F2M2V8, C2KB60, D5H1S0, I7KQ44, U6FUJ7, U6FJC0, U6F914, U6F7V6, U6F834, U4QN79, U4QA33, F3MP54, FONWR2, F0NVR1, F6CEM8, F6CBQ1, I7JYF2 and C2ELK0 (each of which is hereby incorporated by reference in their entireties). Additional examples of SlpX proteins are well known to a person of ordinary skill in the art and such embodiments are within the purview of the current invention.

The genetic modifications resulting in decreased or eliminated expression of the polypeptides include, but are not limited to, deleting the entire coding region of the gene or a portion of the coding nucleotide sequence, introducing a frame shift mutation, a missense mutation, an insertion, by introducing a stop codon or a combinations of any of the aforementioned mutations. Additional mutations which would lead to decreased, or eliminated, expression of a polypeptide of interest and methods of introducing such mutations into a bacterium are well known to a person of ordinary skill in the art and such embodiments are within the purview of the claimed invention. In one embodiment of the invention, the upp-counterselective knockout strategy (described in Goh et al., 2009) which is hereby incorporated by reference in its entirety) was used to generate in-frame deletions in the slpB and slpX genes of *L. acidophilus* NCK2030 to produce *L. acidophilus* NCK2187.

In a certain embodiment, the lactic acid bacterium is a surface layer protein expressing *Lactobacillus*. These bacterial cells may also be referred to as probiotic bacterial cells. Non-limiting examples of such lactic acid bacteria include, but are not limited to, *L. acidophilus, L. amylolyticus, L. amylovorus, L. brevis, L. brevis* ssp *gravesensis, L. buchneri, L. crispatus, L. gallinarum, L. gigeriorum, L. helveticus/suntoryeus, L. hilgardii, L. kefiranofaciens, L. pasteurii, L. lactis* and *L. ultunensis.*

An embodiment provides a composition comprising the recombinant bacterium of the current invention and a pharmaceutically acceptable carrier and/or excipient.

The bacteria of the current invention provide protective role in inflammation mediated diseases, for example, inflammation mediated diseases of gastrointestinal tract such IBD. Accordingly, certain embodiments of the current invention provide methods of treating and/or preventing an inflammation mediated disease of the gastrointestinal system in a subject, the method comprising, administering to the subject a therapeutically effective amount of the bacterium of the current invention. In one embodiment, the bacterium is orally administered to the subject.

In certain embodiments of the invention a subject is a mammal. Non-limiting examples of a mammal treatable according to the methods of the current invention include mouse, rat, dog, guinea pig, cow, horse, cat, rabbit, pig, monkey, ape, chimpanzee, and human. Additional examples of mammals treatable with the methods of the current invention are well known to a person of ordinary skill in the art and such embodiments are within the purview of the current invention.

For the purposes of the current invention, a probiotic food refers to a food which contains microorganisms associated with beneficial effects to humans and animals upon ingestion of the probiotic food. Non-limiting examples of probiotic food include yogurt, fermented vegetable, kefir, sauerkraut, miso soup, pickle, tempeh and kimchi.

For the purposes of this invention the term "inflammation mediated disease" or "inflammatory disease" refers to a disease characterized by a dysregulation of the normal immune response. Inflammation mediated diseases (inflammatory diseases) can cause organ damage, and are associated with increased morbidity and/or mortality. An example of immune dysregulation is the inappropriate activation of inflammatory cytokines, such as IL-12, IL-6 or TNF alpha, whose actions lead to pathological consequences.

For the purposes of this invention the terms "treatment, treating, treat" or equivalents of these terms refer to healing, alleviating, relieving, altering, remedying, ameliorating, improving, or affecting the condition or the symptoms of a subject suffering with a disease, for example, a gastrointestinal disorder. The subject to be treated can be suffering from or at risk of developing the disorder, for example, a gastrointestinal disorder, including, for example, an IBD or be at risk of developing an IBD. When provided therapeutically, the bacterium is provided at (or shortly after) the onset of a symptom. The therapeutic administration of the substance serves to attenuate any actual symptom.

For the purposes of this invention, the terms "preventing, preventive, prophylactic" or equivalents of these terms are indicate that the recombinant bacterium is provided in advance of any disease symptoms and are a separate aspect of the invention (i.e., an aspect of the invention that is distinct from aspects related to the terms "treatment, treating, treat" or equivalents of these terms which refer to healing, alleviating, relieving, altering, remedying, ameliorating, improving, or affecting the condition or the symptoms of a subject suffering with an inflammatory disease, for example, a gastrointestinal disorder). The prophylactic administration of the recombinant bacterium serves to prevent or attenuate any subsequent symptoms or disease.

By "therapeutically effective dose," "therapeutically effective amount", or "effective amount" is intended to be an amount of a recombinant bacterium disclosed herein or the amount of SlpA that, when administered to a subject, decreases the inflammatory response, or reduces any increase in an inflammatory response as compared to untreated subjects. "Positive therapeutic response" refers to, for example, improving the condition of at least one of the symptoms of an inflammatory disorder.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual. Generally, the dosage of recombinant bacteria will vary depending upon such factors as the patient's age, weight, height, sex, general medical condition and previous medical history. In specific embodiments, it may be desirable to administer the bacterium in the range of about $10^4$ to about $10^{12}$ CFU, $10^5$ to $10^{11}$ CFU, $10^6$ to $10^{10}$ CFU, $10^8$ to $10^{10}$ CFU or $10^8$ to $10^{12}$ CFU.

In some embodiments of the invention, the method comprises administration of multiple doses of the bacterium. The method may comprise administration of 1, 2, 3, 4, 5, 6, 7, 8, 9, 10, 15, 20, 25, 30, 35, 40, or more therapeutically effective doses of a composition comprising the bacterium as described herein. In some embodiments, doses are administered over the course of 1 day, 2 days, 3 days, 4 days, 5 days, 6 days, 7 days, 10 days, 14 days, 21 days, 30 days, or more than 30 days. The frequency and duration of administration of multiple doses of the compositions is such as to reduce or prevent an inflammatory response and thereby treat or prevent a gastrointestinal disorder. Moreover, treatment of a subject with a therapeutically effective amount of the recombinant bacterium of the invention can include a single treatment or can include a series of treatments. It will also be appreciated that the effective dosage of a bacterium used for treatment may increase or decrease over the course of a particular treatment. Changes in dosage may result and become apparent from the results of diagnostic assays for detecting inflammation known in the art and described herein.

The present invention also includes combinations of the recombinant bacteria with one another, and/or with one or more other agents useful in the treatment of an inflammation mediated disease of the GI tract. For example, bacteria of the invention may be administered in combination with effective doses of conventional anti-inflammatory agents, such as sulfasalazine, cyclosporine, prednisone, methylprednisone, budesonide, mesalamine, azathioprine, TNF inhibitors, methotrexate, or 6-mercaptopurine, a corticosteroid, infliximab or combinations thereof, for treatment of inflammation mediated diseases of the GI tract. The term "administration in combination" refers to both concurrent and sequential administration of the active agents. The combination therapies are of course not limited to the agents provided herein, but include any composition for the treatment of inflammatory disorders.

In certain embodiments, the inflammation mediated disease treated according to the current invention is IBD. Non-limiting examples of IBD include Crohn's disease or ulcerative colitis. Additional examples of IBD are well known to a person of ordinary skill in the art and such embodiments are within the purview of the current invention. As discussed above, the disclosed methods and compositions are aimed at improving the condition of at least one of the symptoms of an inflammatory disorder, such as IBD.

The current invention also provides SlpA as an effector molecule expressed by bacteria and which provide protective role in inflammation mediated diseases, for example, inflammation mediated diseases of gastrointestinal tract such IBD. Accordingly, certain embodiments of the current invention provide an isolated bacterial SlpA protein or a non-naturally occurring protein derivative thereof.

An example of bacterial SlpA protein is provided by a protein having the sequence of SEQ ID NO: 4 or a protein having at least 95% sequence identity to the sequence of SEQ ID NO: 4. Certain other examples of SlpA protein are provided by Uniprot access numbers C2HR60 (SEQ ID NO: 47), P35829 (SEQ ID NO: 48), G1UE81 (SEQ ID NO: 49), Q9Z4J9 (SEQ ID NO: 50), H6VTN4 (SEQ ID NO: 51), Q09FM2 (SEQ ID NO: 52), L7YE91 (SEQ ID NO: 53), K8DVK7 (SEQ ID NO: 54) and F0NUB7 (SEQ ID NO: 55) (each of which is hereby incorporated by reference in its entirety). Additional examples of SlpA proteins are well known to a person of ordinary skill in the art and such embodiments are within the purview of the current invention for use in formulation of the compositions disclosed herein as well as the methods of using such compositions for the treatment of inflammatory diseases.

For the purposes of this invention a "non-naturally" occurring protein derivative indicates that the protein derivative is different than the its naturally occurring counterpart in some manner. Certain examples of modifications which can distinguish a non-naturally occurring protein derivative from its naturally occurring counterpart include mutations in the amino acid sequences (e.g., point mutations or the introduction of one or more glycosylation site into the protein), non-naturally occurring post-translational modifications (e.g. glycosylation or phosphorylation patterns), attachment to the protein of extraneous molecules (e.g. molecular labels, such as radioisotopes or fluorescent labels, polyethyleneglycol (PEG), etc.). Additional examples of such modifications are well known to a person of ordinary skill in the art and such embodiments are within the purview of the current invention.

In one embodiment, the non-naturally occurring SlpA protein derivative according to the current invention comprises a molecular label conjugated to a bacterial SlpA protein, for example, SlpA protein having the sequence of SEQ ID NO: 4 or the protein having at least 95% sequence identity to the sequence of SEQ ID NO: 4. The label can be a radiolabel, fluorescent label, affinity label, targeting label.

In another embodiment, the non-naturally occurring SlpA protein derivative according to the current invention comprises a protein having one or more mutations in the naturally occurring sequence of a bacterial SlpA protein, for example, SlpA protein having a sequence of SEQ ID NO: 4 or having a sequence at least 95% identical to the sequence of SEQ ID NO: 4. In certain embodiments, the non-naturally occurring SlpA protein derivative comprises about 1 to about 20 mutations, about 3 to about 15 mutations, or about 5 to about 10 mutations. In another embodiment, the mutations do not negatively affect the ability of the non-naturally occurring SlpA protein derivative of the current invention of protecting against inflammation mediated diseases, for example, inflammation mediated diseases of gastrointestinal tract such IBD.

An embodiment of the current invention also provides a composition comprising the non-naturally occurring SlpA protein derivative and a pharmaceutically acceptable carrier and/or excipient.

The pharmaceutically acceptable carrier and/or excipient comprise substances, such as an inert vehicle, or pharmaceutical acceptable adjuvants, preservatives etc. Examples pharmaceutically acceptable substances are well known to a person of ordinary skill in the art and such embodiments are within the purview of the current invention.

The pharmaceutical composition may be a liquid formulation or a solid formulation. When the pharmaceutical composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the pharmaceutical composition is a liquid formulation it may be formulated as an oral solution, a suspension, an emulsion or syrup. Said composition may further comprise a carrier material independently selected from, but not limited to, the group consisting of lactic acid fermented foods, fermented dairy products, resistant starch, dietary fibers, carbohydrates, proteins, and glycosylated proteins.

Pharmaceutical compositions, as disclosed herein, can be formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. Pharmaceutical composition according to the invention may also be formulated to release active agents substantially immediately upon administration or at any predetermined time or time period after administration.

For oral administration, the composition can be formulated into conventional oral dosage forms such as tablets, capsules, powders, granules and liquid preparations such as syrups, elixirs, and concentrated drops. Non-toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials are also necessary. For example, starch, gelatin, sugars such as lactose or dextrose, and natural or synthetic gums can be used as binders. Disintegrants are also necessary in the tablets to facilitate break-up of the tablet. Disintegrants include starches, clays, celluloses, algins, gums and cross-linked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

Pharmaceutical composition can also be formulated as a food composition, a dietary supplement, a functional food, a medical food or a nutritional product as long as the required effect is achieved, i.e. treatment and/or prevention of an inflammatory disorder of the gastrointestinal tract. Said food composition may be chosen from the group consisting of beverages, yogurts, juices, ice creams, breads, biscuits, crackers, cereals, health bars, spreads and nutritional products. The food composition may further comprise a carrier material, wherein said carrier material is chosen from the group consisting of lactic acid fermented foods, fermented dairy products, resistant starch, dietary fibers, carbohydrates, proteins and glycosylated proteins.

Accordingly, the current invention provides a method of treating or preventing an inflammation mediated disease of the gastrointestinal system in a subject, the method comprising, administering to the subject a therapeutically effective amount of the composition comprising the SlpA protein or a non-naturally occurring SlpA derivative. In certain embodiments, the composition is orally administered to the subject. SlpA protein or a non-naturally occurring SlpA derivatives can be administered or formulated in combination with effective doses of conventional anti-inflammatory agents, such as sulfasalazine, cyclosporine, prednisone, methylprednisone, budesonide, mesalamine, azathioprine, TNF inhibitors, methotrexate, or 6-mercaptopurine, a corticosteroid, infliximab or combinations thereof, for treatment of inflammation mediated diseases of the GI tract. Non-limiting examples of such diseases include IBD, for example, Crohn's disease or ulcerative colitis.

Yet another aspect of the invention relates to a method of purifying SlpA comprising growing SlpA expressing bacterial cells, pelleting said bacterial cells from culture medium containing said bacterial cells, resuspending said bacterial cells in 5M NaCl for a period of 5 minutes to 24 hours, preferably between 30 minutes and two hours, to form an extraction composition, removing bacterial cells from said extraction composition by centrifugation to form a composition containing SlpA and dialyzing or filtering said composition using a dialysis bag or ultrafiltrating device having a molecular weight cut-off of 30 kDa to reduce the salt content of said composition containing SlpA. The method can further comprise the precipitation of SlpA protein in said dialyzed composition comprising SlpA (for example, with 1M NaCl or another suitable precipitating agent). The method can also further comprise the washing of said precipitated SlpA with water or a buffer and lyophilization of said washed SlpA.

In some embodiments of the purification methodology, the SlpA expressing bacterial cells do not express LTA, SlpB or orthologs thereof or SlpX or orthologs thereof. Alternatively, the SlpA expressing bacterial cells do not express phosphoglycerol transferase or orthologs thereof, SlpB or orthologs thereof or SlpX or orthologs thereof.

Thus, the bacterial cells, in some embodiments: a) express a protein that has the amino acid sequence of SEQ ID NO: 4 or the protein has the amino acid sequence at least 70%, 80%, 90%, 95%, 97%, 98%, or 99% identical to the sequence of SEQ ID NO: 4; and b) do not express (i) a polypeptide comprising the amino acid sequence of SEQ ID NO: 1 or a polypeptide having at least 70%, 80%, 90%, 95%, 97%, 98%, or 99% sequence identity to the amino acid sequence of SEQ ID NO: 1; (ii) a polypeptide comprising the amino acid sequence of SEQ ID NO: 2 or a polypeptide comprising the amino acid sequence having at least 70%, 80%, 90%, 95%, 97%, 98%, or 99% sequence identity to the amino acid sequence of SEQ ID NO: 2; and (iii) a polypeptide comprising the amino acid sequence of SEQ ID NO: 3 or a polypeptide having at least 70%, 80%, 90%, 95%, 97%, 98%, or 99% sequence identity to the amino acid sequence of SEQ ID NO: 3. In certain aspects of the invention, these bacterial cells are *Lactobacillus* strain, such as a *Lacotbacillus* strain is selected from the group consisting of *L. acidophilus, L. amylolyticus, L. amylovorus, L. brevis, L. brevis* ssp *gravesensis, L. buchneri, L. crispatus, L. gallinarum, L. gigeriorum, L. helveticus/suntoryeus, L. hilgardii, L. kefiranofaciens, L. pasteurii, L. lactis* and *L. ultunensis.*

Materials and Methods

Mice

C57BL/6 (B6), and B6 recombination-activating gene 1-deficient ($Rag1^{-/-}$) mice were purchased from Jackson Laboratories (Bar Harbor, Me.). Germ-free (GF) B6 mice were obtained from the National Gnotobiotic Rodent Resource Center at the University of North Carolina and maintained in the GF facilities at the University of Florida (UF). The mouse strain 031934-UCD, C57BL/6-$Cd209d^{tm1.1Cfg}$/Mmucd ($Signr3^{-/-}$) was provided by the NIH-sponsored Mutant Mouse Regional Resource Center (MMRRC) National System and was backcrossed at the Max Planck Institute of Colloids and Interfaces, Berlin, Germany. Genotyping of the Signr3 gene in WT and $Signr3^{-/-}$ mice was performed according to a protocol provided by the Consortium for Functional Glycomics. Dr. L. Morel (UF) contributed the FoxP3-GFP mice. Mice were bred in-house in the animal facility at the College of Veterinary Medicine, UF. Mice were maintained under specific pathogen-free, *Helicobacter*-free conditions and used at 6-8 weeks of age in accordance with the Animal Welfare Act and the Public Health Policy on Humane Care. Procedures were approved by UF's Institutional Animal Case and Use Committee (IACUC).

Bacterial Strains

The upp-counterselective knockout strategy was used to generate an in-frame deletion of the phosphoglycerol transferase gene within NCK2030 ($LTA^+$ $SlpB^-$ $SlpX^-$ $SlpA^+$), resulting in the generation of NCK2187 ($LTA^-SlpB^-SlpX^-$ $SlpA^+$) (Goh et al., 2009). Wild-type *L. acidophilus* NCFM (NCK56), and NCK2187 were propagated anaerobically in MRS broth (Difco, BD, Franklin Lakes, N.J.) at 37° C. for 15 hrs. In preparation for oral treatment, bacteria were washed twice with sterile PBS, and the number of colony-forming units (CFU) were estimated by measuring the optical density at 600 nm. The concentration of each *L. acidophilus* strain was accordingly adjusted. To determine the clearance kinetics of the different *L. acidophilus* strains, groups of mice (n=3) were orally gavaged with erythromycin-resistant ($Em^r$) NCK56 or NCK2187 ($1\times10^9$ CFU/100 μL/mouse). Fecal pellets were collected before gavage and every day thereafter for up to 7 days. Each fecal pellet was then resuspended in 10% MRS (0.2 g/2 mL). The homogenized material was serially diluted and plated onto MRS agar containing Em (2 μg/mL). The daily average excreted *L. acidophilus* was quantified. For the oral gavage of mice, each mouse received either $1\times10^9$ CFU of NCK56 or NCK2187 in 100 μL of PBS. Mice enrolled in steady-state studies were orally gavaged every 3 days for a total of 4 times, and immune changes analyzed at day 14. The gavage schedule was determined based on the clearance kinetics of the bacterial strains.

Surface Layer Protein A Isolation

SlpA was purified from NCK2187 with LiCl. Cultures from 18 h grown NCK2187 were pelleted at 5,000 rpm for 10 min. Bacterial pellets were washed with cold PBS and re-pelleted before extraction. Pellets were resuspended in 5 M LiCl or 5M NaCl (Sigma-Aldrich, St. Louis, Mo.), gently stirred for 30 min, and the bacteria removed by centrifugation (13,000 rpm, 15 min). Supernatants were dialyzed against distilled water overnight using a dialysis bag with a cut-off molecular weight of 30 kDa for salt removal. The protein precipitate was dissolved in 1 M LiCl or 1M NaCl and pelleted at 13,000 rpm for 30 min. The SlpA protein preparation was washed with water a minimum of three times before lyophilization (FreeZone, Labconco, Kansas City, Mo.). Freeze-dried SlpA was stored at 4° C. until used. SDS-PAGE gels and proteomics analyses were used to confirm SlpA purity. For oral gavage, mice were given 150 μg of SlpA in 300 μL PBS.

Lamina Propria Leukocyte (LPL) Preparation

Colonic lamina propria cells were isolated, as previously described (Lightfoot et al., 2014). Freshly isolated colons were cut into 0.5 cm sections and intraepithelial lymphocytes removed with a digestion buffer consisting of HBSS (GIBCO, Life Technologies, Grand Island, N.Y.) containing 5 mM EDTA (GIBCO, Life Technologies) and 10 mM HEPES (GIBCO, Life Technologies), for (20 min, 37° C.). Remaining colon tissues were digested in DMEM (GIBCO, Life Technologies) supplemented with 0.25 ng/mL Collagenase Type VII (Sigma-Aldrich), 0.125 U/mL Liberase™ Research Grade (Roche Applied Science, Indianapolis, Ind.), 10 mM HEPES, 0.1 M CaCl2 (Sigma-Aldrich), and 5% FBS (GIBCO, Life Technologies). Three digestions of 10 min each at 37° C. were performed. Single cell suspensions obtained were combined and stained for flow cytometry-based analyses or used for ex vivo studies.

Ex Vivo Stimulation of Colonic LPLs

Isolated colonic LPLs were co-cultured with NCK56 or NCK2187 for 12 h at 37° C. Supernatants were then collected and stored at −80° C. for later cytokine analyses using Bio-Plex Pro Mouse Cytokine Immunoassay kits (Bio-Rad, Hercules, Calif.). Activation phenotypes of DCs were analyzed by flow cytometry using the appropriate antibodies to quantify expression levels of MHC-II molecules and costimulatory markers.

Flow Cytometry and Antibodies

Colonic LPLs were stained as described previously (Lightfoot et al., 2014). Colonic LPLs were stained with LIVE/DEAD Aqua Dead Cell Stain Kit (Molecular Probes, Life Technologies). Washed cells were incubated with Mouse Fc Blocking Reagent (Miltenyi Biotec, Auburn, Calif.) per the manufacturer's instructions before staining with combinations of the following antibodies or their corresponding isotype controls: CD45 (30-F11), CD11c (N418), CD11b (M1/70), CD11b (M1/70), F4/80 (BM8), GR1 (RB6-8C5), I-A/I-E MHCII (2G9), CD3 (145-2C11), CD4 (RM4-5), CD8 (53-607), Pro-IL-1β (NJTEN3)/Rat IgG1, κ, IFNγ (XMG1.2)/Rat IgG1, κ, IL-17A (TC11-18H10.1)/Rat IgG1, κ, IL-10 (JES5-16E3)/Rat IgG2b, κ, LAP (TGF-β1, TW7-16B4)/Mouse IgG1, κ, FoxP3 (FJK-16A)/Rat IgG2a, κ, RORγt (AFKJS-9)/Rat IgG2a, κ. For the detection of intracellular cytokines, cells were fixed and permeabilized with BD Cytofix/Cytoperm (BD Biosciences). Colonic T cells were stimulated with phorbol 12-myristate 13-acetate (PMA) (50 ng/mL) and ionomycin (2.5 g/mL) in the presence of Brefeldin A (Biolegend) for 2.5 h. The Transcription Factor Fixation/Permeabilization kit from eBioscience was used for FoxP3 staining. After staining, a BD LSRFortessa (BD Biosciences) cell analyzer was used to acquire fixed cells. Data were analyzed with FlowJo software (Tree Star, Ashland, Oreg.).

Antibodies and their corresponding isotype controls were purchased from eBioscience (San Diego, Calif.), Biolegend (San Diego, Calif.), BD Pharmingen, or R&D Systems (Minneapolis, Minn.).

T Cell-Induced Colitis

Figure 3A:
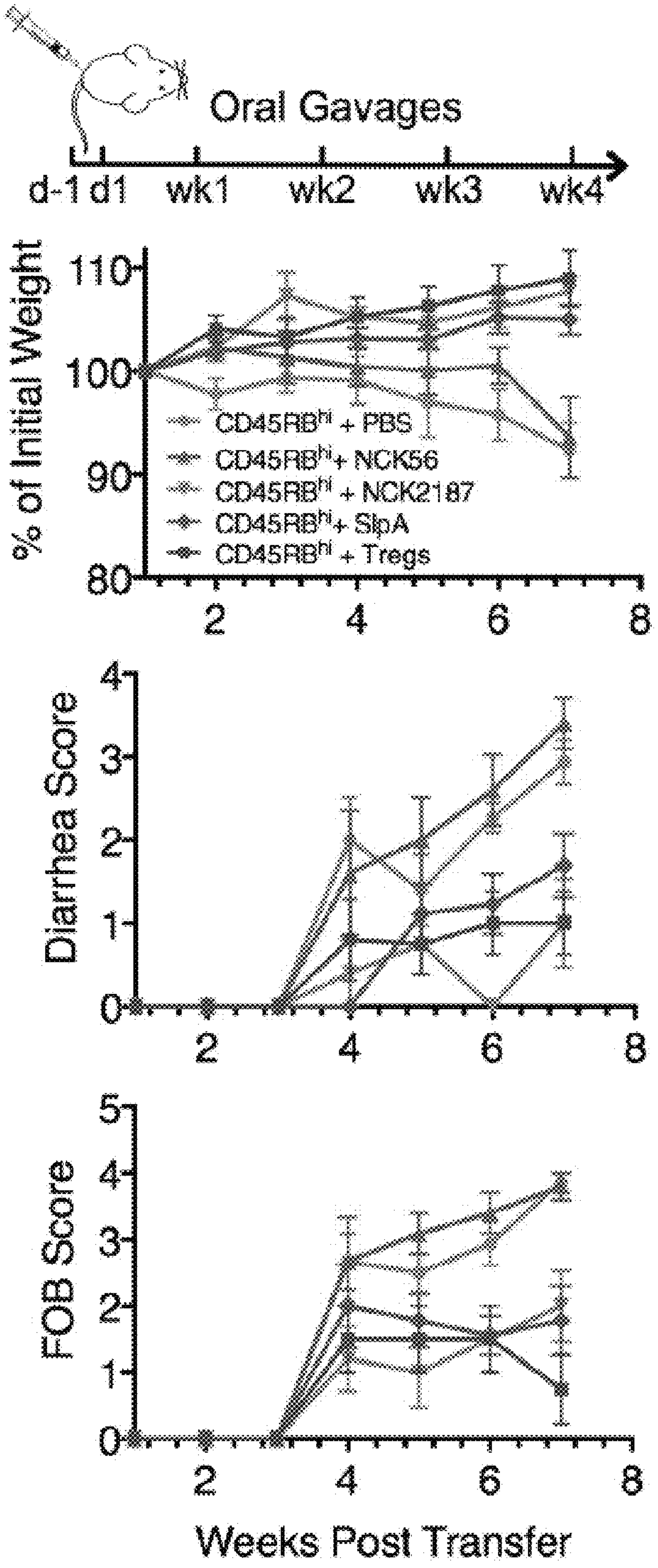
FIGS. 3A-3D. *L. acidophilus* NCK2187 and its SlpA protect against pathogenic T-cell induced colitis. $Rag1^{-/-}$ mice were injected with $10^6$ $CD4^+CD45RB^{hi}$ T cells, and then orally gavaged with NCK56 (red), NCK2187 (green), or SlpA (blue), 1 and 3 days after transfer, and subsequently once a week for 4 consecutive weeks, or left untreated (magenta). A group of mice was co-transferred with $CD4^+$ $CD25^+$ T cells as a positive control for protection (Tregs; gray). Colitis severity was determined in part by weight loss, diarrhea scores, and FOB (A). (See Tables 2-4 for statistical analyses results.) B-C. Colitis scores based on histopathology and gross morphology of the colons were also used as measures of disease. Scale bar=200 μm. D. Circulating levels of proinflammatory cytokines were measured in the sera of the mice transferred and treated as mentioned above, or sham adoptive transferred (white bars). n=5 mice/group. Data represent three individual experiments and are shown as mean±SEM. *P<0.05, P<0.01, *P<0.001, ****P<0.0001. Black asterisks compare NCK2187 to PBS-treated adoptively transferred mice, and red asterisks to NCK56-treated mice.

In preparation for the adoptive transfer of $CD45RB^{hi}$ $CD4^+$ T cells into $Rag1^{-/-}$ mice, spleen and mesenteric lymph node (MLN) single cell suspensions obtained from healthy B6 mice were pooled and incubated in AffiniPure Goat Anti-Mouse IgG (H+L)-coated cell culture plates (Jackson ImmunoResearch Laboratories, Inc., West Grove, Pa.) at 37° C. for 1 h. $CD4^+$ T cells were isolated from non-adherent cells using the $CD4^+$ T cell Isolation Kit II (MACS, Miltenyi Biotec, San Diego, Calif.), and $CD25^+$ $CD4^+$ T cells were then depleted by positive selection (MACS, Miltenyi Biotec). Bound $CD25^+$ $CD4^+$ T cells were collected and injected into the regulatory T cells (Tregs) group. The resulting cell suspensions after negative and positive selection was consistently comprised of >98% $CD25^-$ $CD45RB^{hi}$ $CD4^+$ T cells. $Rag1^{-/-}$ mice were orally gavaged once with NCK56, NCK2187, or SlpA prior to the adoptive transfer of T cells by intraperitoneal injection (i.p.). One day later, the mice were orally gavaged once more, and once a week for 4 consecutive weeks thereafter (FIG. 3A). Colitis progression was monitored by determining mouse weight loss, diarrhea development, and fecal occult blood (FOB) presence throughout the study. Stool consistency was scored as follows: 0=normal, 2=pasty, 4=watery with perianal staining.

DSS-Induced Colitis

WT and $Signr3^{-/-}$ mice were treated with 3% DSS in the drinking water for 5 days (made fresh every 2-3 days) to induce colitis. Mice were monitored for disease progression through day 10 after treatment as described above. For prevention studies, mice were orally gavaged with NCK56, NCK2187, or SlpA at days −3 and −1, then every other day after 3% DSS treatment, for a total of 5 gavages (2 before, and 3 after 3% DSS).

Histopathology

Colitis scores in T cell- and DSS-induced colitis were determined by histopathology. Tissues were fixed, sectioned, and stained with hematoxylin and eosin (Histology Tech Services, Gainesville, Fla.). Stained sections were analyzed blindly by a boarded veterinary pathologist. Colitis was graded based on 7 parameters (0-17) as previously described (Cheng et al., 2014).

FITC-Dextran Intestinal Permeability Assay

Passive transepithelial absorption of FITC-labeled dextran (Sigma-Aldrich) in vivo was used to determine intestinal barrier function as previously described (Napolitano et al., 1996). Mice were gavaged with FITC-dextran, MW 4,000 (60 mg/100 g body weight). Blood was collected retro-orbitally after proper anesthetization; mice were sacrificed after blood collection. Fluorescence intensity in the serum was measured with a fluorimeter (485 nm excitation, 519 nm emission). FITC-dextran concentrations in the mouse sera were determined from standard curves generated by serial dilution of FITC-dextran using blank subtraction in the test samples using sera from mice that were not gavaged with the permeability tracer.

Colonoscopy of DSS- and T Cell-Induced Colitis Mice

Macroscopic damage in the colons of $Rag1^{-/-}$, WT, and $Signr3^{-/-}$ mice was visualized with a Multi-Purpose Rigid Telescope attached to a TELE PACK X (Karl Storz-Endoscope, Germany). Mice were fasted for 2-4 h, and subsequently the colons of the living subjects were imaged under appropriate anesthetic conditions.

Real-Time PCR and 16S Ribosomal DNA Sequencing

Colonic tissues from $Rag1^{-/-}$, WT, and $Signr3^{-/-}$ mice were isolated and processed for changes in gene expression as previously described (Lightfoot et al., 2014). Microbiome analyses were performed on the Illumina Miseq (Illumina, Inc., San Diego) as outlined previously (Lightfoot et al., 2014). Primers used, as well as their sequences, are listed in the Table 1 below showing the list of primer sequences for Real-Time PCR analyses.

TABLE 1

List of primer sequences for Real-Time PCR analyses

| Gene name | Sequence (5'-3') | SEQ ID NO: |
|---|---|---|
| 111b | Forward AAGGAGAACCAAGCAACGAC | 5 |
| | Reverse GAGATTGAGCTGTCTGCTCA | 6 |
| Ocln | Forward GCTGTGATGTGTGTGAGCTG | 7 |
| | Reverse GACGGTCTACCTGGAGGAAC | 8 |
| Cd209a | Forward TCTGGA TTCAGT AGCTTCACAGG | 9 |
| | Reverse GGGTCAGTTCTTGGT AGACA TTC | 10 |
| Cd209b | Forward TTGA TGGTCAGCGGCAGCAGG | 11 |
| | Reverse TCAGCAGGAGCCCAGCCAAGA | 12 |
| Cd209c | Forward CTGGAATGACTCTGTCAATGCC | 13 |
| | Reverse GCCA TCTGCCTTCA TGCTTCA | 14 |
| Cd209d | Forward GGGCCCAACTGGTCATCATA | 15 |
| | Reverse AGCGTGTAAAGCTGGGTGAC | 16 |
| Cd209e | Forward CCACA TTCCCCTGGTGTTG | 17 |
| | Reverse CAGAGGCGACAGAGTCTATCA | 18 |
| Cd209f | Forward CTCTTTGGGCCTCTTTTTGCT | 19 |
| | Reverse AGTATGCACGAATCCTGGAGA | 20 |
| Cd209g | Forward GGCCTCAGCGATCACAGAAG | 21 |
| | Reverse ACAACGGCTGTCATTCCATTTA | 22 |

TABLE 1-continued

List of primer sequences for Real-Time PCR analyses

| Gene name | Sequence (5'-3') | SEQ ID NO: |
|---|---|---|
| Muc2 | Forward GTGTGGGACCTGACAATGTG | 23 |
| | Reverse ACAACGAGGTAGGTGCCATC | 24 |
| Muc3 | Forward GCCGTGAATTGTATGAACGGA | 25 |
| | Reverse CGCAGTTGACCACGTTGACT A | 26 |
| Tjp1 | Forward AGGACACCAAAGCATGTGAG | 27 |
| | Reverse GGCATTCCTGCTGGTT ACA | 28 |
| Tjp2 | Forward ATGGGAGCAGTACACCGTGA | 29 |
| | Reverse TGACCACCCTGTCA TTTTCTTG | 30 |
| Tjp3 | Forward TCGGCATAGCTGTCTCTGGA | 31 |
| | Reverse GTTGGCTGTTTTGGTGCAGG | 32 |
| Cldn1 | Forward TCCTTGTTCGGCTATGTGTC | 33 |
| | Reverse GGCATGCACCTAAGAATCAG | 34 |
| Cldn2 | Forward GGCTGTTAGGCACATCCAT | 35 |
| | Reverse TGGCACCAACATAGGAACTC | 36 |
| Cldn3 | Forward AAGCCGAATGGACAAAGAA | 37 |
| | Reverse CTGGCAAGTAGCTGCAGTG | 38 |
| Cldn5 | Forward GCAAGGTGTATGAATCTGTGCT | 39 |
| | Reverse GTCAAGGT AACAAAGAGTGCCA | 40 |
| Cldn8 | Forward GCCGGAATCA TCTTCTTCA T | 41 |
| | Reverse CA TCCACCAGTGGGTTGT AG | 42 |
| Hsp25 | Forward GGTTGCCCGATGAGTGGTC | 43 |
| | Reverse CTGAGCTGTCGGTTGAGCG | 44 |
| Hsp72 | Forward CTCCCTCTTGCGTTGCCTC | 45 |
| | Forward ACCCGCAGT AAT AGCCA TCTG | 46 |

SIGNR1 and SIGNR3 Binding Assays

C-type lectin receptors, SIGNR1 and SIGNR3, were fused to the Fc part of human IgG1 (SIGNR1-hFc and SIGNR3-hFc) as previously described (Eriksson et al., 2013). Briefly, the extracellular regions of murine SIGNR1 and SIGNR3 were amplified and ligated into the expression vector pFUSE-hIgG1-Fc2 (Invivogen, Toulouse, France) for expression in CHO-S cells. Expression in CHO cells was driven by an hEF1-HTLV promoter and secretion into the culture supernatant was mediated by an external IL2 signal sequence (IL2ss). Binding of SlpA-coated beads (Dynabeads MyOne Carboxylic Acid, Life Technologies) to fusion proteins was analyzed by flow cytometry.

Statistical Analyses

Representative data indicate mean±SEM. Significance was determined by two-tailed unpaired t-tests for two group comparisons (GraphPad Prism v6.0d for Mac OS X, La Jolla, Calif.). Statistical significance for differences in weight loss, diarrhea score, and FOB score was calculated using multiple unpaired t-tests correcting for multiple comparisons with the Holm-Sidak method in Prism v6.0d.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—NCK2187 Promotes Intestinal Immune Regulation in Steady-State

Figure 1A:
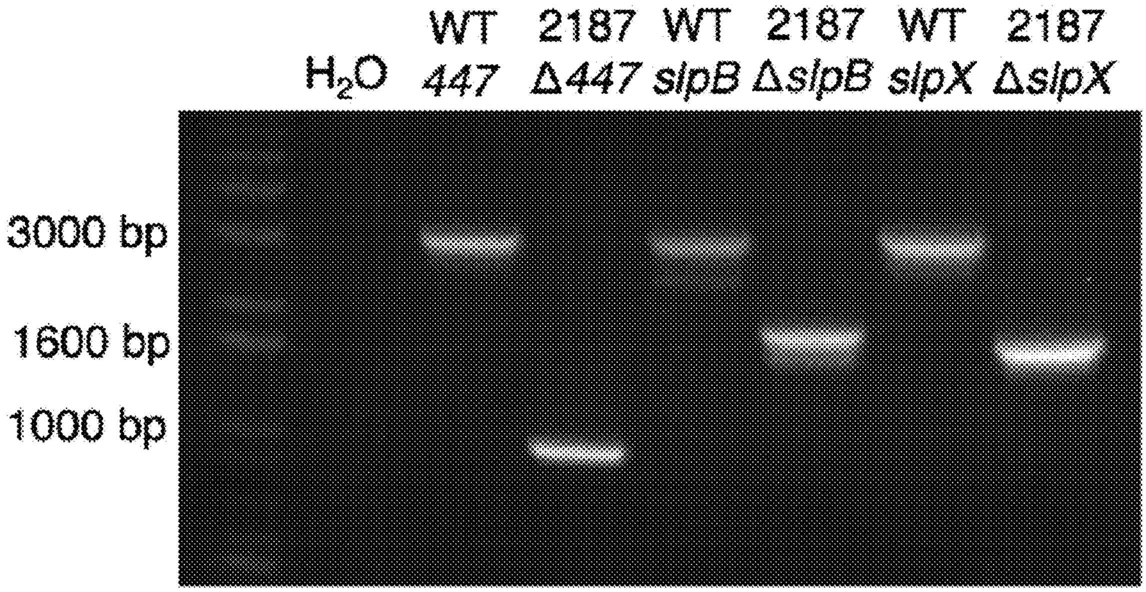
FIGS. 1A-1E. *L. acidophilus* NCK2187 strain development and characteristics. A. Agarose gel image illustrating PCR amplicons of ltaS (LBA0447), slpB, and slpX deletions in NCK2187. B. SDS-PAGE gel of 5 M LiCl-purified S-layer fractions from the parental strains, NCK56 and NCK1909; NCK2030 ($LTA^+$, $SlpA^+$, $SlpB^-$, $SlpX^-$); and NCK2187 ($LTA^-$, $SlpA^+$, $SlpB^-$, $SlpX^-$). C. Protein gel showing predominance of SlpA in NCK2187 and absence of other Slps. D. B6 mice were orally gavaged with $10^9$ CFU erythromycin-resistant NCK56 or NCK2187. Fecal pellets were collected daily and tested for the presence of erythromycin-resistant strains. n=3 mice/group. Data are representative of five independent experiments and are shown as mean±SEM. E. Colonic LP cells were co-cultured with NCK56 or NCK2187 (1:1) and secreted cytokines were measured in the supernatants. Data are shown as mean±SEM. *P<0.05, P<0.01, *P<0.001.
Figure 1B:
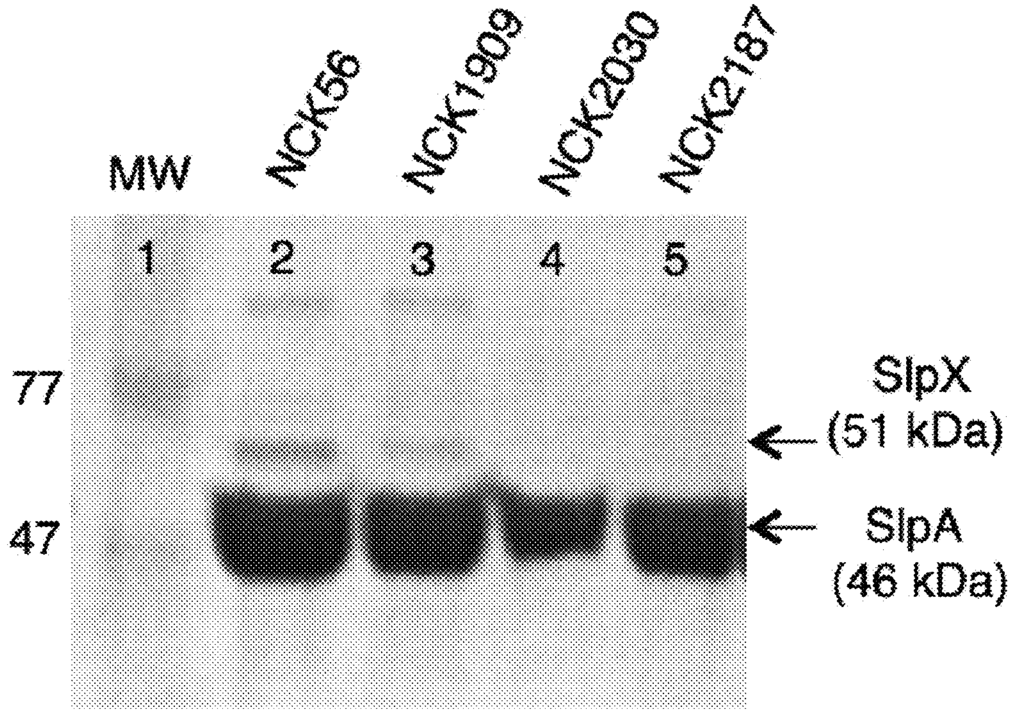
Figure 1C:
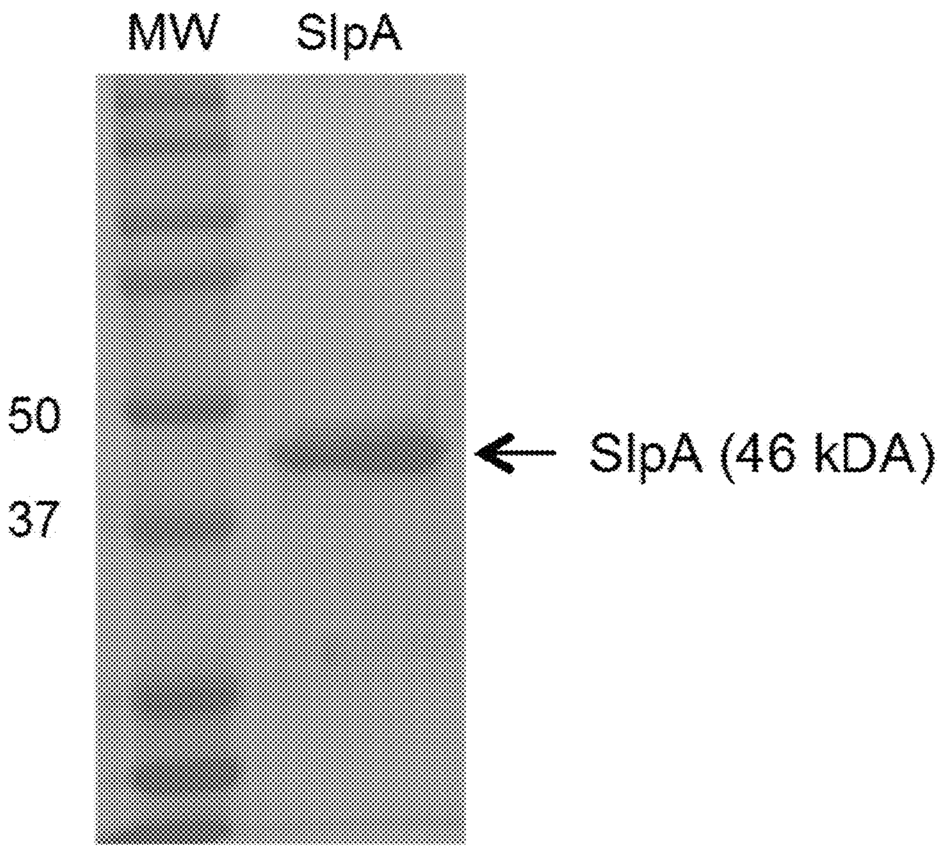

Transient colonization of the colon with NCK2025 ($LTA^-$) significantly mitigated chemical and T cell-mediated colitis (Mohamadzadeh et al., 2011). Additionally, NCK2025 significantly abated inflammation-promoting polyposis in $Apc^{lox468}$xTS4-Cre mouse model, where protection correlated with the regulation of innate and T cell-induced inflammation (Khazaie et al., 2012). Thus, the controlled inflammation may result from the crosstalk between NCK2025-SlpA and intestinal cells. To test this hypothesis, the upp-counterselective gene replacement strategy was used to generate in-frame deletions in the slpB and slpX genes of NCK2030. The $LTA^-$ derivative was created by a deletion of the phosphoglycerol transferase gene (Mohamadzadeh et al., 2011) in NCK2030, resulting in NCK2187, which expresses only SlpA (FIGS. 1A-C).

Figure 1D:
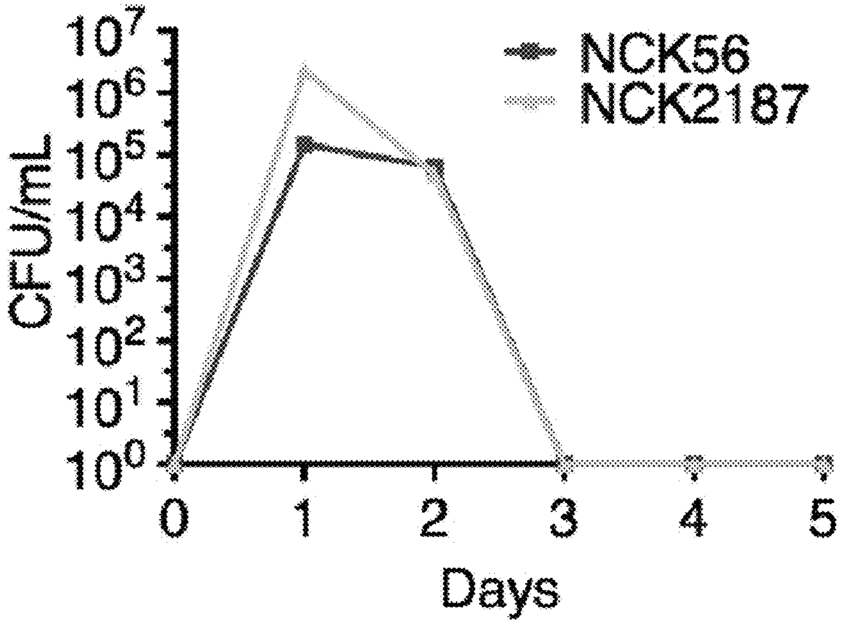

To demonstrate that the newly generated NCK2187 transiently colonizes the gut, the clearance kinetics of both the erythromycin-resistant NCK56 and NCK2187 strains were determined in C57BL/6 (B6) mice that were orally treated once with $10^9$ CFU/mouse. Data show that mice cleared both NCK56 and NCK2187 after 3 days, indicating that the deletion of LTA, SlpB, and SlpX in NCK2187 did not alter its transient passage through the GI tract when compared to its WT parent (FIG. 1D).

Figure 1E:
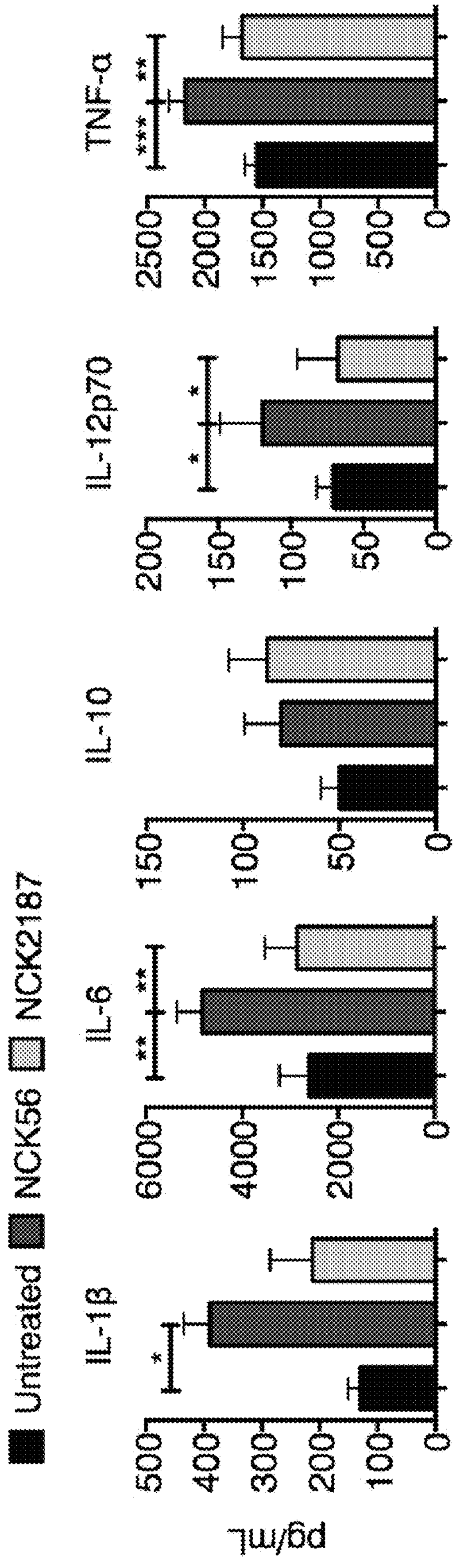

To investigate the activation of colonic DCs when co-cultured with NCK56 or NCK2187, colonic cells were obtained from naïve B6 mice. While such intestinal cell-bacterial co-cultures did not significantly change the expression of DC costimulatory molecules (e.g., CD40) (not shown) or IL-10, only NCK56 elevated the levels of IL-1β, IL-6, IL-12, and TNF-α (FIG. 1E).

Figure 2A:
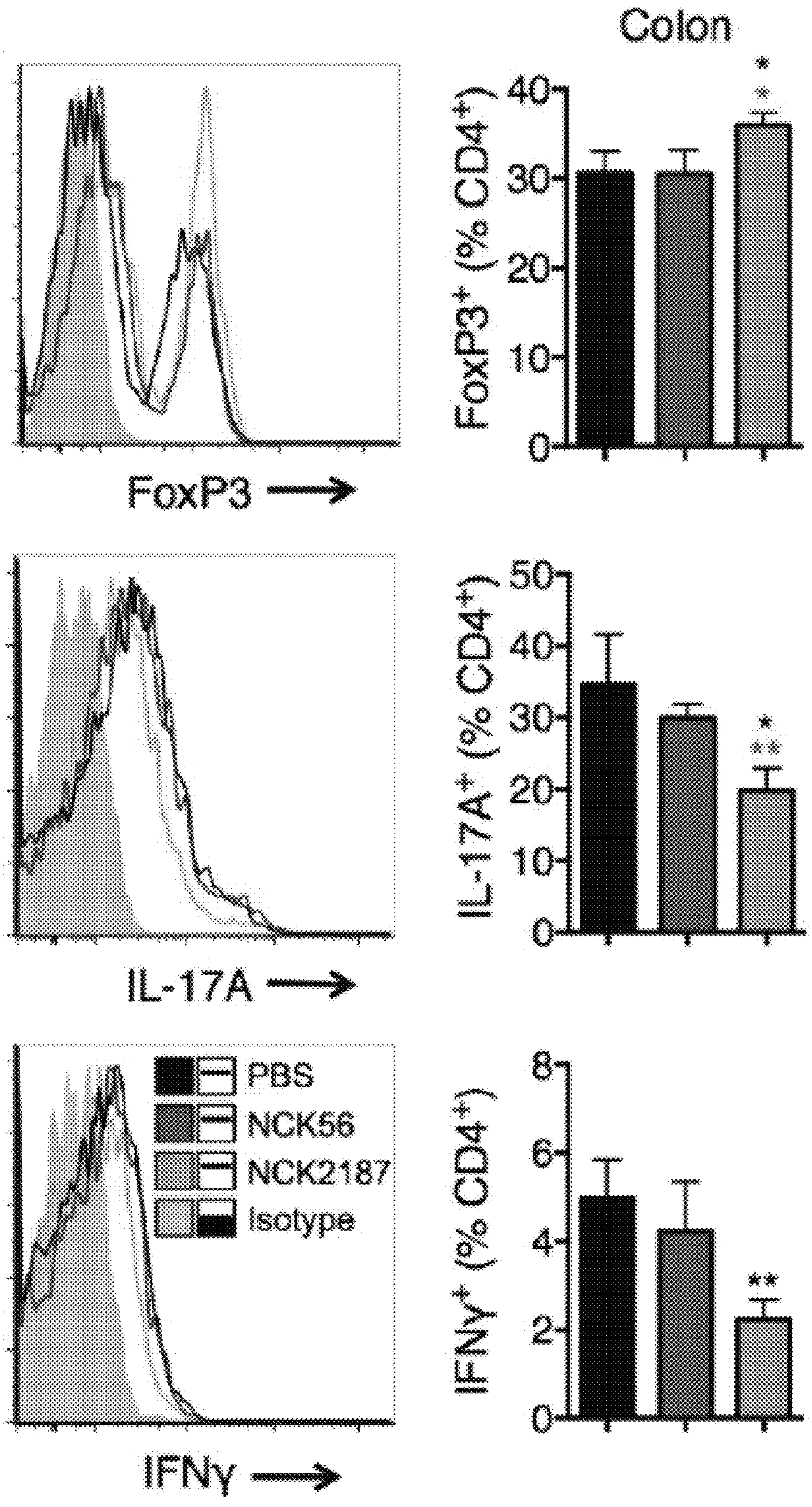
FIGS. 2A-2C. *L. acidophilus* NCK2187 promotes intestinal regulation in steady-state. A. B6 mice were orally gavaged with $10^9$ CFU NCK56 (blue) or NCK2187 (green) on days 0, 3, 6, and 9, or left untreated, and immune responses in the colon analyzed at day 14 by flow cytometry. B-C. FoxP3-GFP mice were treated and evaluated as in (A). C. Regulatory cytokine production in FoxP3-$GFP^+$ (green dotted bars) versus FoxP3-$GFP^-$ (white bars) cells was measured by intracellular staining and FACS analyses. n=5 mice/group. Data represent four individual experiments and are shown as mean±SEM. *P<0.05, P<0.01, *P<0.001, ****P<0.0001. Black asterisks compare NCK2187 to untreated (PBS) mice, and red asterisks to NCK56-treated mice.
Figure 2B:
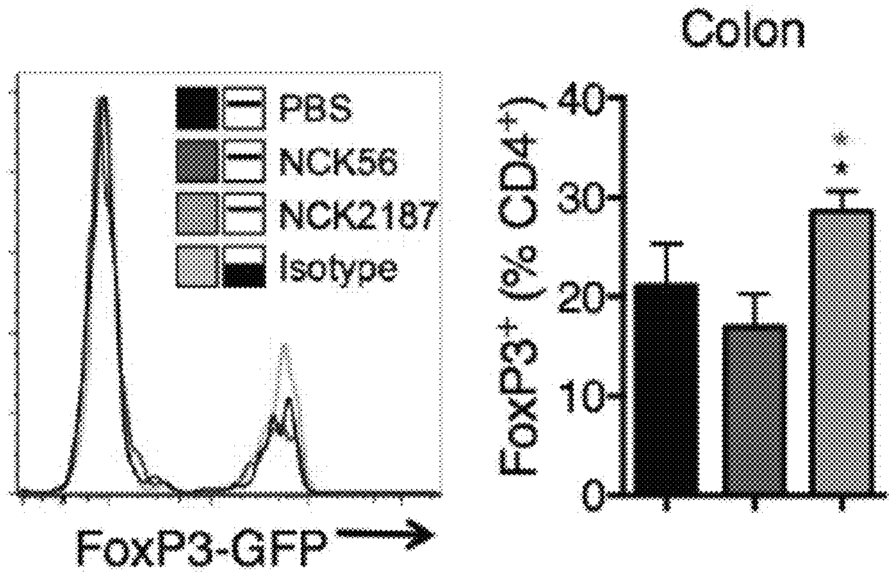
Figure 2C:
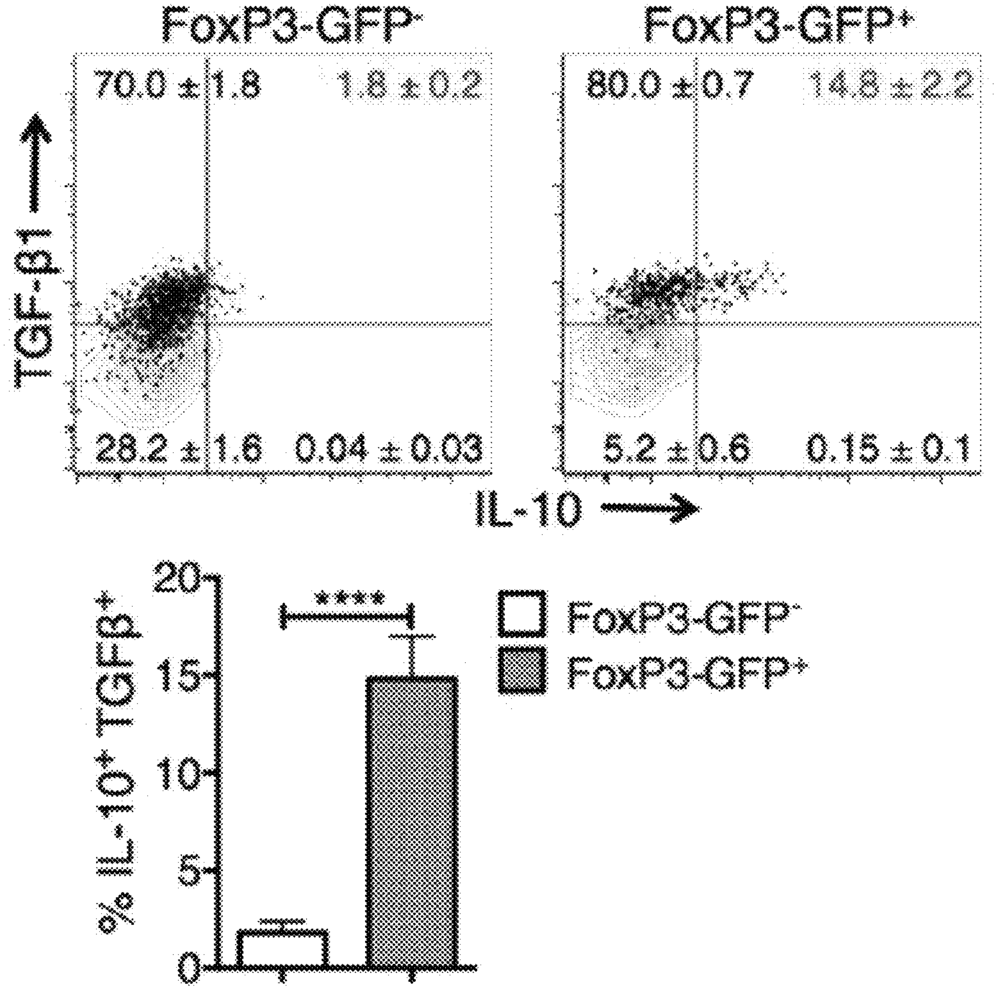

Next, naïve mice were orally gavaged with NCK56 or NCK2187 and colonic immune responses analyzed. Treatment with NCK2187 significantly increased the frequency of colonic $FoxP3^+$ Tregs when compared to both untreated (PBS) and NCK56-treated mice (FIG. 2A). Moreover, $IL\text{-}17A^+$ and $IFN\gamma^+$ $CD4^+$ T cells were significantly reduced by NCK2187 treatment (FIG. 2A). NCK2187-treated FoxP3-GFP mice also exhibited higher numbers of colonic $IL\text{-}10^+$ $TGF\text{-}\beta 1^+$ Tregs than NCK56-treated and untreated mice (FIGS. 2B, 2C). Collectively, oral treatment with this novel *L. acidophilus* strain induced colonic regulatory immune responses.

Figure 3B:
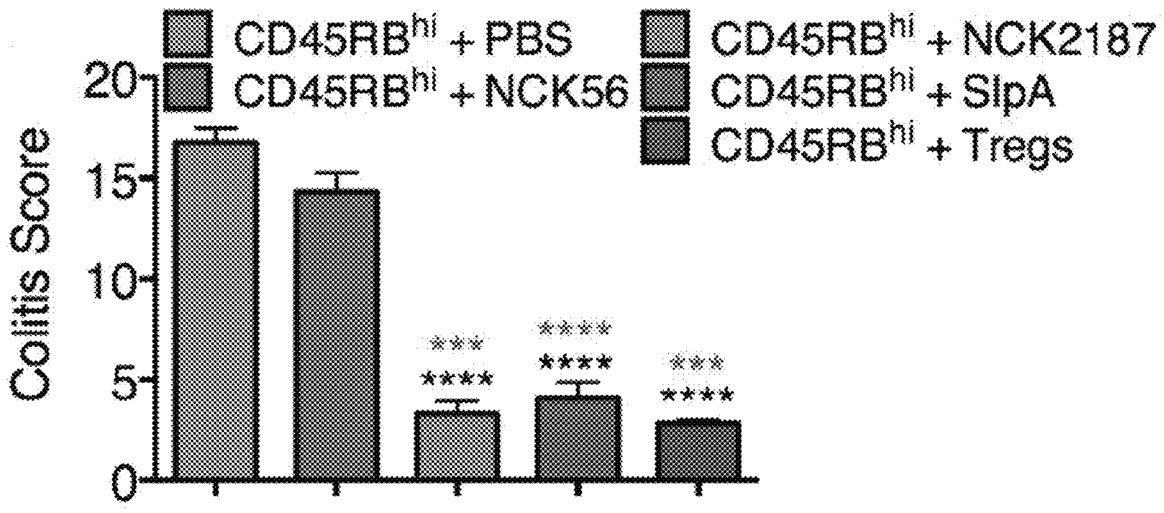
Figure 3C:
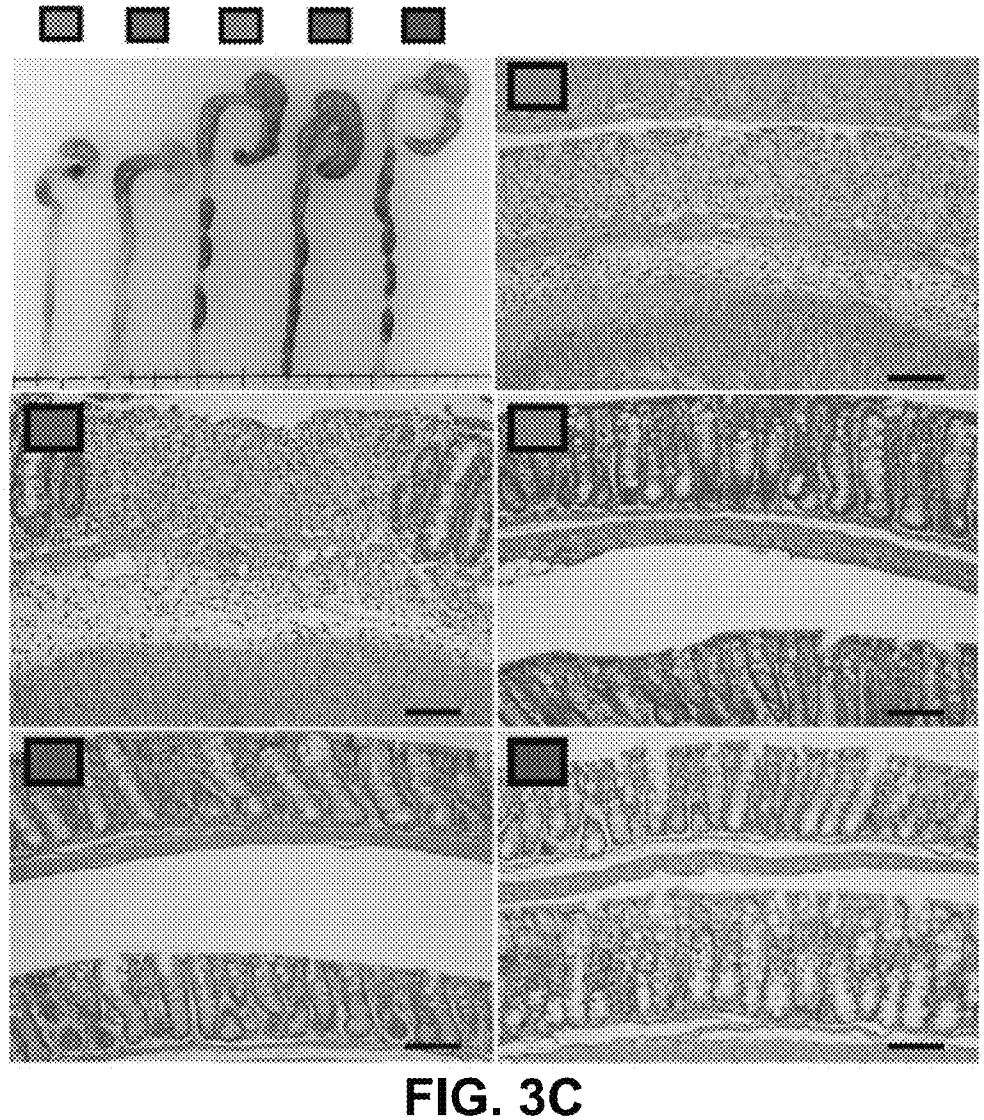
Figure 3D:
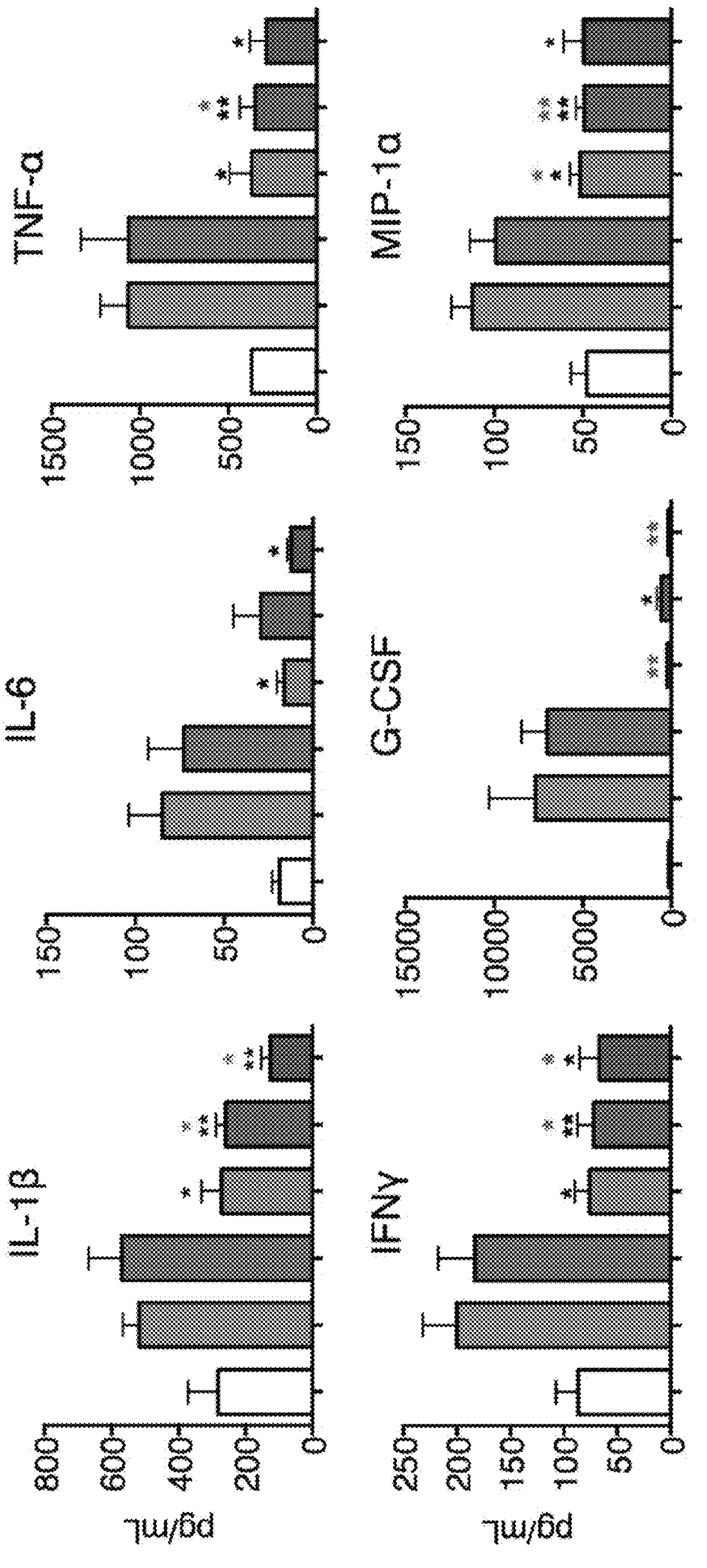

Example 2—Protective Property of NCK2187 and its SlpA Against Inflammation and Dysbiosis To elucidate the consequences of the immunoregulatory responses observed above during inflammation, $Rag1^{-/-}$ mice adoptively transferred with $CD45RB^{hi}$ $CD4^+$ T cells were orally treated with NCK56, NCK2187, its purified SlpA, or PBS (FIG. 3A). Untreated (PBS) and NCK56-treated mice with adoptively transferred T cells developed severe colitis as demonstrated by weight loss, bloody diarrhea, shortening of the colon, and increased damage of the colon (FIGS. 3A-C, FIG. 8A). Furthermore, the levels of systemically induced proinflammatory IL-1β, IL-6, TNF-α, IFNγ, G-CSF, and MIP-1α were significantly enhanced in the sera of these groups of mice (FIG. 3D). In contrast, similar to the Treg co-transferred mice, NCK2187 and its purified SlpA significantly protected $Rag1^{-/-}$ mice from T cell-induced colitis (Tables 2-4).

TABLE 2

Statistical analysis of weight loss curves in T cell-induced colitis.

| | Weight Loss (p-value) | | | | | |
|---|---|---|---|---|---|---|
| | vs. + PBS | | | vs. + NCK56 | | |
| Week | +Tregs | +NCK2187 | +SlpA | +Tregs | +NCK2187 | +SlpA |
| 1 | 1.0 | 1.0 | 1.0 | 1.0 | 1.0 | 1.0 |
| 2 | 0.0601 | 0.1714 | 0.1224 | 0.5588 | 0.9927 | 0.8543 |
| 3 | 0.2331 | 0.0237 | 0.1943 | 0.5119 | 0.0556 | 0.5386 |
| 4 | 0.0653 | 0.0778 | 0.1229 | 0.1194 | 0.1220 | 0.2526 |

TABLE 3

Statistical analysis of diarrhea score curves in T cell-induced colitis.

| | Diarrhea Score (p-value) | | | | | |
|---|---|---|---|---|---|---|
| | vs. + PBS | | | vs. + NCK56 | | |
| Week | +Tregs | +NCK2187 | +SlpA | +Tregs | +NCK2187 | +SlpA |
| 1 | 1.0 | 1.0 | 1.0 | 1.0 | 1.0 | 1.0 |
| 2 | 1.0 | 1.0 | 1.0 | 1.0 | 1.0 | 1.0 |
| 3 | 1.0 | 1.0 | 1.0 | 1.0 | 1.0 | 1.0 |
| 4 | 0.0231 | 0.0024 | 0.0014 | 0.2100 | 0.0592 | 0.0287 |
| 5 | 0.1139 | 0.1100 | 0.507225 | 0.0101 | 0.0094 | 0.0749 |
| 6 | 0.0011 | <0.0001 | 0.0046 | 0.0011 | <0.0001 | 0.0031 |
| 7 | <0.0001 | <0.0001 | 0.0008 | <0.0001 | <0.0001 | 0.0003 |

TABLE 4

Statistical analysis of fecal occult blood (FOB) score curves in T cell induced colitis.

| | FOB Score (p-value) | | | | | |
|---|---|---|---|---|---|---|
| | vs. + PBS | | | vs. + NCK56 | | |
| Week | +Tregs | +NCK2187 | +SlpA | +Tregs | +NCK2187 | +SlpA |
| 1 | 1.0 | 1.0 | 1.0 | 1.0 | 1.0 | 1.0 |
| 2 | 1.0 | 1.0 | 1.0 | 1.0 | 1.0 | 1.0 |
| 3 | 1.0 | 1.0 | 1.0 | 1.0 | 1.0 | 1.0 |
| 4 | 0.0730 | 0.0176 | 0.2532 | 0.0721 | 0.0175 | 0.2479 |
| 5 | 0.0227 | 0.0008 | 0.0733 | 0.0009 | <0.0001 | 0.0027 |
| 6 | 0.0014 | 0.0015 | 0.0009 | 0.0001 | 0.0001 | <0.0001 |
| 7 | <0.0001 | <0.0001 | <0.0001 | <0.0001 | 0.0003 | <0.0001 |

NCK2187- and SlpA-treated mice gained weight throughout the course of the study and did not develop significant bloody diarrhea in the way that the PBS and NCK56 groups did (FIG. 3A). Furthermore, cecal and colonic atrophy due to pathogenic inflammation was not observed in these mice, as the tissue destruction and immune cell infiltration associated with T cell-induced colitis were significantly abrogated in NCK2187 and SlpA treated groups (FIGS. 3B and 3C). Accordingly, systemic inflammation was significantly reduced in these groups of mice (FIG. 3D).

Figure 8A:
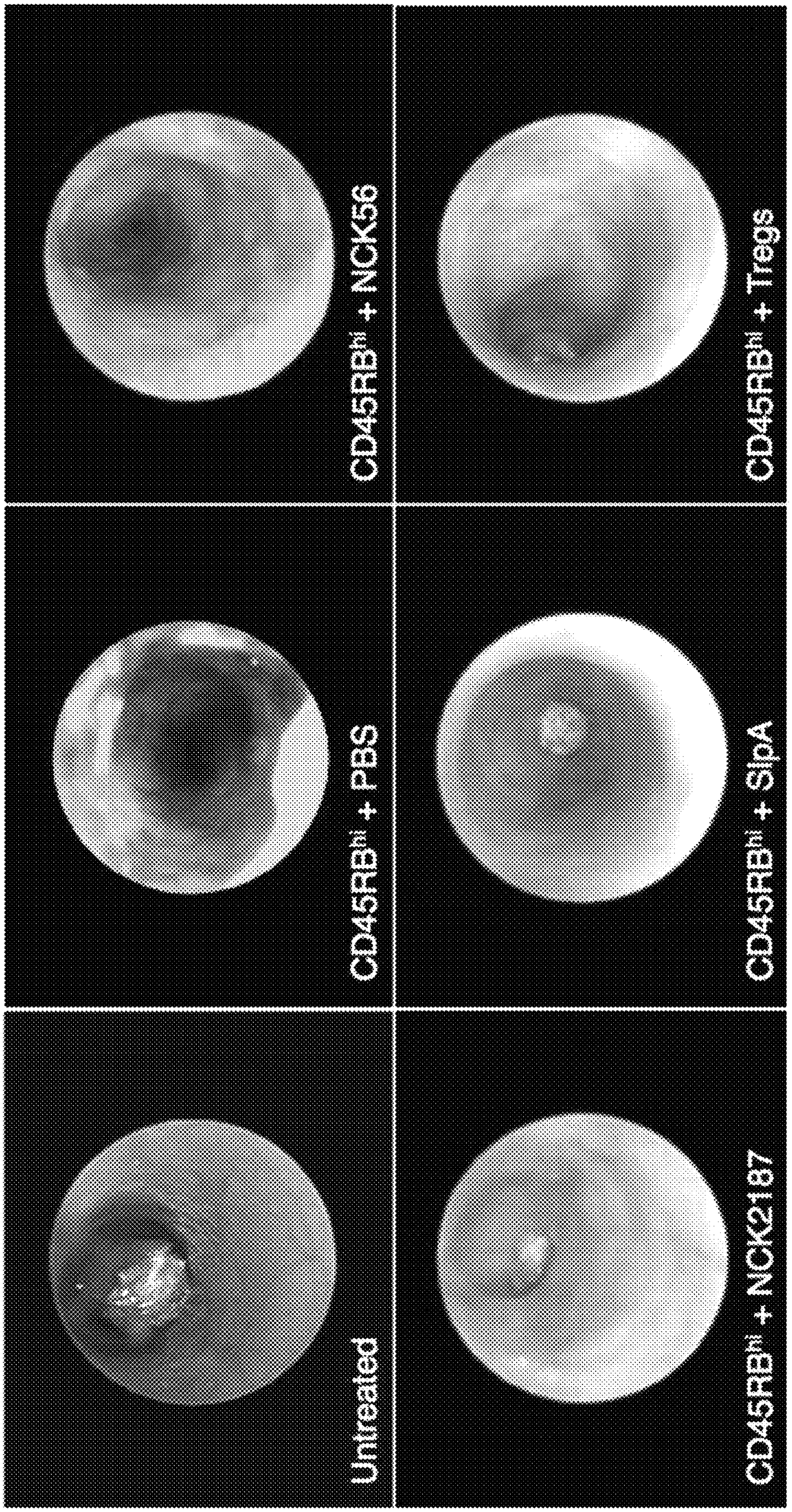
FIGS. 8A-8B. *L. acidophilus* NCK2187 and its SlpA in pathogenic T-cell induced colitis. $Rag1^{-/-}$ mice were injected with $10^6$ CD4+CD45RBhi T cells, and then orally gavaged with NCK56 (red), NCK2187 (green), or SlpA (blue), 1 and 3 days after transfer, and subsequently once a week for 4 consecutive weeks, or left untreated (magenta). A group of mice was co-transferred with $CD4^+CD25^+$ T cells as a positive control for protection (Tregs; gray). A. Colonic expression of Ltb4r1, Ltb4r2, and Il1b were determined by RT-PCR. n=5 mice/group. Data represent three individual experiments and are shown as mean±SEM. *P<0.05, **P<0.01. Black asterisks compare NCK2187 to PBS-treated adoptively transferred mice, and red asterisks to NCK56-treated mice. B. Colonoscopies were performed in the specified groups with a Multi-Purpose Rigid™ Telescope attached to a TELEPACK X.
Figure 8B:
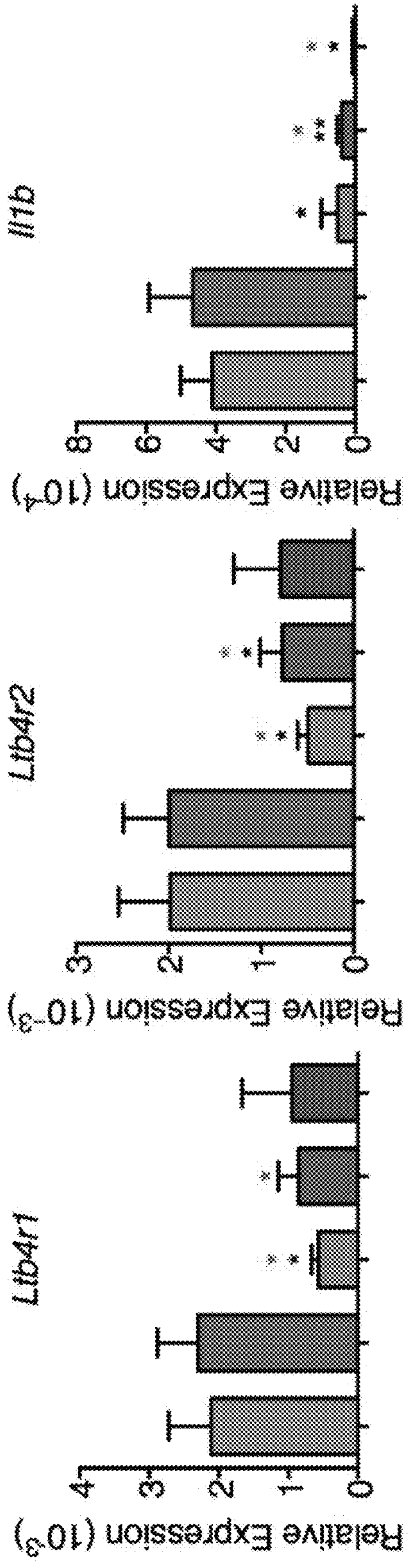

The genes encoding the receptors for $LTB_4$, Ltb4r1 and Ltb4r2 were significantly down-regulated in the colons of NCK2187- and SlpA-treated mice (FIG. 8B), which may have contributed to the reduced expression of colonic Il1b (FIG. 8B).

T cell-induced colitis resulted in intestinal epithelial erosions and ulcerations in mice that did not receive NCK2187 or purified SlpA (FIG. 3C). Indeed, the colonic expression of tight junction associated genes was significantly downregulated in PBS- and NCK56-treated $Rag1^{-/-}$ mice (FIG. 4A).

Figure 4A:
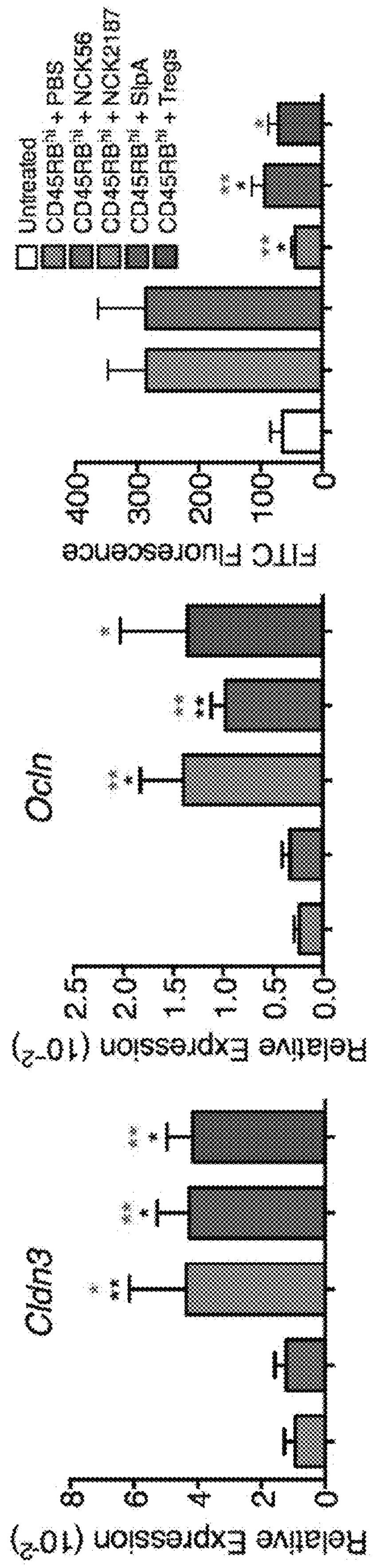
FIGS. 4A-4D. *L. acidophilus* NCK2187 and its SlpA protect intestinal barrier function and prevent dysbiosis in pathogenic T-cell induced colitis. $Rag1^{-/-}$ mice were injected with $10^6$ $CD4^+CD45RB^{hi}$ T cells, and then orally gavaged with NCK56 (red), NCK2187 (green), or SlpA (blue), 1 and 3 days after transfer, and subsequently once a week for 4 consecutive weeks, or left untreated (magenta). A group of mice was co-transferred with $CD4^+CD25^+$ T cells as a positive control for protection (Tregs; gray). A. Colonic expression of tight junction-associated genes Cldn3 and Ocln, determined by RT-PCR, as well as passive transepithelial absorption of FITC-dextran, were used as measures of epithelial barrier integrity. Sham adoptive transferred $Rag1^{-/-}$ mice (white bars) were used as baseline controls in some cases. n=5 mice/group. Data represent three individual experiments and are shown as mean±SEM. *P<0.05, **P<0.01. Black asterisks compare NCK2187 to PBS-treated adoptively transferred mice, and red asterisks to NCK56-treated mice. B. UniFrac analyses were used to calculate distances between the microbial communities of the different samples (week 7) and three-dimensional scatterplots were generated by using principal coordinate analyses (PCoA). Gray dots=$CD4^+CD45RB^{hi}$ T cells+PBS; yellow dots=$CD4^+CD45RB^{hi}$ T cells+NCK56; green dots=$CD4^+CD45RB^{hi}$ T cells+NCK2187; blue dots=$CD4^+$ $CD45RB^{hi}$ T cells+SlpA; red dots=$CD4^+CD45RB^{hi}$ T cells+ Tregs. Each dot represents the fecal microbiota data of an individual mouse. C. Changes in the relative abundance of different phyla were also analyzed. (See Table 5 for statistical analyses among the different groups.) Dark blue=Actinobacteria; green=Bacteroidetes; red=Proteobacteria; yellow=Verrucomicrobia; aqua=Firmicutes; purple=Tenericutes; black=Others. D. Comparison of microbial communities at family or order levels. The heat map depicts the relative value in individual mice. n=5-6 mice/group.
Figure 4B:
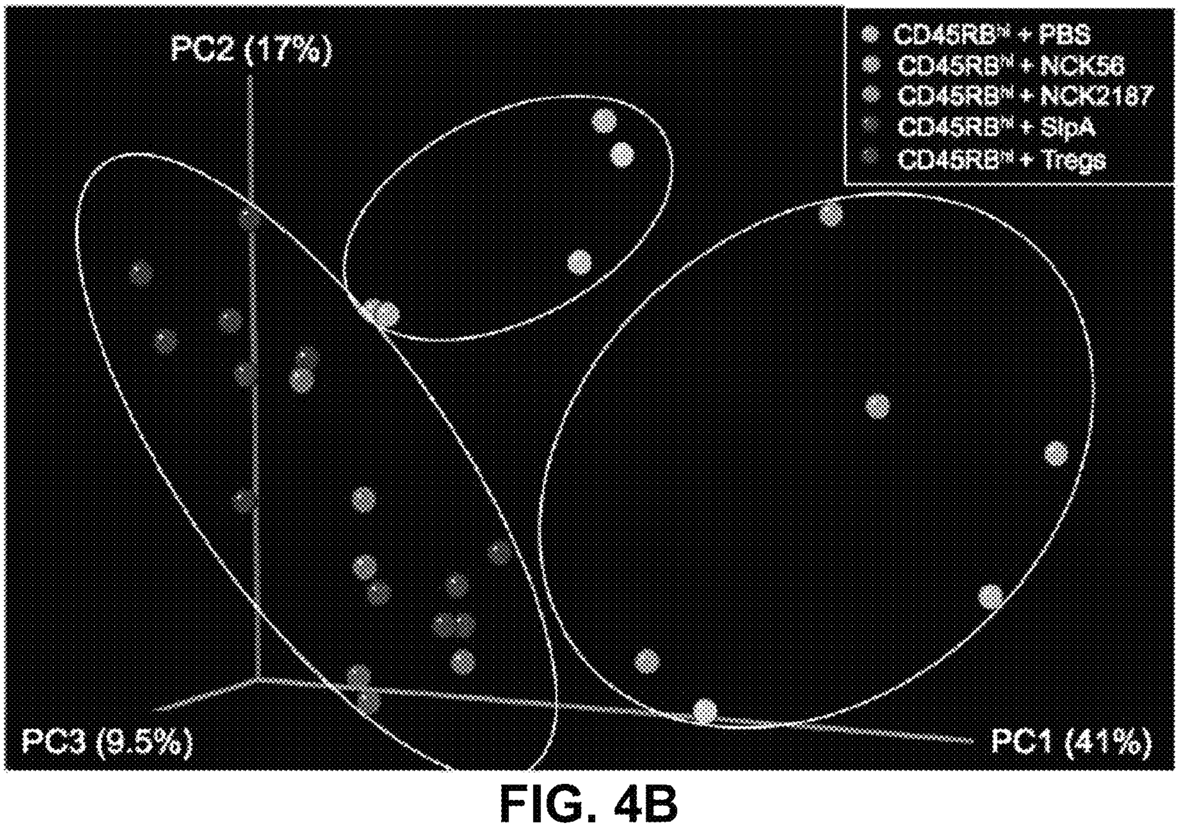
Figure 4C:
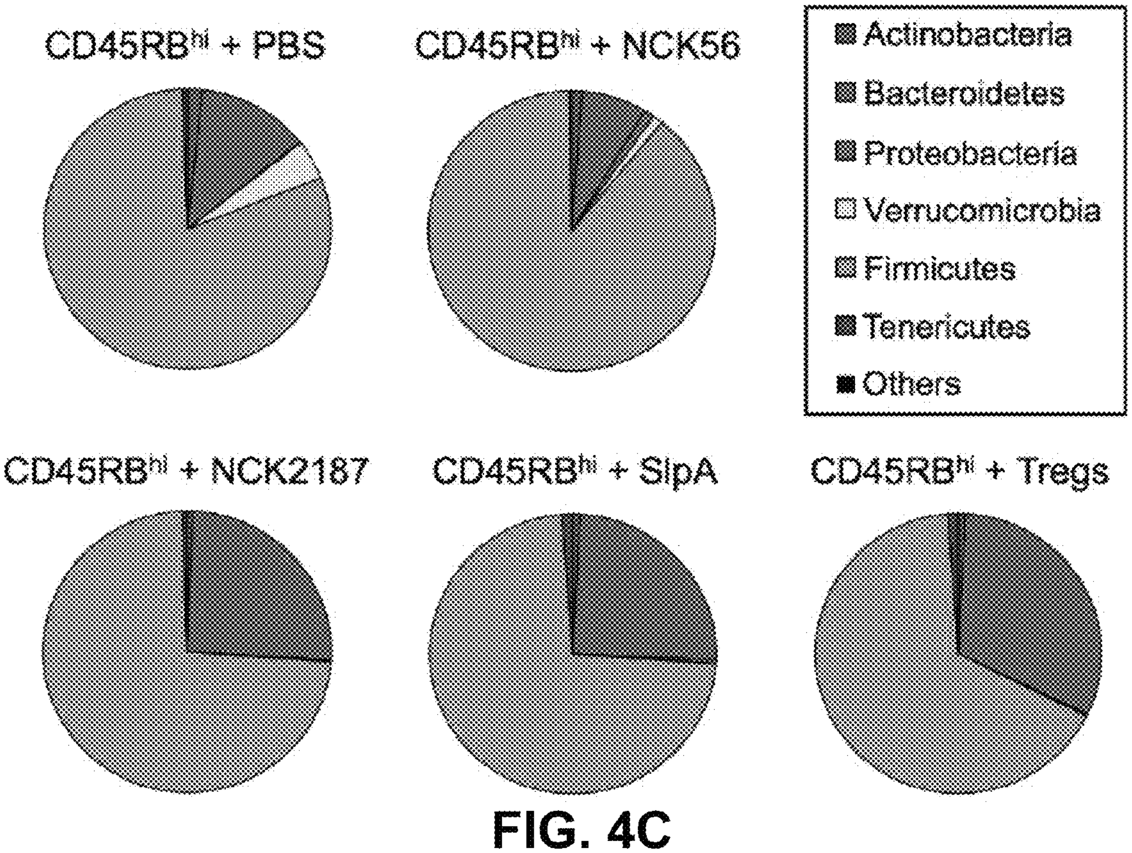
Figure 4D:
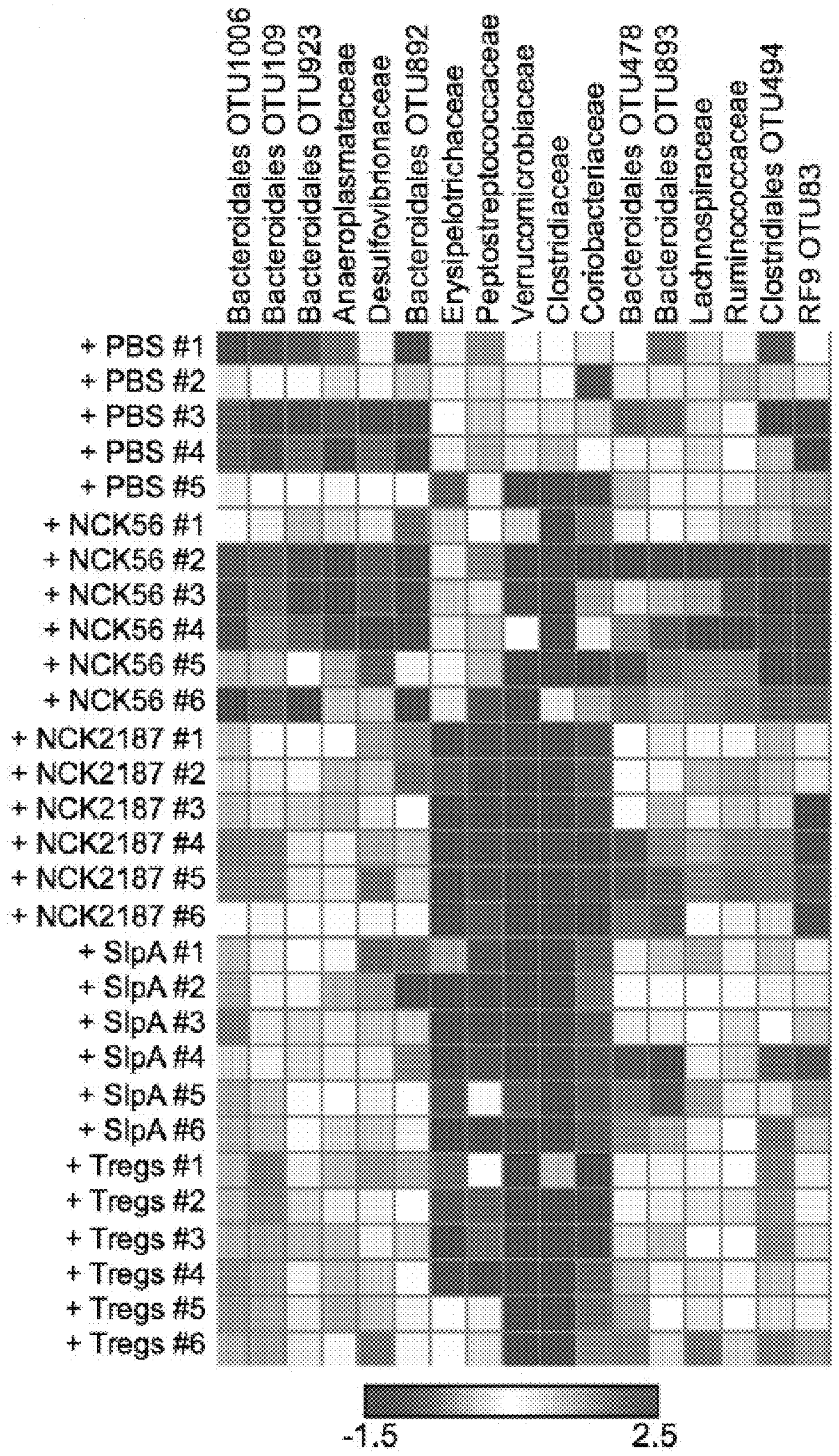

Furthermore, FITC-dextran permeability assays confirmed that these mice were suffering from a dysfunctional intestinal barrier (FIG. 4A). Accordingly, NCK2187 and SlpA significantly protected barrier integrity and function (FIG. 4A). An immunologically and anatomically weakened intestinal epithelial barrier during acute intestinal inflammation allows luminal bacteria to interact with the intestinal mucosae and the infiltrating immune cells, initiating inflammatory responses directed against the gut commensals and introducing dysbiosis. To elucidate the status and composition of the microbiota in the T cell-induced colitis model (week 7), we analyzed the microbial communities in the colons of the different experimental groups and found that the severity of colitis was associated with significant changes in the microbiota (FIGS. 4B-D, Table 5). UniFrac analyses revealed that fecal bacterial diversity in PBS- and NCK56 treated $Rag1^{-/-}$ mice was modified in such a way that these groups were found to cluster separately from each other and from the protected mice (FIG. 4B). Conversely, SlpA-, NCK2187-, and Treg-treated groups clustered together and showed similar phyla distributions (FIGS. 4B and 4C). Induced colitis in PBS- and NCK56-treated groups resulted in a significant contraction of members of the Bacteroidetes phyla (FIG. 4C). Additionally, the normally underrepresented Verrucomicrobia phyla was increased in these colitogenic mice (FIG. 4C), suggesting a shift in the intestinal milieu and the substrates available in the inflamed colon, which may promote previously underrepresented microbial communities so that they dominate the population. Alterations in the microbial composition were also manifested at lower taxonomic levels: NCK2187-, SlpA-, and Treg-treated groups once again showed similar relative abundance and distribution of several unclassified genera (FIG. 4D).

TABLE 5

Analysis of phyla distribution in the fecal microbiota after T cell-induced colitis.

| | p-value | | | | | | | | | | |
|---|---|---|---|---|---|---|---|---|---|---|---|
| | vs. + PBS | | | vs. + NCK56 | | | Mean Value (%) | | | | |
| Phylum | +Tregs | +NCK2187 | +SlpA | +Tregs | +NCK2187 | +SlpA | +PBS | +NCK56 | +Tregs | +NCK2187 | +SlpA |
| Actinobacteria | 0.1818 | 0.1595 | 0.1812 | 0.2663 | 0.2188 | 0.2654 | 1.64 | 1.16 | 0.79 | 0.62 | 0.80 |
| Bacteroidetes | 0.0010 | 0.0129 | 0.0276 | <0.0001 | 0.0009 | 0.0029 | 12.70 | 7.44 | 31.32 | 25.30 | 24.87 |
| Firmicutes | 0.0053 | 0.0714 | 0.1022 | <0.0001 | 0.0010 | 0.0043 | 80.43 | 88.89 | 66.45 | 73.35 | 72.61 |
| Proteobacteria | 0.2838 | 0.3294 | 0.0673 | 0.1508 | 0.1364 | 0.1956 | 0.14 | 1.15 | 0.26 | 0.21 | 0.42 |
| Tenericutes | 0.0494 | 0.4280 | 0.1102 | 0.0015 | 0.1215 | 0.0208 | 0.54 | 0.24 | 1.17 | 0.49 | 1.22 |
| Verrucomicrobia | 0.0244 | 0.0249 | 0.0263 | 0.0796 | 0.0834 | 0.0934 | 3.79 | 1.13 | 0.01 | 0.06 | 0.08 |

Figure 5A:
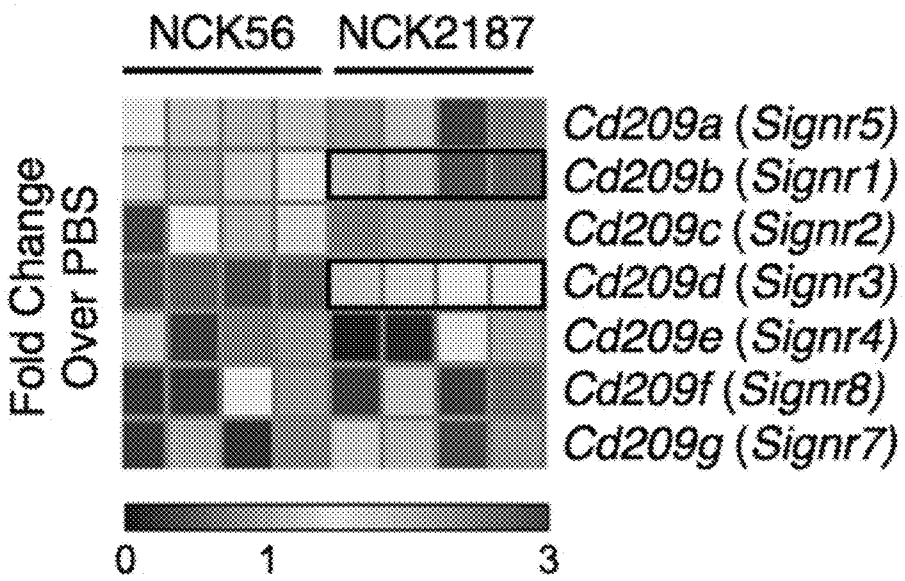
FIGS. 5A-5D. *L. acidophilus* NCK2187 and its SlpA bind to murine SIGNR3 to induce regulatory signals. A. B6 mice were orally gavaged with $10^9$ CFU NCK56 or NCK2187 and the colonic gene expression of C-type lectin receptors were measured by RT-PCR. Each box represents an individual mouse; n=4. Data represent three individual experiments and are shown as mean±SEM. B. Binding of SlpA to various hFc fusion proteins were analyzed by flow cytometry. Gray tinted line=SlpA-coated beads only; orange=SlpA-coated beads+secondary antibody; green=SlpA-coated beads+control fusion protein; blue=SlpA-coated beads+SIGNR1-hFc; red=SlpA-coated beads+SIGNR3-hFc. Binding assays results were confirmed five independent times. C. IL-β production by colonic DCs of naïve WT B6 GF or $Signr3^{-/-}$ mice treated with NCK56 (blue) or NCK2187 (green) on days 0, 3, 6, and 9, or left untreated (black), as determined by flow cytometry. D. Frequency of colonic $FoxP3^+$ Tregs in KO mice treated with NCK56 or NCK2187 was measured by flow cytometry. n=5 mice/group. Data represent four individual experiments and are shown as mean±SEM. *P<0.05. Black asterisks compare NCK2187 to untreated (PBS) mice, and red asterisks to NCK56-treated mice.

Example 3—L. *Acidophilus*-SlpA Binding to Signr3 Promotes Colonic Regulatory Immune Responses Symbiotic bacteria and their gene products dictate the nature of innate responses via their sensing receptors (Ivanov and Honda, 2012; Yang et al., 2014); however such stimulatory signals must be regulated by other receptors to avoid intestinal inflammation. As previously stated, SIGNR3 exhibits the most biochemical similarity to human DC-SIGN. We screened all known murine SIGNR1-8 and found that Signr1 and Signr3 genes are differentially activated in the colonic tissue of mice orally treated with NCK2187 (FIG. 5A), prompting us to evaluate the binding of SlpA to SIGNR1 and SIGNR3.

Figure 5B:
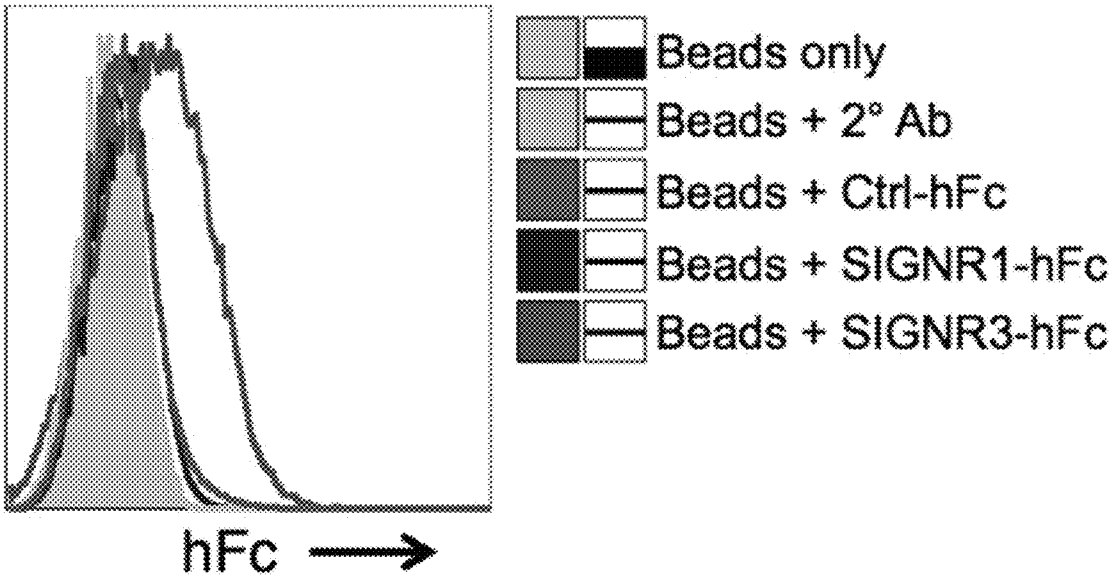

Subsequently, the corresponding extracellular domain of SIGNR1 and SIGNR3 were fused to the Fc portion of human $IgG_1$ (SIGNR1-hFc, SIGNR3-hFc) and then transiently expressed in Chinese hamster ovary (CHO)-S cells (data not shown). Data demonstrate that while expressed SIGNR3-hFc bound to purified SlpA coated onto charged beads, SIGNR1-hFc, DCAR-hFc (control protein), hFc, and the secondary rat anti-human Fc antibody alone did not, suggesting SlpA-binding specificity to SIGNR3 (FIG. 5B).

Figures 5C, 5D:
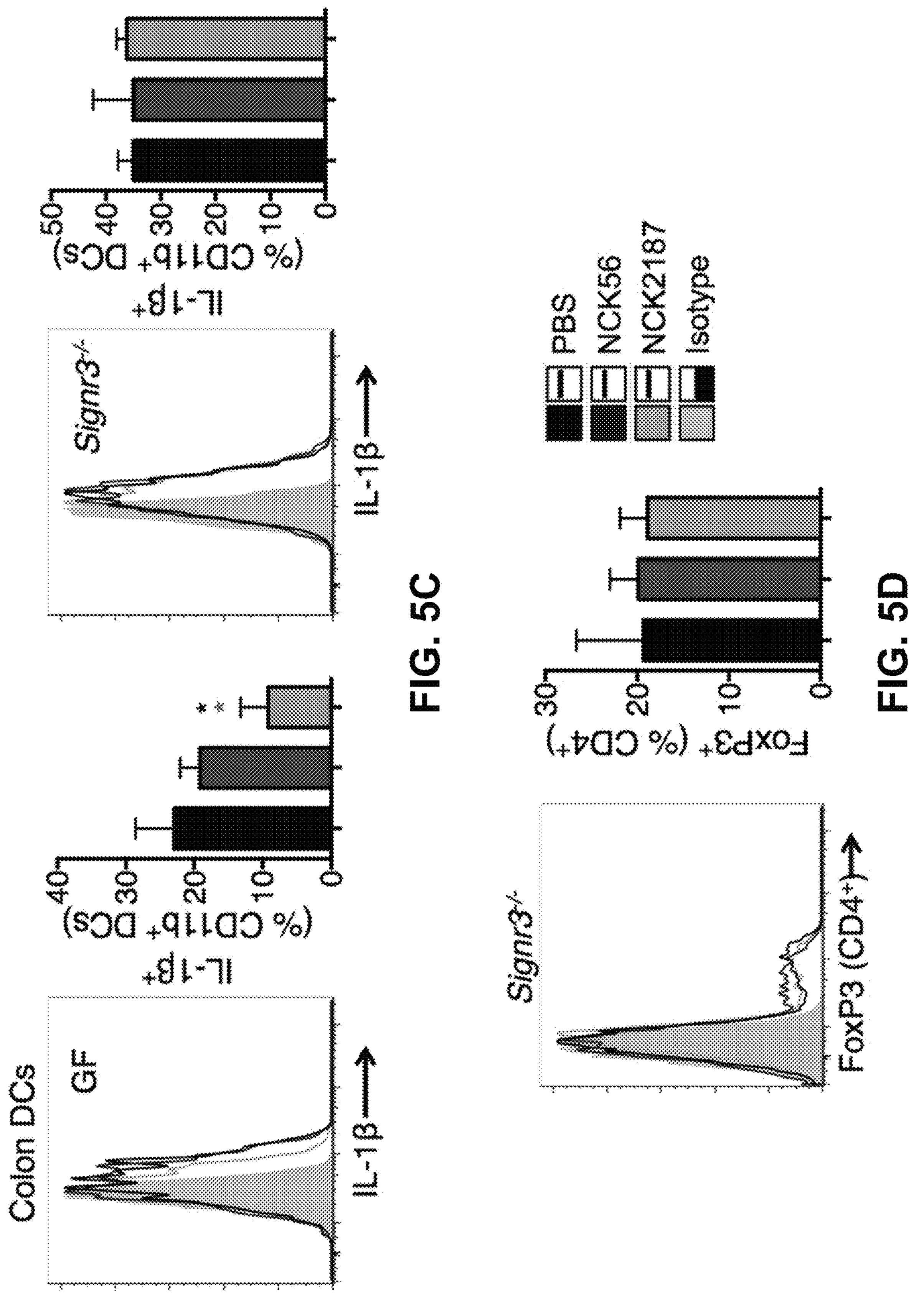

To clarify the role of SlpA:SIGNR3 binding and signaling in vivo, we first orally treated WT and $Signr3^{-/-}$ mice with our bacterial strains and analyzed the immunologic responses induced in steady-state. While NCK2187 treatment led to reduced IL-1β in both conventional (data not shown) and germ-free (GF) B6 mice (FIG. 5C, left), no anti-inflammatory effects were observed in NCK2187-treated $Signr3^{-/-}$ mice (FIG. 5C, right). Furthermore, the Treg-inducing properties of NCK2187 (FIGS. 2A and 2B) were abrogated in $Signr3^{-/-}$ mice (FIG. 5D). These data strongly suggest that NCK2187 delivers immunoregulatory signals via its interaction with SIGNR3.

Example 4—NCK2187 and its SlpA Cannot Prevent Dextran Sulfate Sodium (DSS) Induced Colitis in the Absence of Signr3 Signaling Previous reports have highlighted the role of specific CLRs in experimental colitis. For instance, mice lacking Signr1 expression are less susceptible to induced colitis (Saunders et al., 2010), while mice deficient in Dectin1 and Signr3 exhibit exacerbated disease (Eriksson et al., 2013; Iliev et al., 2012). To further investigate SlpA:SIGNR3 signaling in disease conditions, DSS-treated WT and $Signr3^{-/-}$ mice were orally gavaged with NCK56, NCK2187, or SlpA, and monitored for disease progression.

Consistent with the T cell-induced colitis model, disease progression and severity were significantly reduced in WT mice orally treated with NCK2187 or purified SlpA (FIG. 6 and Table 6); however, NCK2187 and SlpA did not confer any protection in $Signr3^{-/-}$ mice (FIG. 6). Measurements included weight loss, histopathology-based colitis scores, evaluation of gross mucosal damage, and immune cell recruitment and activation (FIGS. 6 and 7).

Figure 6A:
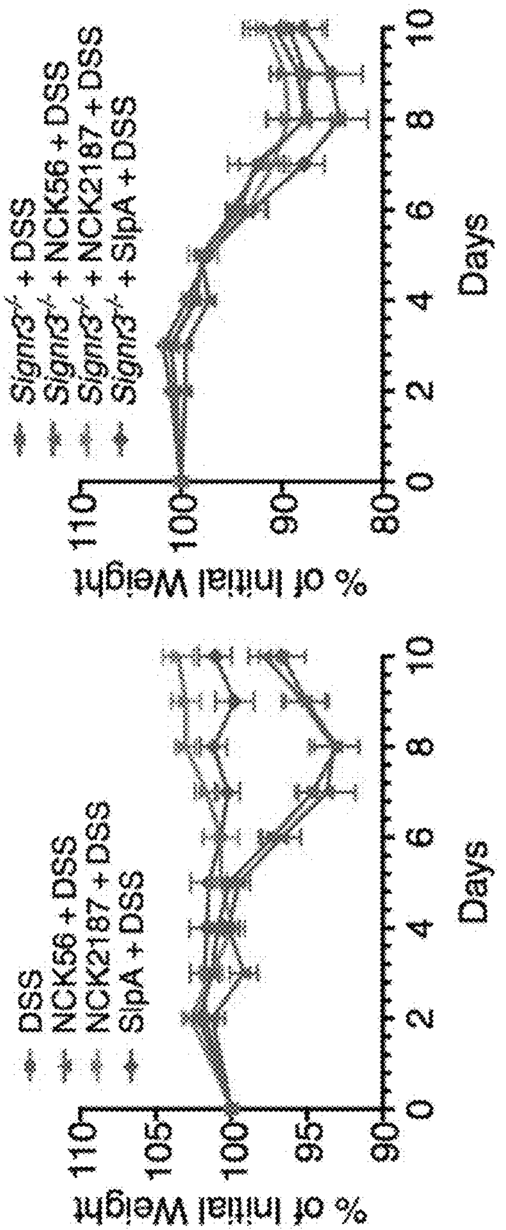
FIGS. 6A-6H. *L. acidophilus* NCK2187 and its SlpA do not protect against DSS-induced colitis in $Signr3^{-/-}$ mice. WT or $Signr3^{-/-}$ (KO) mice were orally gavaged with NCK56, NCK2187 or SlpA at days −1 and −3, and 3% DSS was given in the drinking water. Mice were gavaged with bacteria or purified SlpA an additional 2 times and monitored for disease progression. Colitis severity was determined in part by weight loss (A). (See Table 6 for statistical analyses from WT mice.) B-C. Colitis scores based on histopathology, and gross morphology of the colons were also used as measures of disease. Scale bar=200 μm. n=5 mice/group. Empty bars=WT; lined bars=KO; white bars=untreated; purple bars=DSS; red bars=DSS+NCK56; green bars=DSS+NCK2187; blue bars=DSS+SlpA. D. Colonoscopies were performed in the different groups with a Multi-Purpose Rigid™ Telescope attached to a TELE PACK X. E. Mean relative colonic expression of tight junction-associated genes in WT mice. F. Fecal albumin levels in WT mice as a measure of intestinal permeability. G. UniFrac analyses were used to calculate distances between the microbial communities of the different samples (Day 10) and three-dimensional scatterplots were generated by using PCoA. Light gray: WT+DSS; green: WT+DSS+NCK56; brown: WT+DSS+NCK2187; blue: WT+DSS+SlpA; aqua: KO+DSS; red: KO+DSS+NCK56; yellow: KO+DSS+NCK2187; purple: KO+DSS+SlpA. n=4-6 mice/group. H. Species richness and microbial diversity in DSS-treated mice. Top: The Chao richness index was used as a measure of species richness. Bottom: The Shannon diversity index was used to estimate microbial diversity for each group. Data are shown as mean±SEM. *P<0.05, P<0.01, **P<0.0001.
Figure 6B:
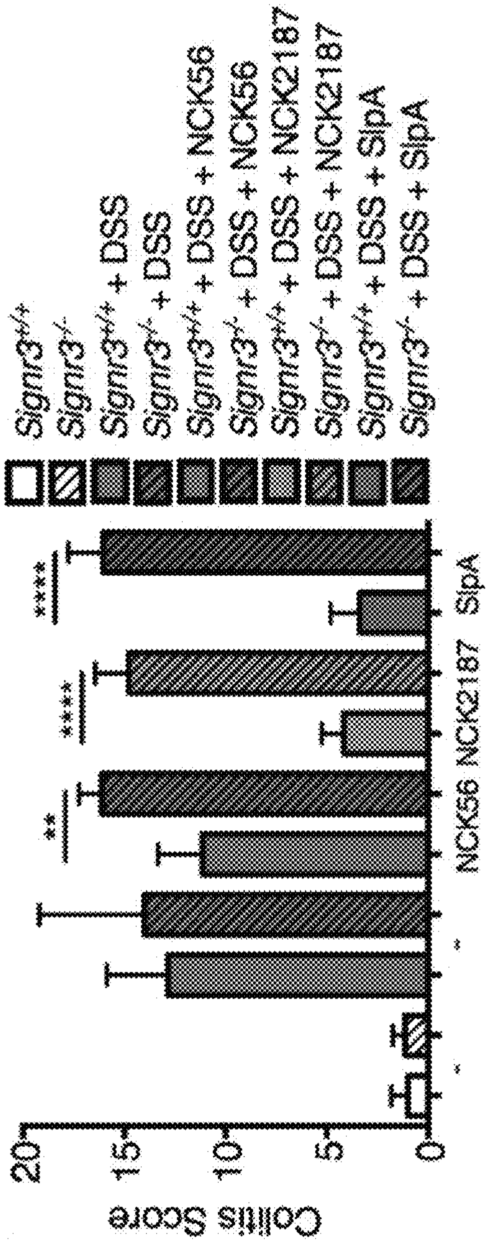
Figure 6C:
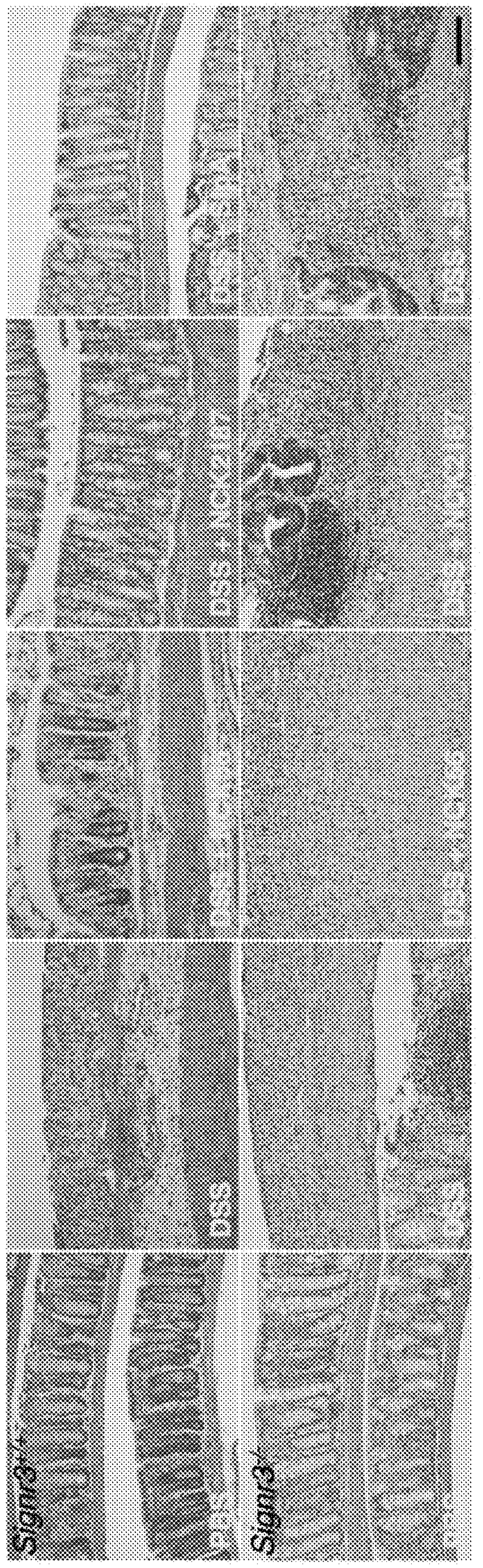
Figure 6D:
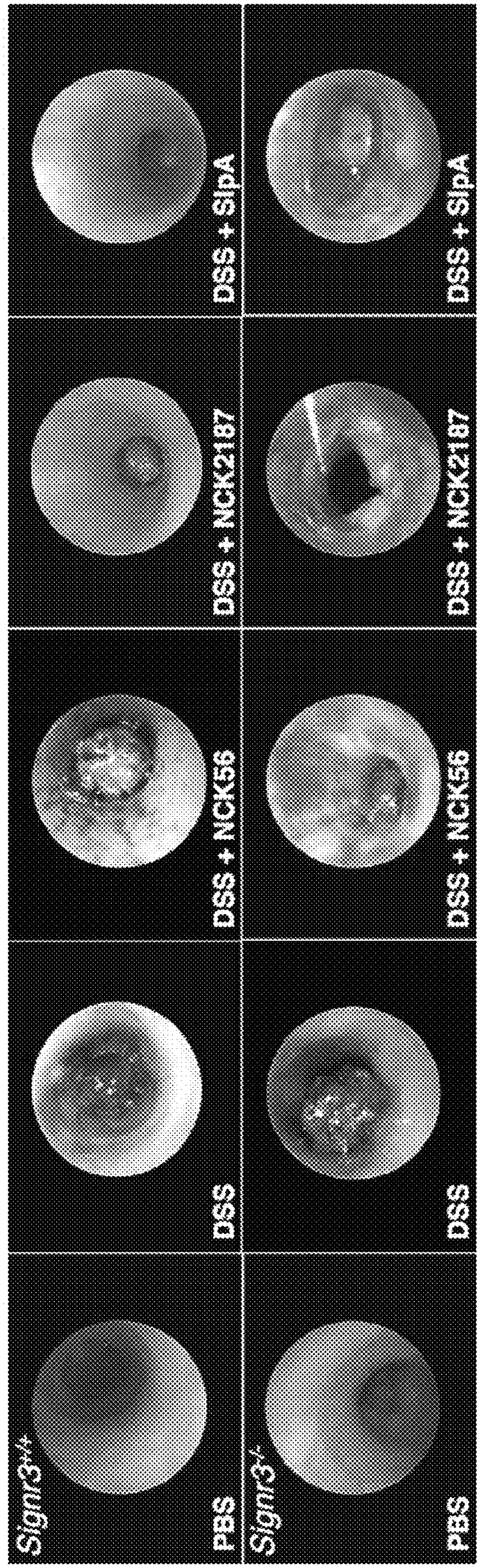
Figure 6E:
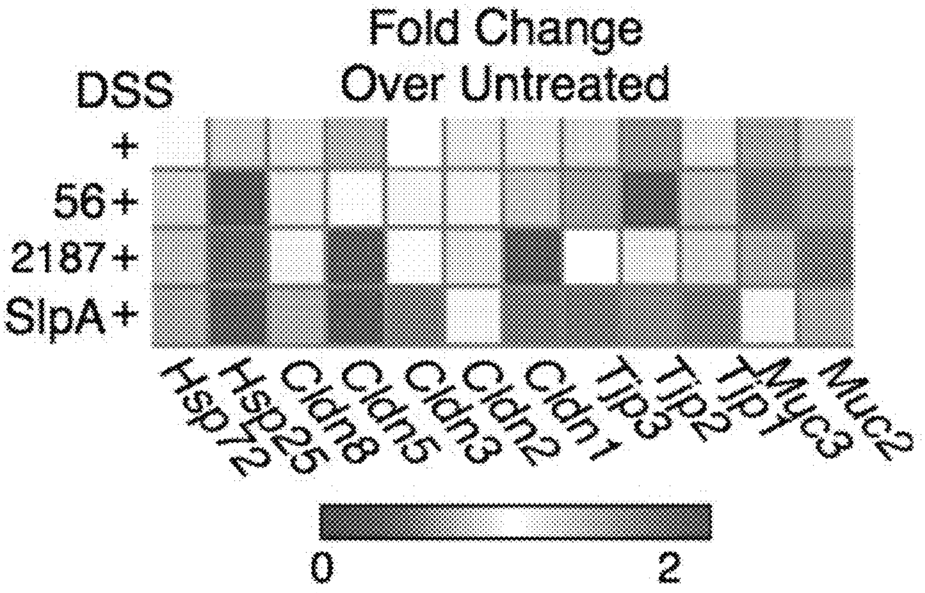

Disease progression and inflammation were associated with alterations in intestinal barrier integrity and the composition of the gut microbiota (FIGS. 6E-6H). Several gut permeability markers were evaluated by RT-PCR. The restoration of claudins (Cldn1, Cldn3, and Cldn5) in WT mice treated with NCK2187 or SlpA, indicate that NCK2187 and SlpA were capable of promoting intercellular tight junctions (FIG. 6E).

Figure 6F:
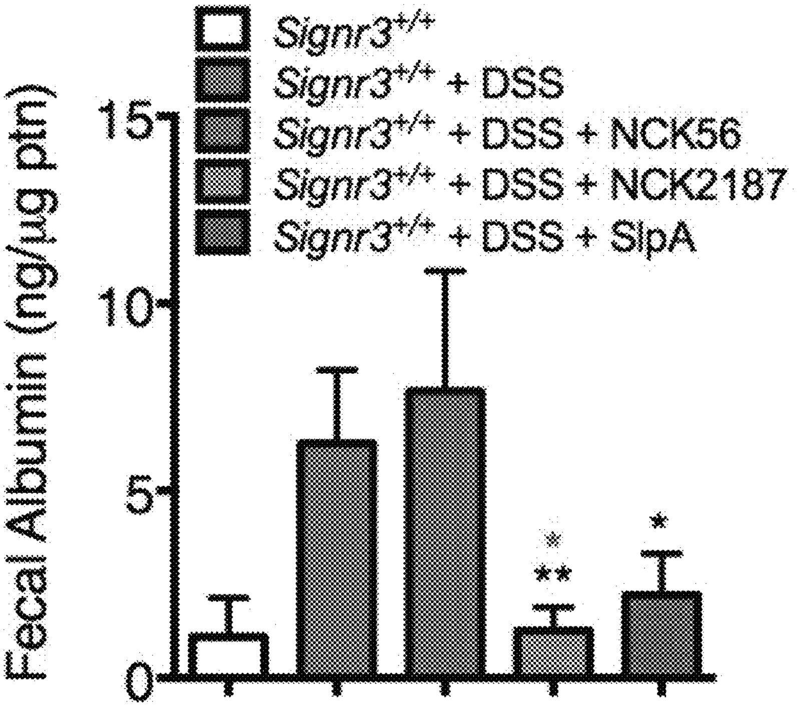

Accordingly, only NCK2187 and SlpA treatments of WT mice prevented increased fecal albumin levels seen with protein-losing enteropathies after DSS treatment (FIG. 6F). On the other hand, no positive effects by NCK2187 or SlpA on barrier integrity were noted in $Signr3^{-/-}$ mice (data not shown). In terms of microbiota composition, protected WT mice (NCK2187- and SlpA-treated) clustered together in UniFrac analyses, while diseased untreated and NCK56-treated WT mice clustered separately (FIG. 6G).

Figure 6G:
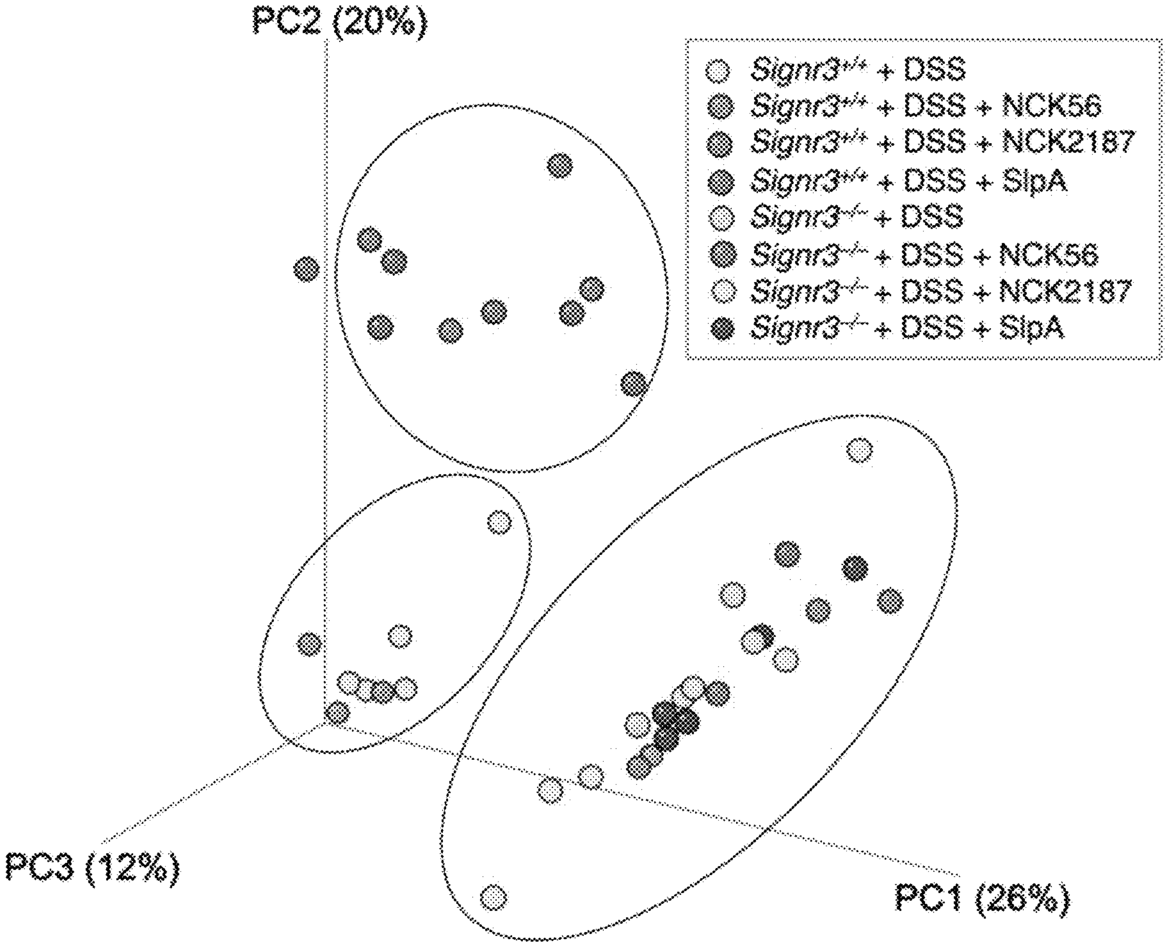
Figure 6H:
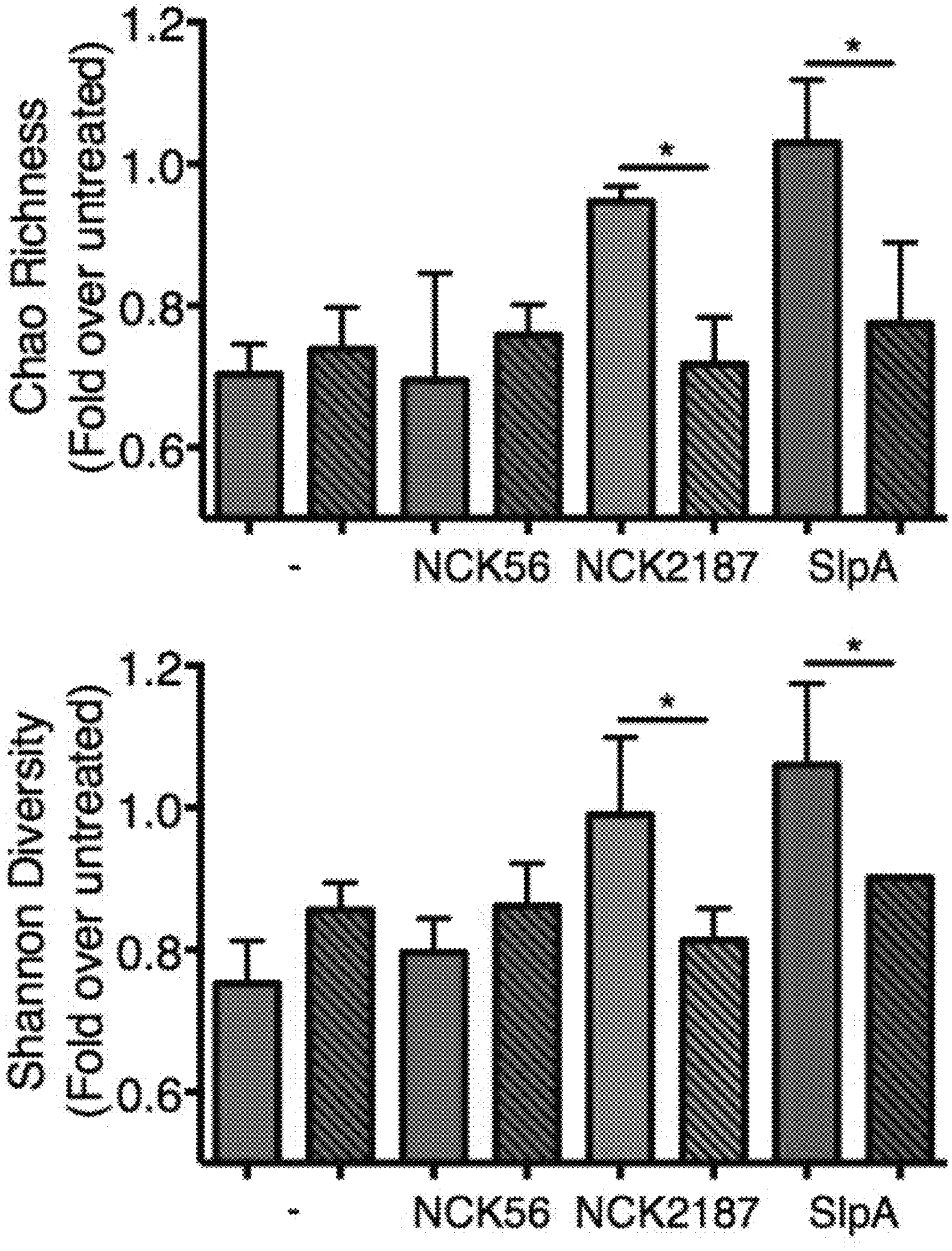

Conversely, the microbial communities of all DSS-treated $Signr3^{-/-}$ mice formed a single cluster, indicating that dysbiosis was uniformly distributed independent of treatment group (FIG. 6G). Furthermore, richness and diversity, analyzed by the Chao Richness index and Shannon Diversity index, respectively, were maintained in NCK2187- and SlpA-treated WT mice, while no such effects could be observed in $Signr3^{-/-}$ mice (FIG. 6H).

TABLE 6

Statistical analysis of weight loss curves in DSS-induced colitis in WT mice.

| | Weight Loss (p-value) | | | |
|---|---|---|---|---|
| | vs. + DSS alone | | vs. + NCK56 | |
| Day | +NCK2187 | +SlpA | +NCK2187 | +SlpA |
| 1 | 1.0 | 1.0 | 1.0 | 1.0 |
| 2 | 0.6705 | 0.7567 | 0.2844 | 0.7430 |
| 3 | 0.9668 | 0.7071 | 0.0862 | 0.0580 |
| 4 | 0.3974 | 0.5816 | 0.8394 | 0.2873 |
| 5 | 0.6360 | 0.2916 | 0.3444 | 0.1472 |
| 6 | 0.0087 | 0.0181 | 0.0042 | 0.0098 |
| 7 | <0.0001 | 0.0001 | <0.0001 | <0.0001 |
| 8 | <0.0001 | <0.0001 | <0.0001 | <0.0001 |

TABLE 6-continued

Statistical analysis of weight loss curves in DSS-induced colitis in WT mice.

| | Weight Loss (p-value) | | | |
|---|---|---|---|---|
| | vs. + DSS alone | | vs. + NCK56 | |
| Day | +NCK2187 | +SlpA | +NCK2187 | +SlpA |
| 9 | <0.0001 | 0.0011 | <0.0001 | 0.0035 |
| 10 | <0.0001 | 0.0023 | <0.0001 | 0.0359 |

Figure 7A:
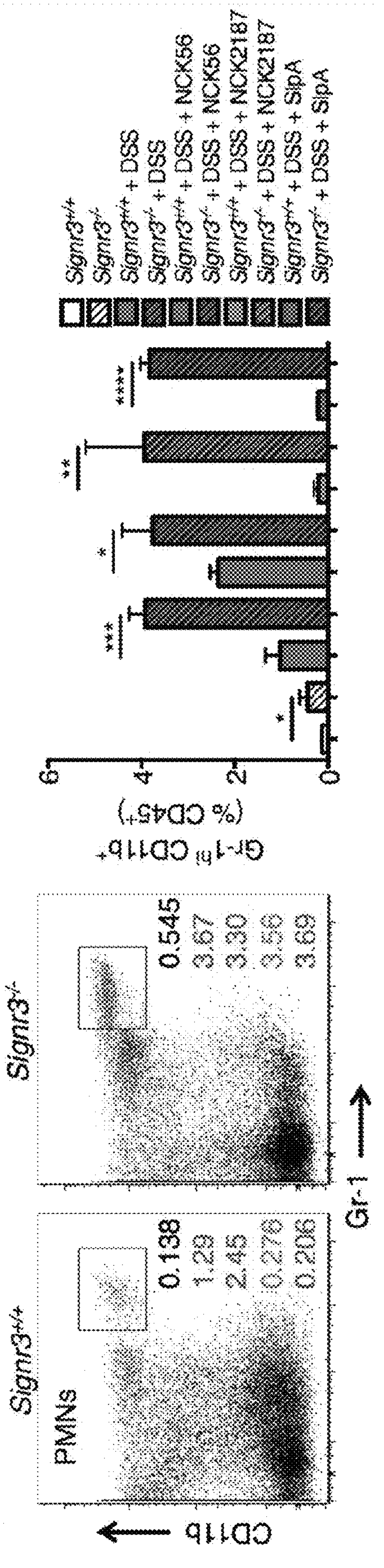
FIGS. 7A-7C. *L. acidophilus* NCK2187 and its SlpA do not prevent immune infiltration and activation during DSS-induced colitis in $Signr3^{-/-}$ mice. WT or $Signr3^{-/-}$ (KO) mice were orally gavaged with NCK56, NCK2187 or SlpA at days −1 and −3, and 3% DSS was given in the drinking water. Mice were gavaged with bacteria or purified SlpA an additional 2 times, and immunity analyzed by flow cytometry at day 10. A. Representative plots indicate the frequency of neutrophils in the colons of untreated or DSS-treated WT (left) and $Signr3^{-/-}$ mice (right). B-C. Colonic DCs and MΦs were analyzed by flow cytometry for the production of IL-113 (B), and colonic Tregs were evaluated for co-expression of $ROR\gamma t^+$ (C). n=5 mice/group. Gray tinted line=isotype control; black=untreated; purple=DSS; red=DSS+NCK56; green=DSS+NCK2187; blue=DSS+SlpA. Data are shown as mean±SEM, and are representative of three different experiments. *P<0.05, P<0.01, *P<0.001, ****P<0.0001.
Figure 7B:
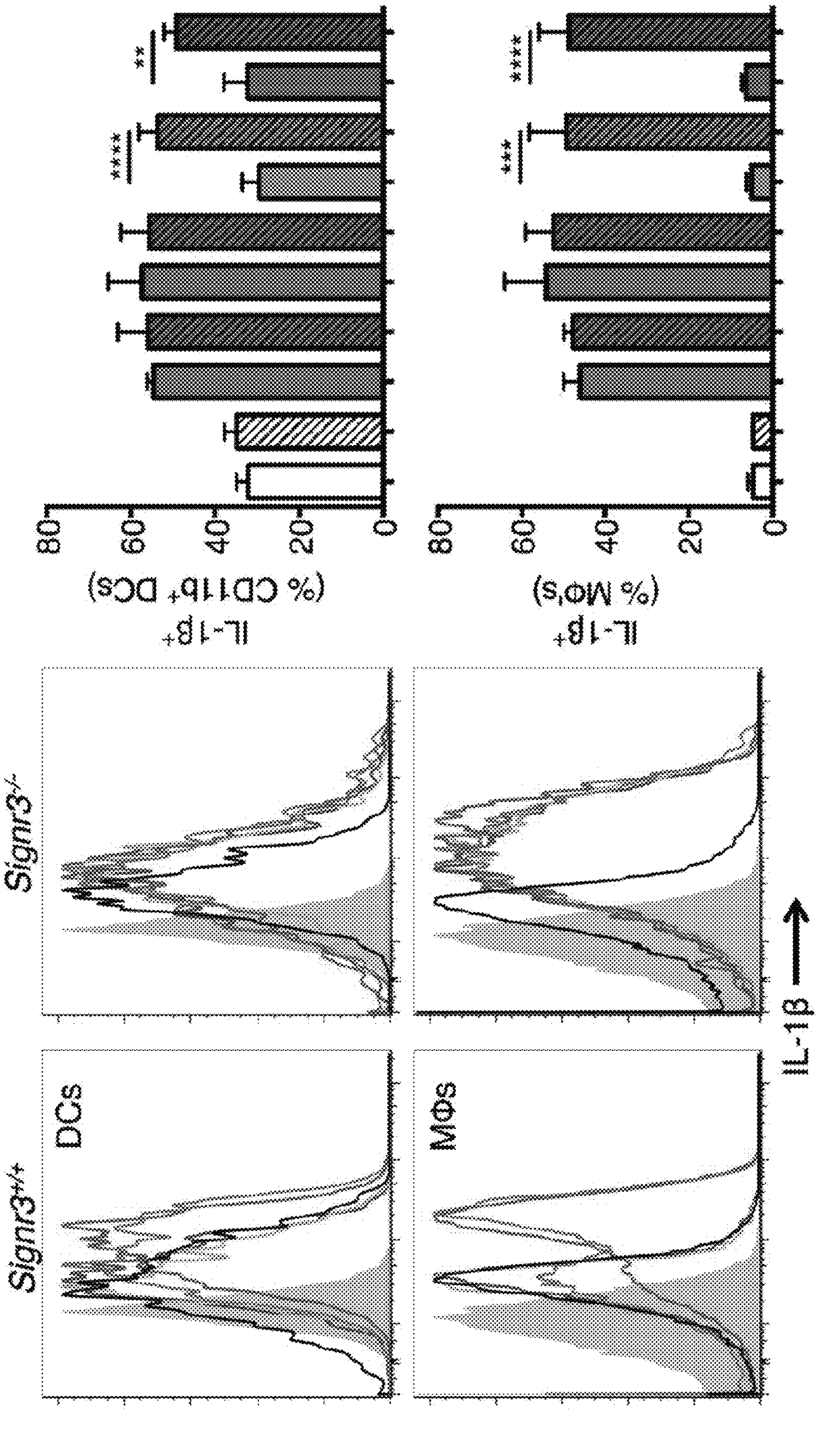

Induced immune responses in the colons of DSS-treated mice were analyzed to determine differences, if any, among the treatment groups. Neutrophilic infiltration in the colons of NCK2187- and SlpA-treated SIGNR3-sufficient mice that were given DSS decreased to nearly PBS-treated control mice levels; while, in contrast, an even higher frequency of infiltrating neutrophils was detected in Signr3$^{-/-}$ mice after the induction of colitis, irrespective of the treatment group analyzed (FIG. 7A). Similarly, the number of IL-1β-producing DCs and macrophages was significantly decreased with NCK2187 and SlpA treatment in WT mice; however, no changes were observed among the different treatment groups in the absence of SlpA: SIGNR3 signaling (FIG. 7B).

Figure 7C:
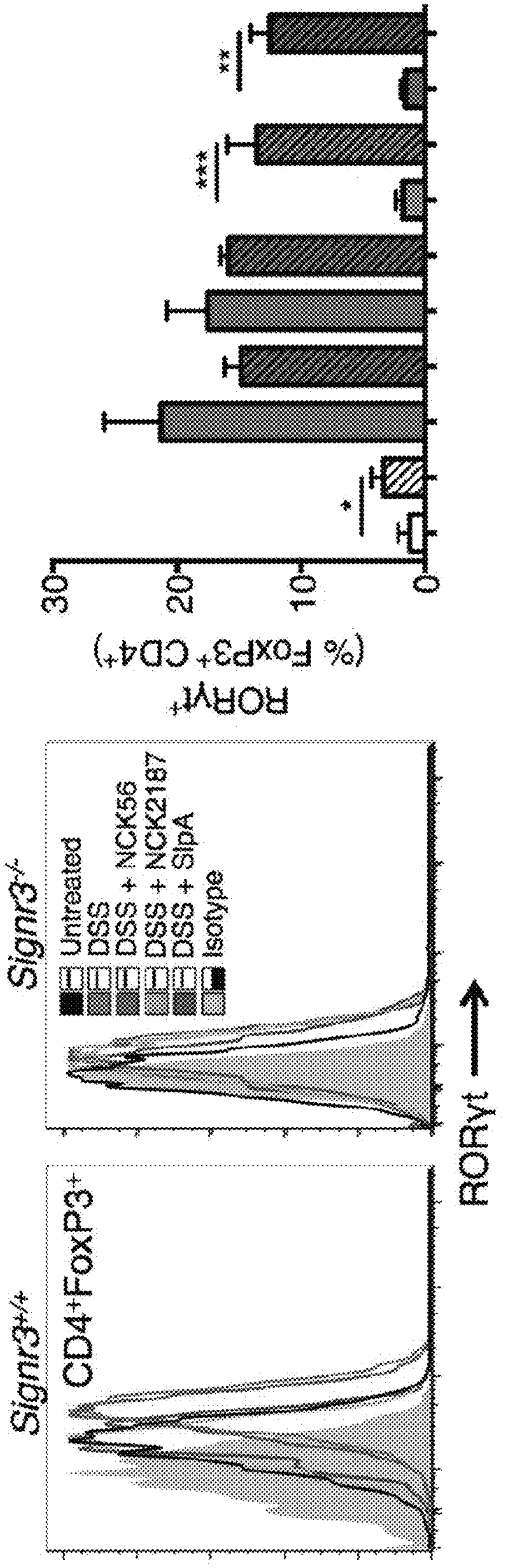
Figure 9:
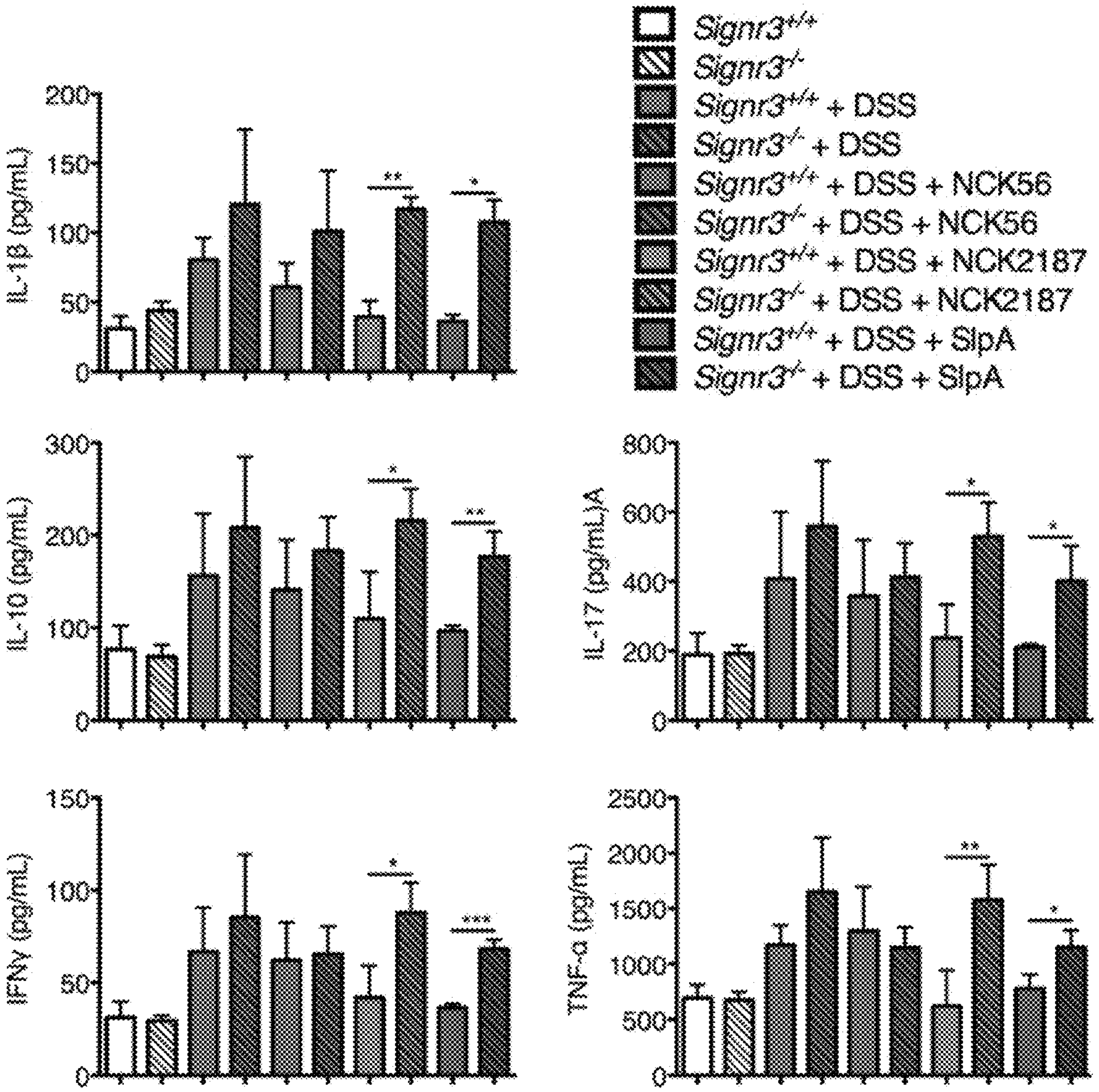
FIG. 9. *L. acidophilus* NCK2187 and its SlpA cannot normalize sera cytokine levels upon DSS-induced colitis in $Signr3^{-/-}$ mice. WT or $Signr3^{-/-}$ mice were orally gavaged with NCK56, NCK2187 or SlpA at days −1 and −3, and 3% DSS was given in the drinking water. Mice were gavaged with bacteria or purified SlpA an additional 2 times. Cytokine levels were measured in the sera at the endpoint of the experiment. n=4 mice/group. Empty bars=WT; lined bars=KO; white bars=untreated; purple bars=DSS; red bars=DSS+NCK56; green bars=DSS+NCK2187; blue bars=DSS+SlpA. Data are shown as mean±SEM. *P<0.05, P<0.01, *P<0.001.

Pathogenic inflammation can result in proinflammatory FoxP3$^+$RORγt$^+$ Tregs (Hovhannisyan et al., 2011; Khazaie et al., 2012). While no major change in the total number of FoxP3$^+$ Tregs was measured among the WT and Signr3$^{-/-}$ KO groups, the quality of these Tregs was significantly altered. A large number of FoxP3$^+$ cells co-expressed RORγt after DSS treatment in both WT and Signr3$^{-/-}$ mice (FIG. 7C). However, in accordance with the protection observed, NCK2187 and SlpA treatment prevented the generation of FoxP3$^+$RORγt$^+$ Tregs only in WT mice but not Signr3$^{-/-}$ mice (FIG. 7C). Correspondingly, the levels of circulating cytokines in the sera (IL-1β, IL-10, IL-17A, IFNγ and TNF-α) were rebalanced only in NCK2187- and SlpA-treated WT mice but not in Signr3$^{-/-}$ mice (FIG. 9).

Collectively, these clinical and immunologic data provide robust evidence in support of an immunoregulatory role for *L. acidophilus* SlpA that is highly dependent on intact SIGNR3 signaling.

Figure 10A:
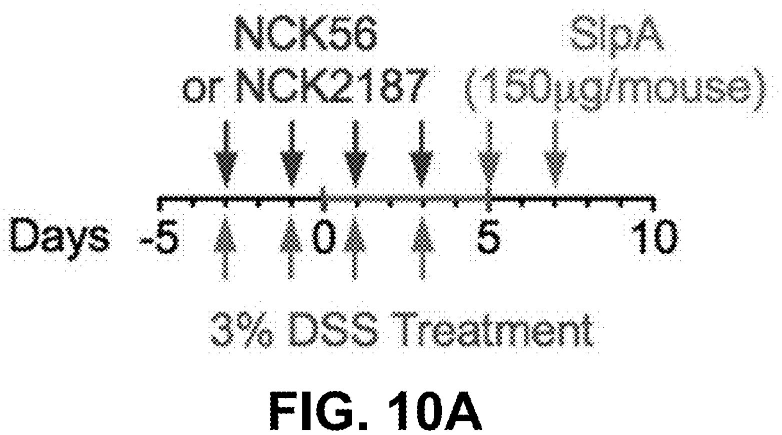
FIGS. 10A-10B. Dextran sodium sulfate (DSS) treatment and oral gavage regimens. (A) DSS-induced colitis prevention study; mice were orally gavaged with NCK56, NCK2187 or SlpA at the specified time points. 3% DSS was given in the drinking water from days 0 to 5. (B) DSS-induced colitis therapy. 3% DSS was given in the drinking water from days 0 to 5. Mice were then orally gavaged with NCK56, NCK2187, or SlpA at the circled time points.
Figure 11A:
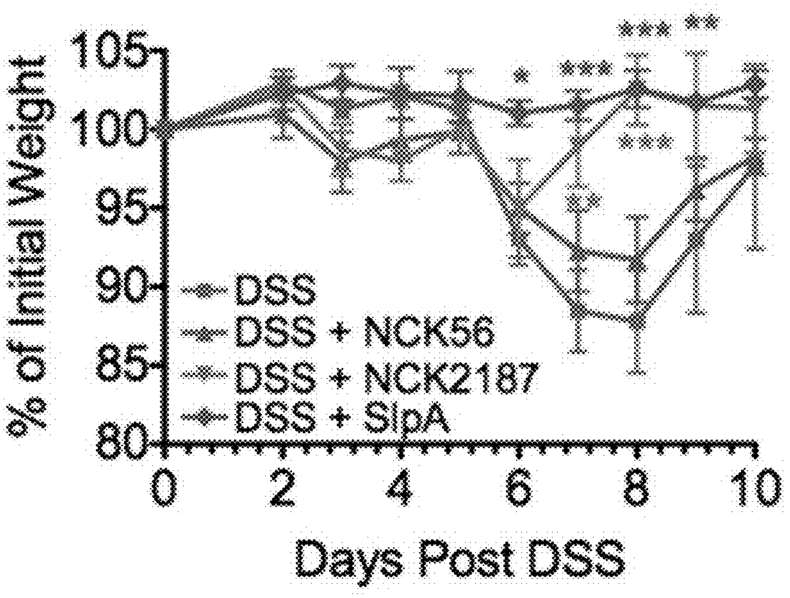
FIGS. 11A-11E. *L. acidophilus*-SlpA protects against DSS-induced colitis. C57BL/6 mice were orally gavaged with NCK56, NCK2187 or SlpA, and 3% DSS was given in the drinking water. Colitis development in the mice was monitored by measuring weight loss (A), diarrhea development (B), presence of fecal occult blood (FOB) (C), gross morphology of the colons (D), and histopathology (E). *P<0.05, P<0.01 and *P<0.001 representing the specified group by its color compared with PBS.
Figure 11B:
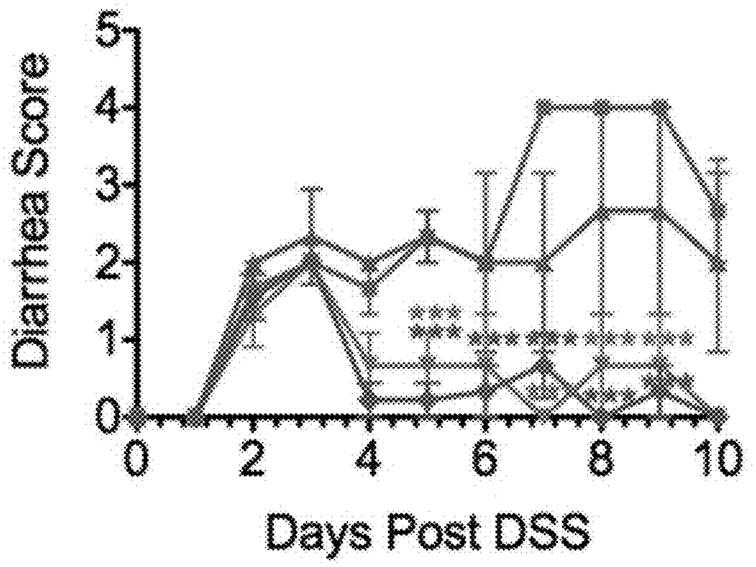
Figure 11C:
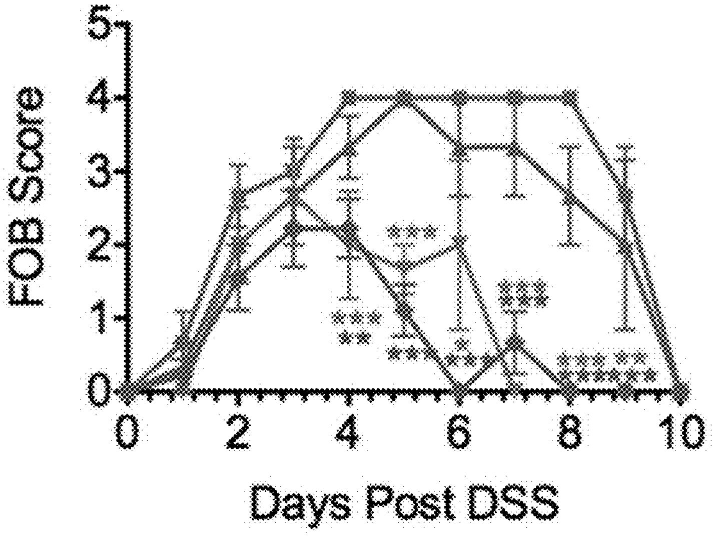
Figure 11D:
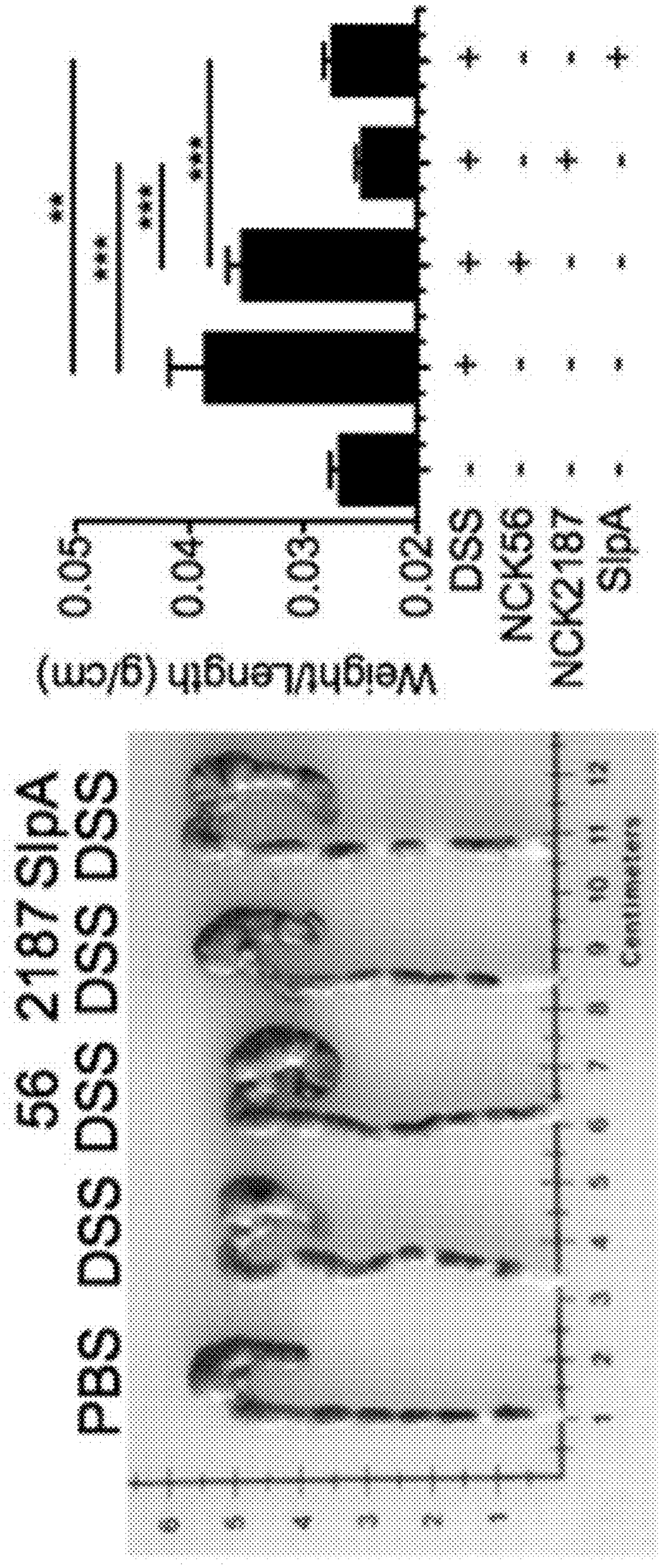
Figure 11E:
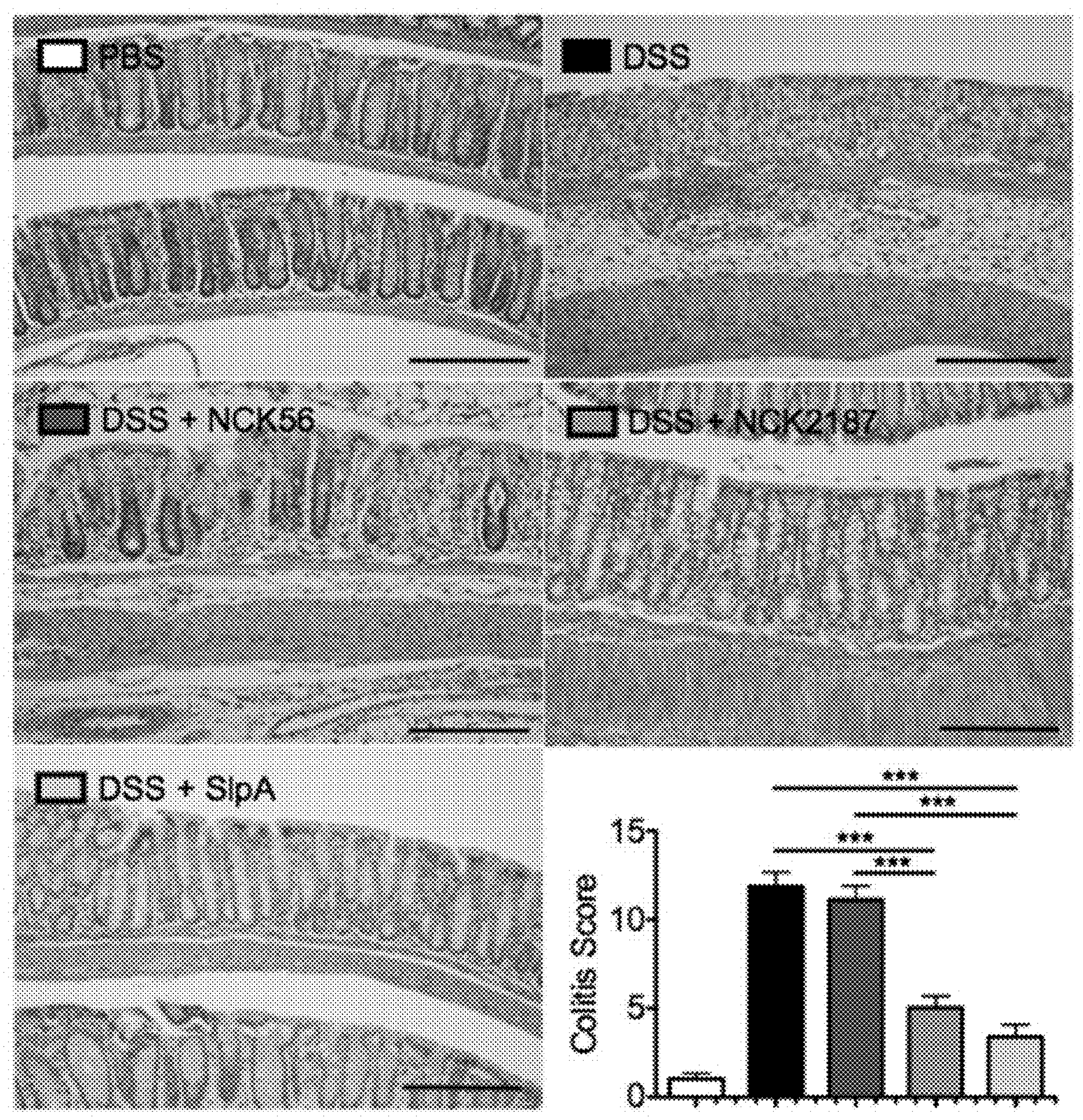
Figure 12A:
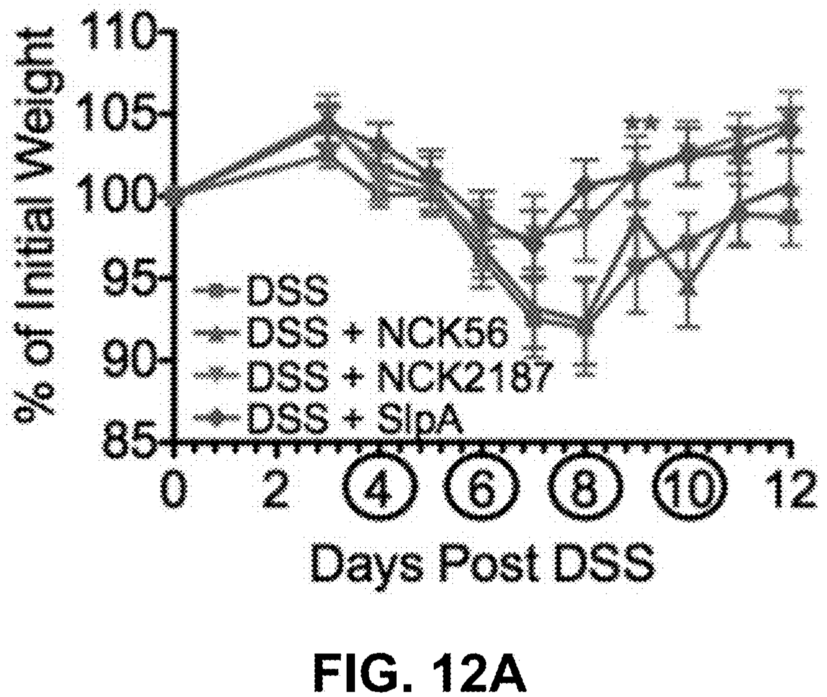
FIGS. 12A-12E. *L. acidophilus*-SlpA reverses DSS-induced colitis. C57BL/6 mice were given 3% DSS in the drinking water, and were then orally gavaged with NCK56, NCK2187 or SlpA. Colitis development in the mice was monitored by measuring weight loss (A), diarrhea development (B), presence of fecal occult blood (FOB) (C), gross morphology of the colons (D), and histopathology (E). *P<0.05 and **P<0.01 representing the specified group by its color compared with PBS.
Figure 12B:
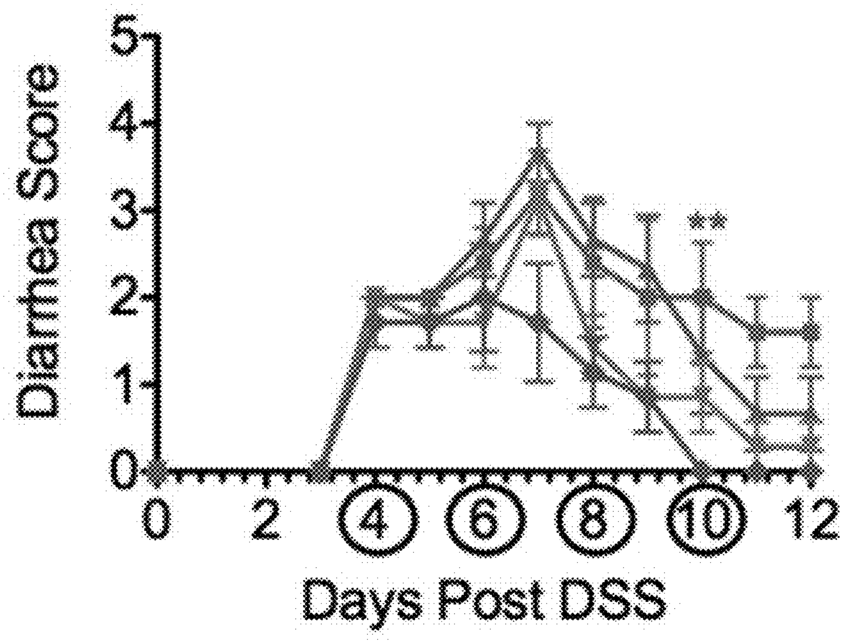
Figure 12C:
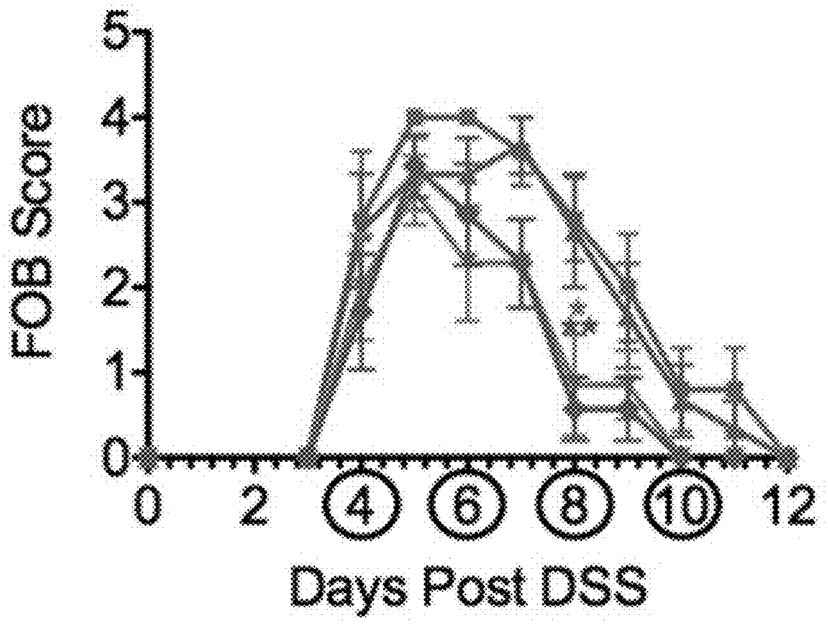
Figure 12D:
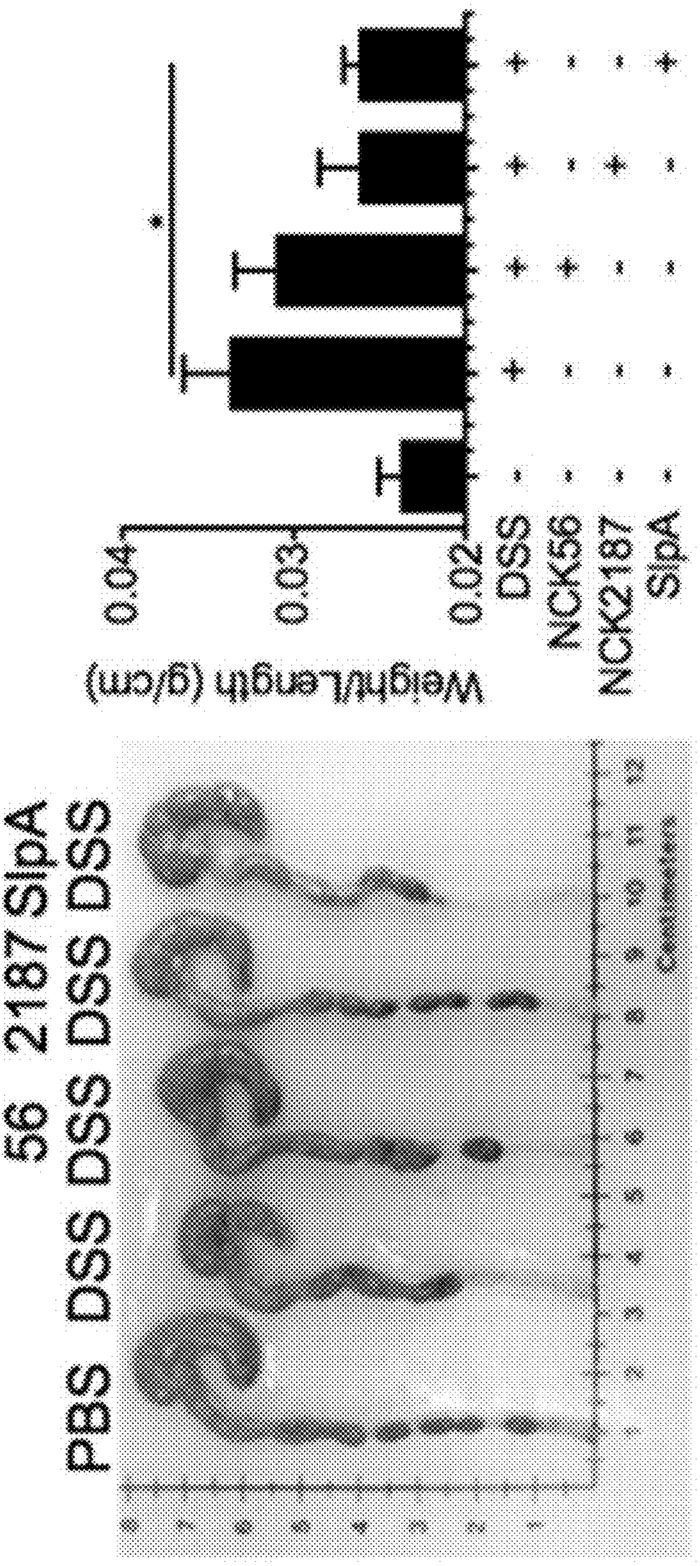
Figure 12E:
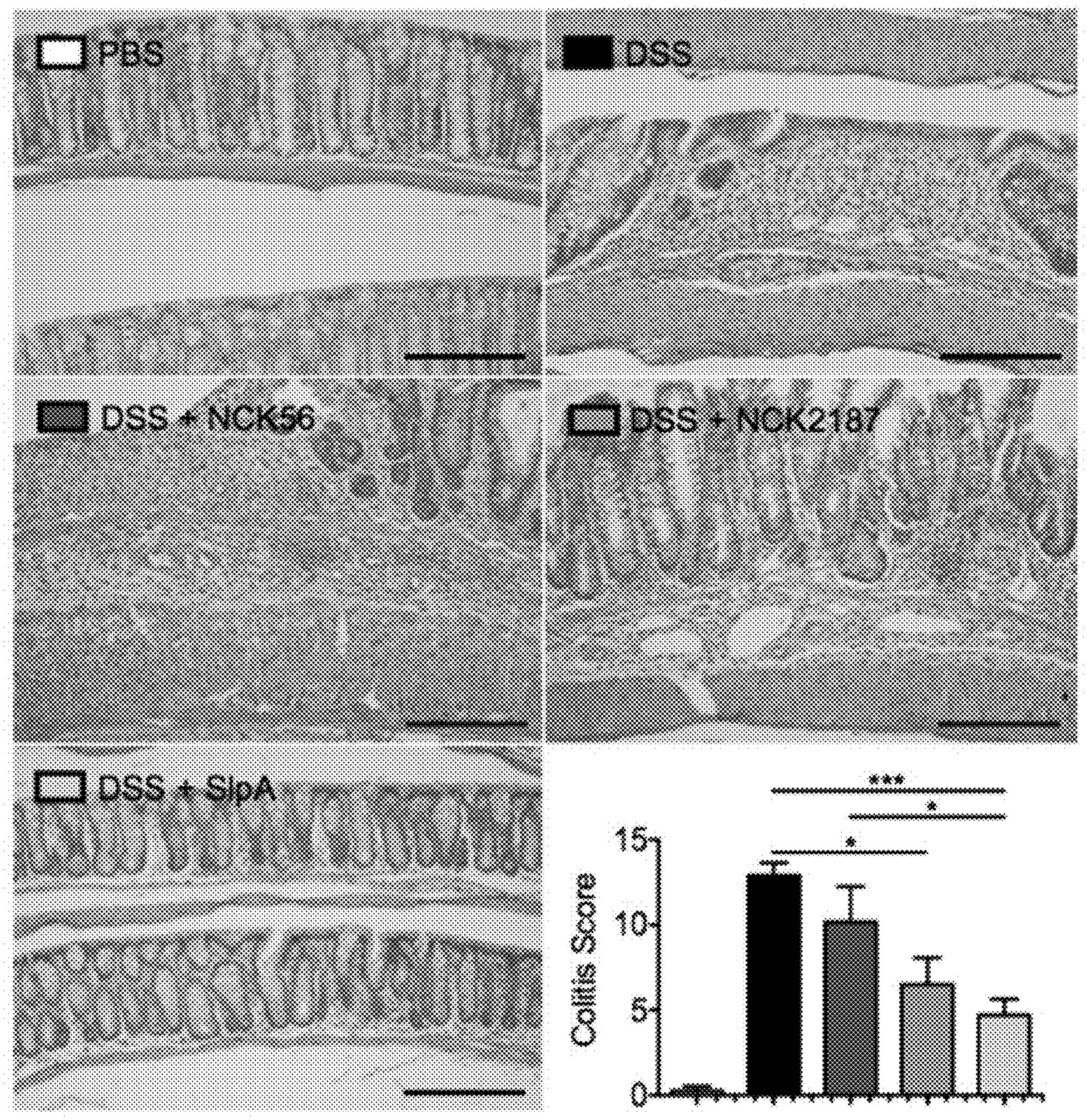

Example 5—Effective Dose for Prevention of DSS-Induced Colitis by L. *Acidophilus* SlpA To test the required dose of purified SlpA for efficacy in the prevention of colitis, DSS-induced colitis model was employed. 6 oral treatments with 150 μg SlpA/mouse, and only 4 oral gavages of $10^9$ CFU NCK2187 were sufficient to prevent weight loss in mice given 3% DSS in the drinking water for 5 days (FIG. 11A). See FIG. 10A for graphical summary of the treatment regimen. For the DSS-induced colitis prevention studies, age and sex-matched C57BL/6 mice were gavaged twice with NCK56 (WT), NCK2187, or purified SlpA, prior to being given 3% DSS in the drinking water. At the start of the treatment, the mice were gavaged twice more with the different bacterial strains or 4 more times with SlpA to compensate for the ability of NCK56 and NCK2187 to persist in these animals for 3 days post-gavage (FIG. 1D). Mice treated with NCK2187 or SlpA developed only a mild form of colitis and recovered significantly faster than DSS-alone or NCK56-treated mice (FIG. 11). Collectively, these data suggest that NCK2187 and SlpA are suitable treatments for the prevention of colitis.

Example 6—Reversal of DSS-Induced Colitis by *Acidophilus*SlpA

Figure 10B:
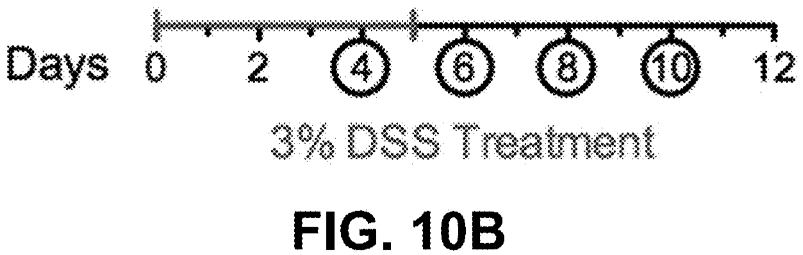

Having tested the protective capacity of *L. acidophilus* SlpA, its ability to ameliorate established colitis was tested. For these studies, mice were orally gavaged with varying bacteria strains or purified SlpA once signs of colitis were noted, i.e., diarrhea and fecal occult blood (see FIG. 10B for treatment regimen). Mice receiving either NCK2187 or SlpA recovered significantly faster than NCK56-treated or DSS-alone treated mice (FIG. 12). These results indicate that NCK2187 and SlpA are efficacious in ameliorating existing colitis.

Example 7—Prevention of T Cell-Induced Colitis by *L. acidophilus* SlpA

Figure 13A:
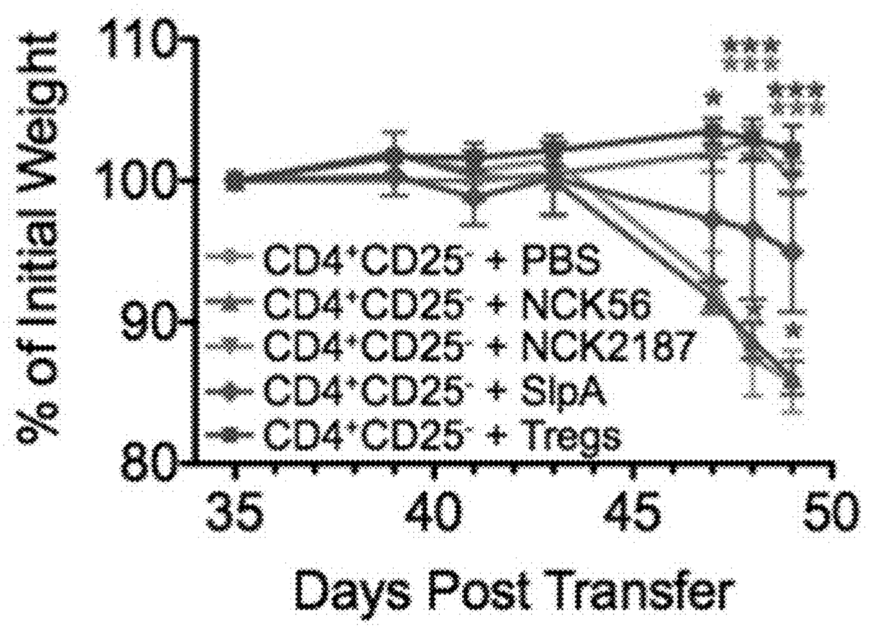
FIGS. 13A-13E. *L. acidophilus*-SlpA protects against pathogenic T cell-induced colitis. $Rag^{1-/-}$ mice were injected with $10^6$ $CD4^+CD25^-$ T cells, and were then orally gavaged with NCK56, NCK2187, or SlpA, 1 and 3 days after transfer, and subsequently once a week for 4 consecutive weeks. Colitis development in the mice was monitored by measuring weight loss (A), diarrhea development (B), presence of fecal occult blood (FOB) (C, gross morphology of the colons (D), and histopathology (E). *P<0.05.
Figure 13B:
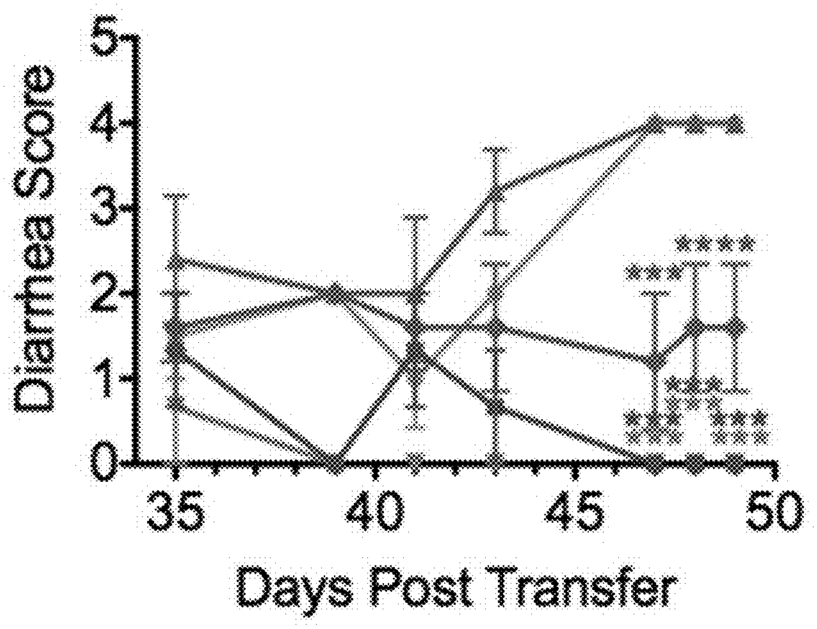
Figure 13C:
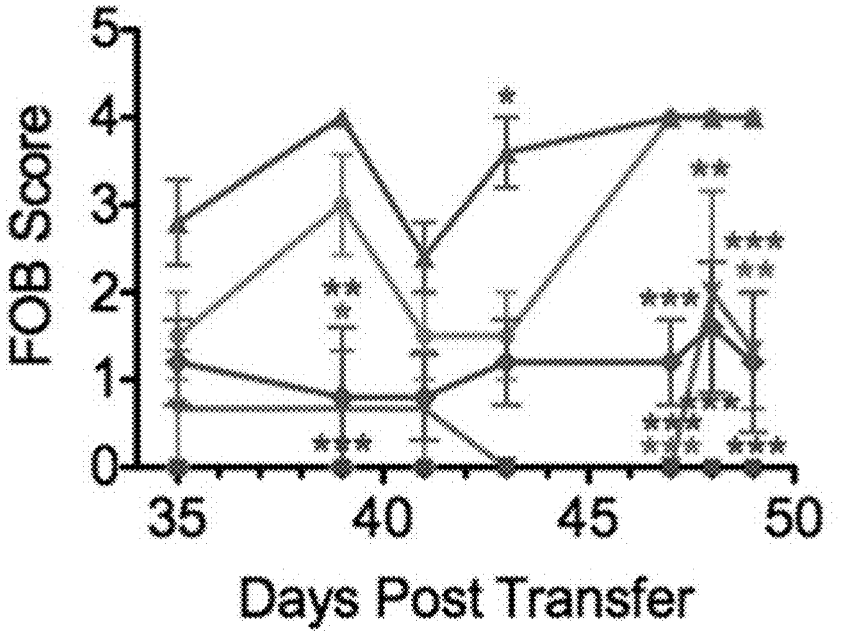
Figure 13D:
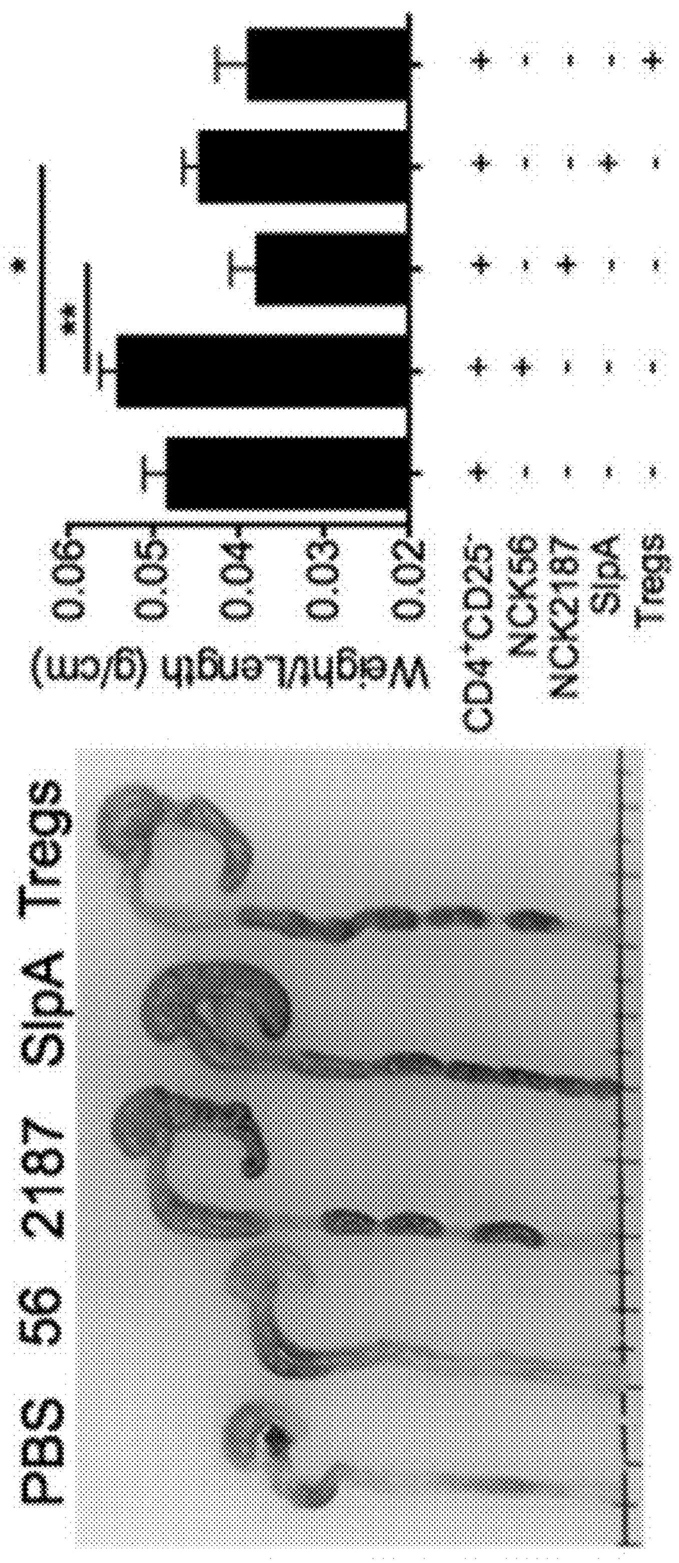
Figure 13E:
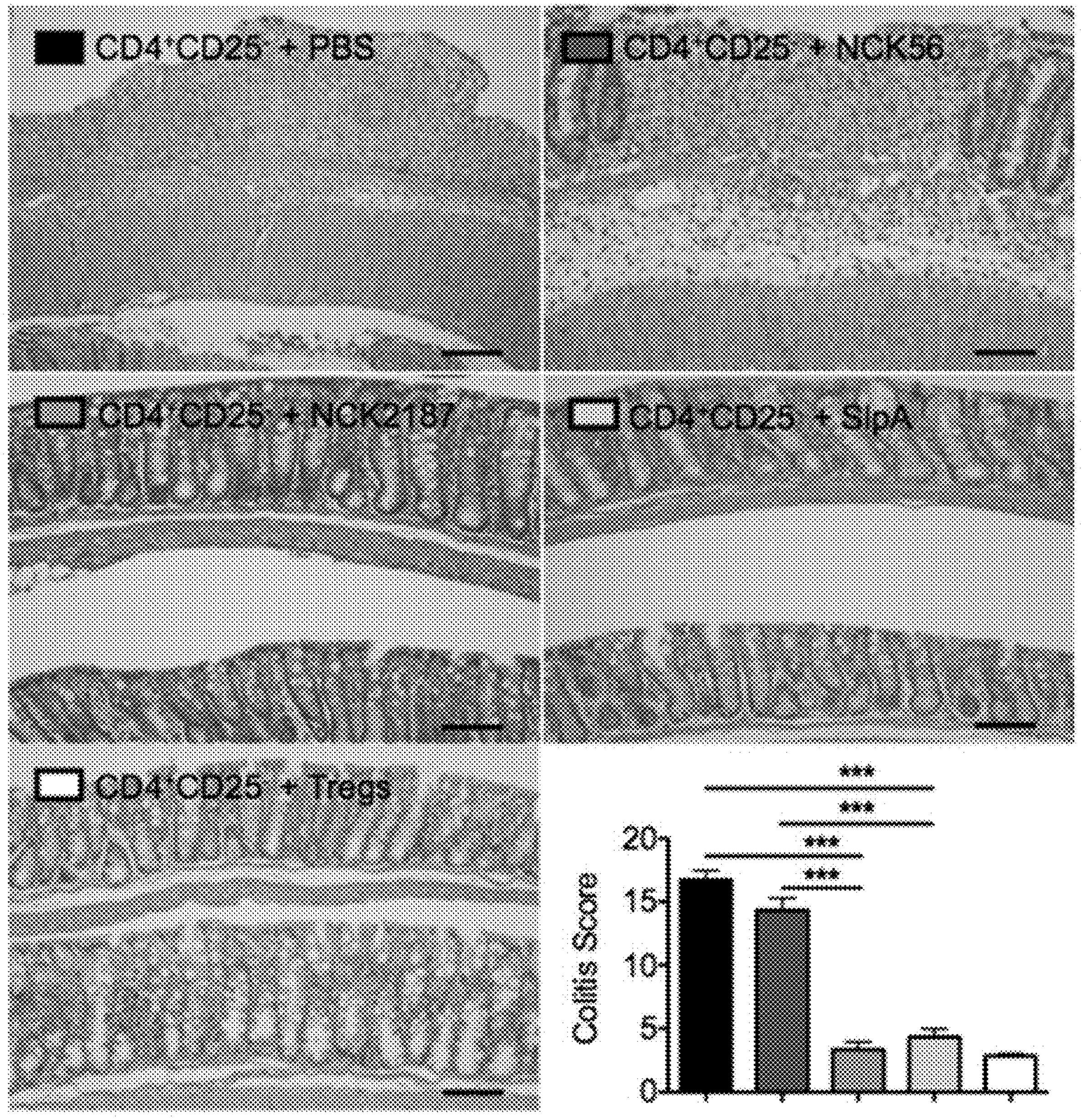

The regulatory effects of *L. acidophilus* SlpA in a chronic inflammatory model of colitis, namely, the pathogenic T cell transfer model was tested. Immunodeficient Rag1$^{-/-}$ mice were injected with regulatory T cell (Treg)-depleted CD4$^+$ splenic cells (CD4$^+$CD25$^-$), then left untreated or gavaged with NCK56, NCK2187, or purified SlpA (150 μg/mouse), and monitored for the onset of colitis. Recipient mice were gavaged twice with their corresponding treatments at days 1 and 3 after the transfer, then once a week for the next 4 weeks, for a total of 6 gavages. An additional group receiving Tregs was used as a positive control for the prevention of colitis. Oral treatment with $10^9$ CFU NCK2187 was as effective as the Tregs in the prevention of weight loss in recipient Rag1$^{-/-}$ mice (FIG. 13A). Purified SlpA was also found to be protective in recipient Rag1$^{-/-}$ mice (FIG. 13); however, given the chronic nature of the model, a higher dose of SlpA may be needed to reach the level of protection observed with NCK2187.

Example 8—NCK2187 Promotes the Generation of FoxP3$^+$ Regulatory T Cells (Tregs)

To gain a better understanding of the protective mechanisms induced by *L. acidophilus* SlpA that may explain the aforementioned protection, we orally gavaged healthy control mice with either NCK56 or NCK2187, and analyzed the frequency of Tregs locally and systemically. Compared to untreated or NCK56 treated mice, NCK2187 induced the generation of Tregs (FIG. 14). Taken together, these data suggest that *L. acidophilus* SlpA triggers important regulatory signaling cascades that may enable the restoration of intestinal homeostasis in experimental models of colitis.

Example 9

The human GI tract harbors trillions of microbes, most of which are bacteria (Qin et al., 2010), and are critical determinants to the health of the host (Nicholson et al., 2012; Subramanian et al., 2014). This is especially true in the case of IBD, given the intimate association of the gut microbiota and their gene products with the adjacent colonic tissue (Hold et al., 2014; Huttenhower et al., 2014). Early experiments suggest that susceptibility to pathogenic intestinal inflammation in experimental colitis depends upon the presence of enteric antigens (Kuhn et al., 1993), and were later supported by human studies, which demonstrated that an imbalance in the commensal bacterial composition, termed dysbiosis, is a defining characteristic of patients suffering from IBD (Frank et al., 2007; Sokol et al., 2006). Accordingly, a major focus in the field has been the identification of effector bacterial strains that influence the immune system (Ahern et al., 2014), and thus, may be employed to reprogram undesired immune responses, both locally and systemically.

Search for microbes with immunoregulatory properties at the strain level and not merely at the species level is warranted. Certain embodiments of the current invention identify specific bacterial molecule-host receptor interactions that may account for the responses induced by effector bacterial strains. For example, oral treatment using a *L. acidophilus* strain lacking the gene responsible for LTA biosynthesis significantly reduced pathogenic inflammation in the GI tract, thereby promoting the mitigation of induced colitis (Mohamadzadeh et al., 2011) and the ablation of colonic polyposis (Khazaie et al., 2012). The bacteria lacking LTA and their uses are described in US Patent Application Publication 20130224153, the contents of which are incorporated by reference herein in its entirety. However, a need still remains for identifying other bacterial strains and/or agents useful for treatment of inflammatory diseases, such as colitis or inflammatory bowel disease.

To address this need, the current invention provides bacteria with systematically deleted genes for the construction of novel bacterial strains, for example, NCK2187, and the assignment of roles to sip candidate genes that are responsible for SlpA, SlpB, and SlpX protein expression (Goh et al., 2009). This molecular approach to targeting genes in *L. acidophilus* defined the functional role of SlpA and demonstrated that SlpA affects intestinal innate cells and conventional T cell subset activation, including Tregs, in steady-state and murine colitis models.

As seen in FIGS. 3 and 4, NCK2187 and purified SlpA not only mitigated T cell-induced colitis by significantly reducing inflammation, but also protected the composition of the microbiota and intestinal barrier function. Additionally, systemic immune responses were also altered, whereupon the levels of proinflammatory cytokines, including IL-1β, whose detrimental role in IBD was recently demonstrated (Coccia et al., 2012), decreased significantly. These data suggests the involvement of the IL-1β signaling axis in intestinal protection. Accordingly, gene-screening results, along with SlpA binding to SIGNR3, highlight the involvement of SIGNR3 in the process of tempering highly activated gut immune responses. Additional data regarding SIGNR3 engagement using Signr3$^{-/-}$ mice clarified the role of this signaling molecule in induced immune regulation, as was also documented in the *Leishmania infantum* murine model (Lefevre et al., 2013).

These data reflect that the SlpA:SIGNR3 interaction significantly reduces the high affinity receptors for $LTB_4$ in T cell transferred Rag1$^{-/-}$ mice. Downregulation of $LTB_4$ and/or its receptors is critical in preventing inflammasome activation, which otherwise results in increased IL-1β (Lefevre et al., 2013). Interestingly, interrupting the interaction between SlpA and SIGNR3 resulted in hyperactive immunity and the production of IL-1β in Signr3$^{-/-}$ mice under inflammatory conditions. Such dysregulated immune responses in Signr3$^{-/-}$ mice promoted neutrophil infiltration and significantly affected the function of colonic Tregs, which reverted toward proinflammatory FoxP3$^{+}$ RORγt$^{+}$ Tregs, all of which significantly contributed to pathologic inflammation, a condition seen in IBD progression.

In contrast, balanced immunity was restored in WT mice that were treated with NCK2187 or SlpA. Induced colonic inflammation in WT mice that were treated with NCK56, but not in NCK2187- or SlpA-treated mice, and in KO mice, regardless of treatment, resulted in microbial dysbiosis and barrier dysfunction, another hallmark of IBD.

As such, the current invention indicates that the interaction of SlpA with SIGNR3 can impact the status of innate and T cell polarization in induced colitis. Also, effective modulation of these cellular and molecular factors may significantly modify pathogenic inflammation that results in colitis, and would therefore restore intestinal homeostasis by rebalancing deteriorated immunity, the composition of the gut microbiota, and mucosal barrier function.

Example 10 —A Process for Isolation and Purification of SLPA from *Lactobacillus acidophilus*

It is estimated that over 1 million individuals in the U.S. suffer from IBD (Kappelman et al., 2007; Kappelman et al., 2013). Additionally, ample evidence indicates that dysfunctional immune responses are potentially elicited by gut dysbiosis (Major et al., 2014). To specifically determine the effects of SlpA and its binding to SIGNR3 on intestinal cells and the consequences thereafter, the upp counter-selective knockout strategy (Mohamadzadeh et al., 2011a) was used to generate a new strain of *L. acidophilus*, called NCK2187, which expresses only SlpA Our data show that SlpA plays a critical role in controlling immune responses upon its interaction with SIGNR3, resulting in the diminution of induced colitis, protection of intestinal barrier integrity, and sustenance of the gut bacterial composition. To build upon these observations, we have optimized the purification of SlpA to investigate its physiological effects when orally administrated to mice, and evaluated whether this protein could resist the harsh condition of the gastrointestinal milieu, both important factors that may facilitate the feasibility of potential clinical trials.

Isolation and Detection of L. *Acidophilus* Surface Layer Protein A

S-layers are paracrystalline (glyco) protein arrays that are present in abundance on the cell surface of a subset of eubacteria and archaea. We first sought to improve the process of SlpA isolation and purification. For this purpose, we used sodium chloride (NaCl) (5 M) as discussed in the Materials and Methods section. To avoid non-SlpA protein contamination in our isolation, we employed the LTA-, SlpB-, and SlpX-deficient *L. acidophilus* NCK2187 strain. Visualization of the isolated protein by SDS-PAGE showed a single protein band of the expected size (46 kDa, FIG. 15A). An automated mass spectrometry microbial identification system that uses Matrix Assisted Laser Desorption Ionization Time-of-Flight technology (MALDI-TOF) indicated 97 unique spectra and 55 unique peptides generated post-trypsinization of the protein isolate, which identified two possible proteins [gi|58336516 (SlpA) and gi|362076610 (SlpB)] (FIG. 15B). Further analyses revealed that the peptides generated cover 54% of SlpA and 18% of SlpB (highlighted, FIG. 15C). However, the coverage region of SlpB is shared between SlpA and SlpB (red box, FIG. 15C), and no single unique peptide from SlpB was identified. MALDI-TOF data were analyzed on Scaffold1 (Searle, 2010).26 Therefore, mass spectrometry and SDS-PAGE analyses clearly demonstrated that the identity of the purified SlpA protein was retained whether purified by NaCl or by LiCl (FIG. 15).

Figure 16A:
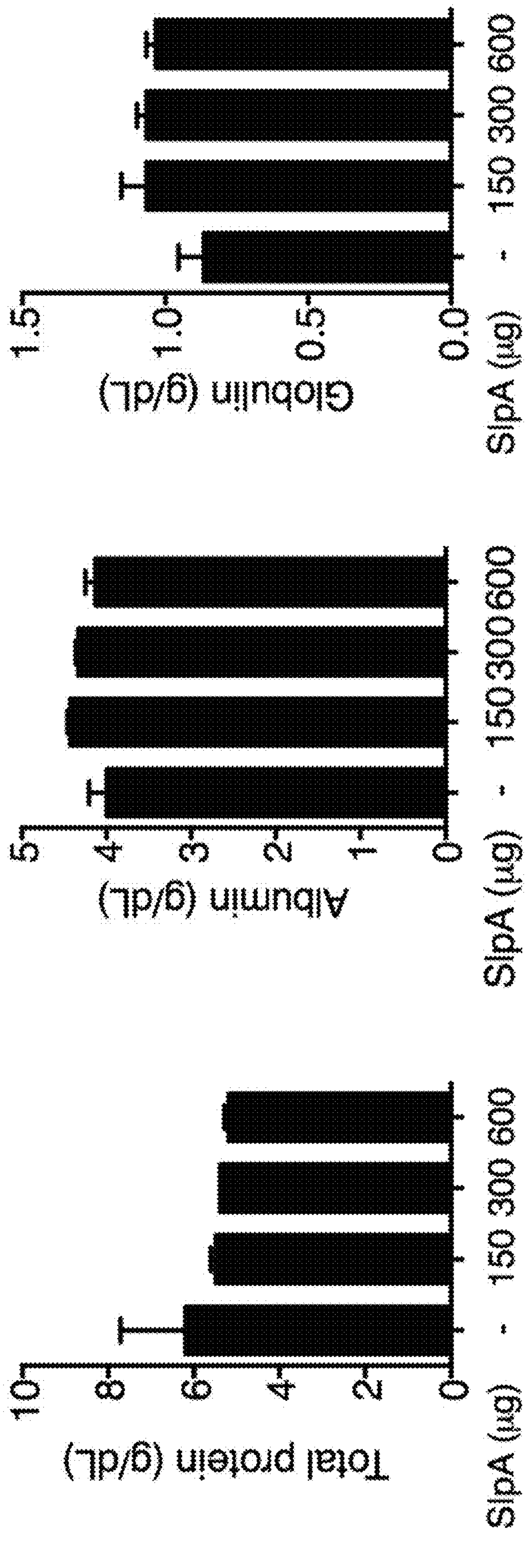
Figure 16B:
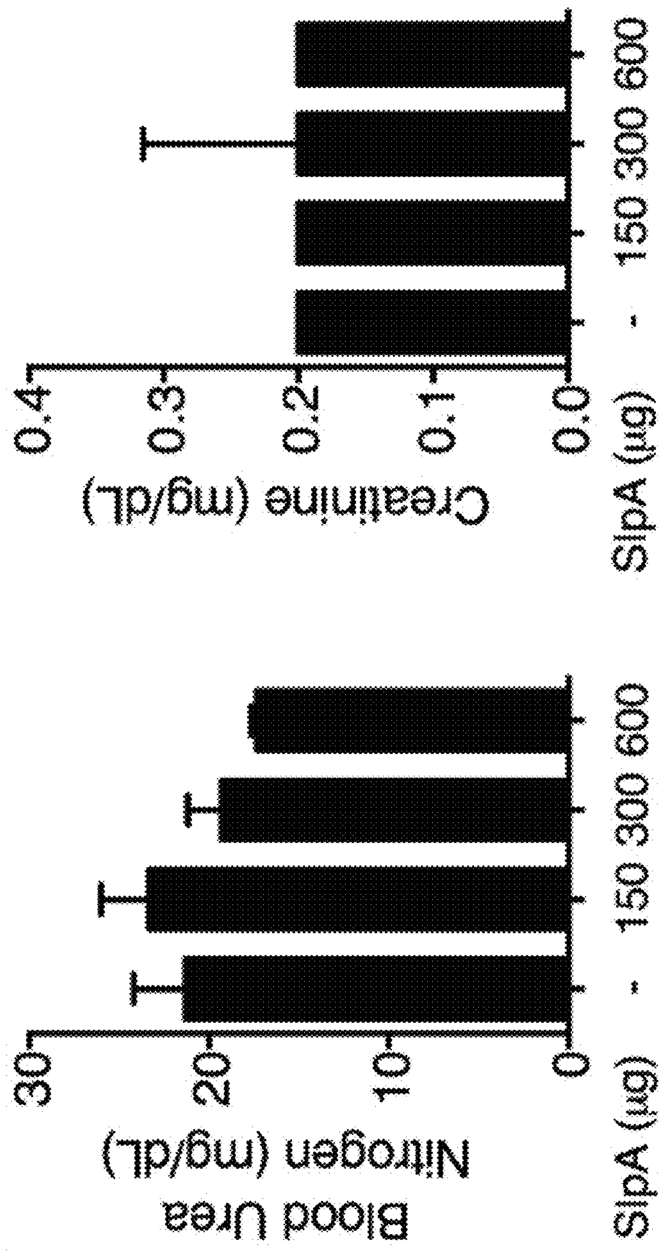
Figure 16C:
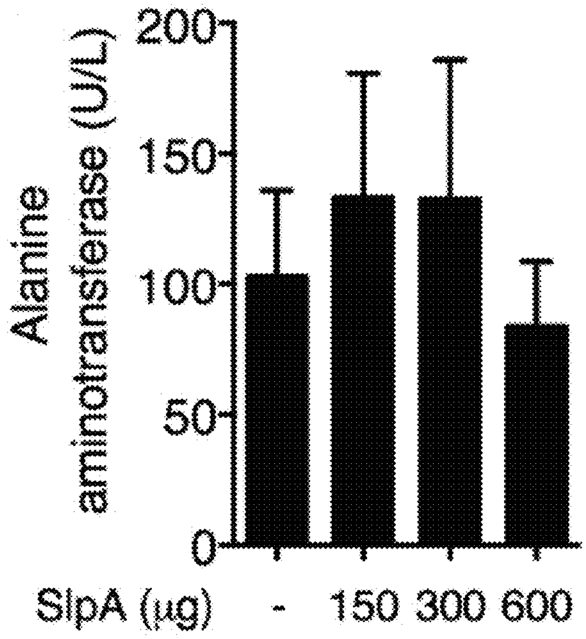
Figure 16D:
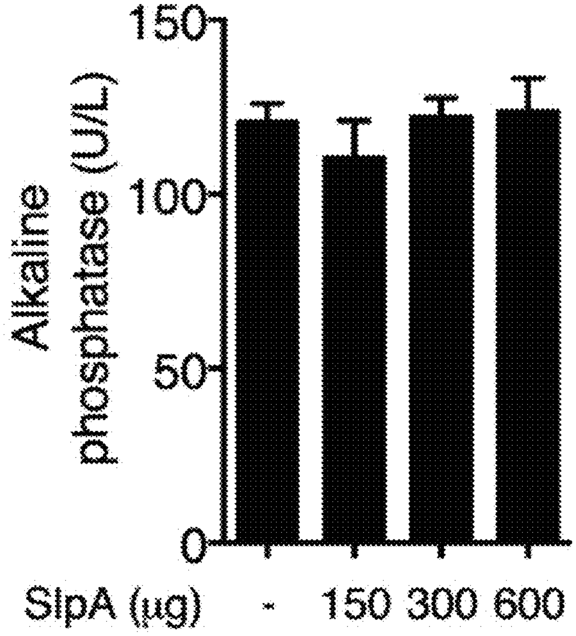
Figure 16E:
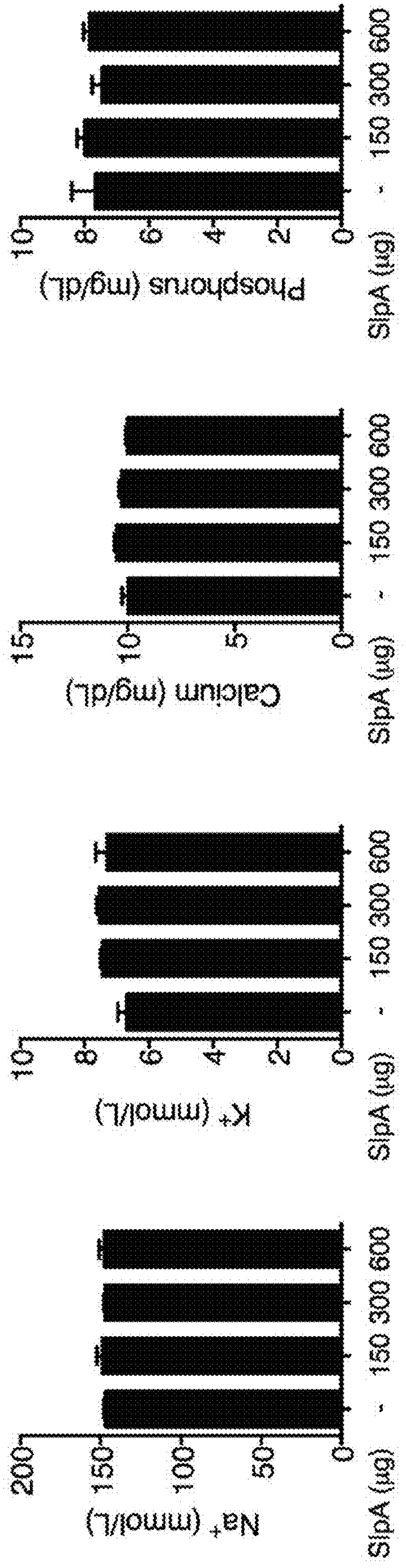

To assess potential toxicity of the isolated SlpA, groups of C57BL/6 mice were then orally gavaged with SlpA (0, 150, 300, 600 μg/100 μL per mouse) every other day for a total of four times. Subsequently, the blood chemistry profiles of these animals were analyzed. Obtained data demonstrated that oral treatment of the mice with varying doses of SlpA did not significantly alter whole blood biochemical values in these animals (FIG. 16). Changes in enzyme activity or concentration of other analytes in the blood were used as metrics of tissue damage or physiologic stress. Various parameters were measured, including total protein and albumin; the concentration of globulins is a calculation based on the aforementioned measurements (FIG. 16A). Function of the urinary system was evaluated by measuring blood levels of urea nitrogen (BUN) and creatinine, which are normally excreted by the kidneys (FIG. 16B). Any evidence of hepatocyte injury was assessed by measuring the activity of the hepatocellular leakage enzyme, alanine aminotransferase (ALT) (FIG. 16C). The production and activity of alkaline phosphatase (ALP), which is associated with biliary epithelial cells and canalicular membranes of cells in the liver (Center, 2007),27 can be seen with solubilization of hepatocyte membranes due to increased bile salts and release of membrane blebs with cellular injury (FIG. 16D) (Thrall et al., 2012).28 The electrolytes, sodium, potassium, calcium, and phosphorus, were also measured to gauge any changes in hydration status, excretional activity, or global cellular damage within the treated mice (FIG. 16E). No statistical differences were found in any of the parameters when comparing the controls and those mice receiving varying doses of SlpA administration, indicating no evidence of toxicity with oral treatment with SlpA in these animals.

Figure 17A:
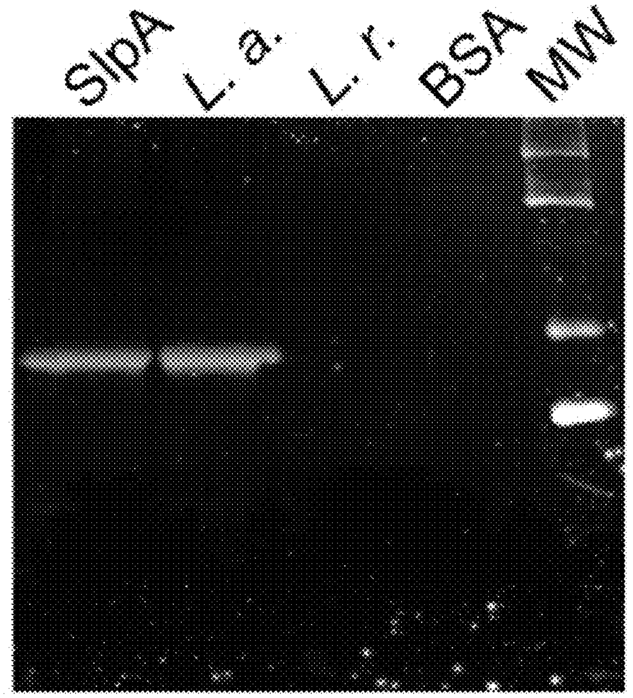
Figure 17B:
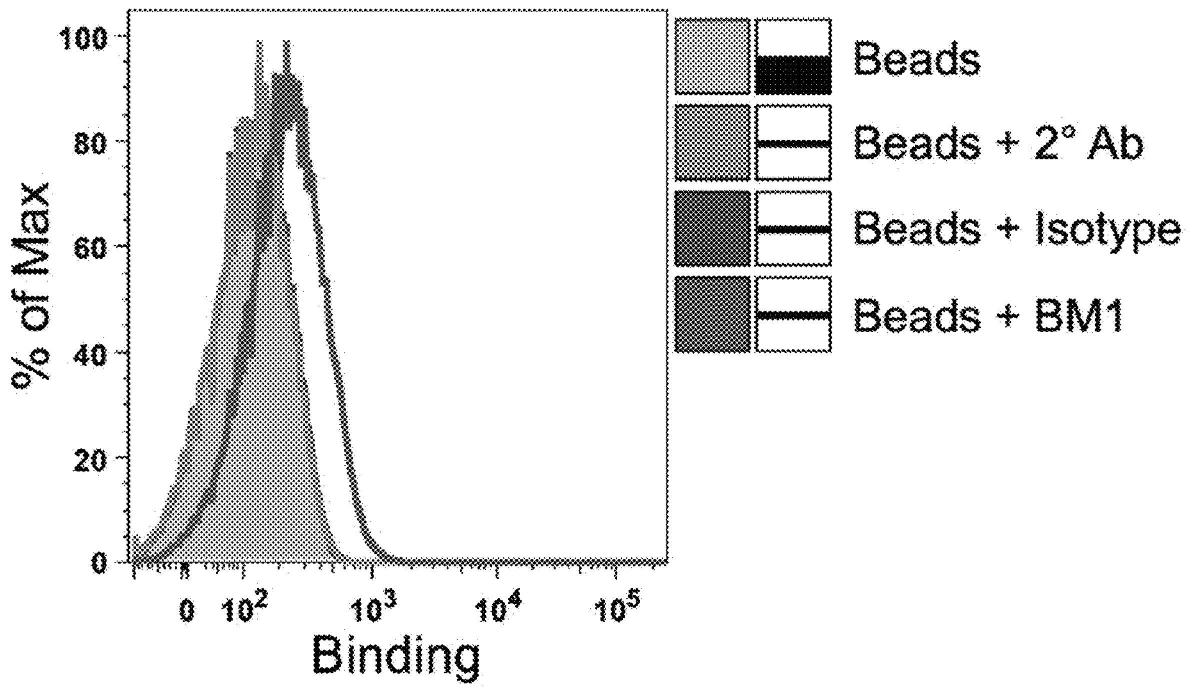
Figure 17C:
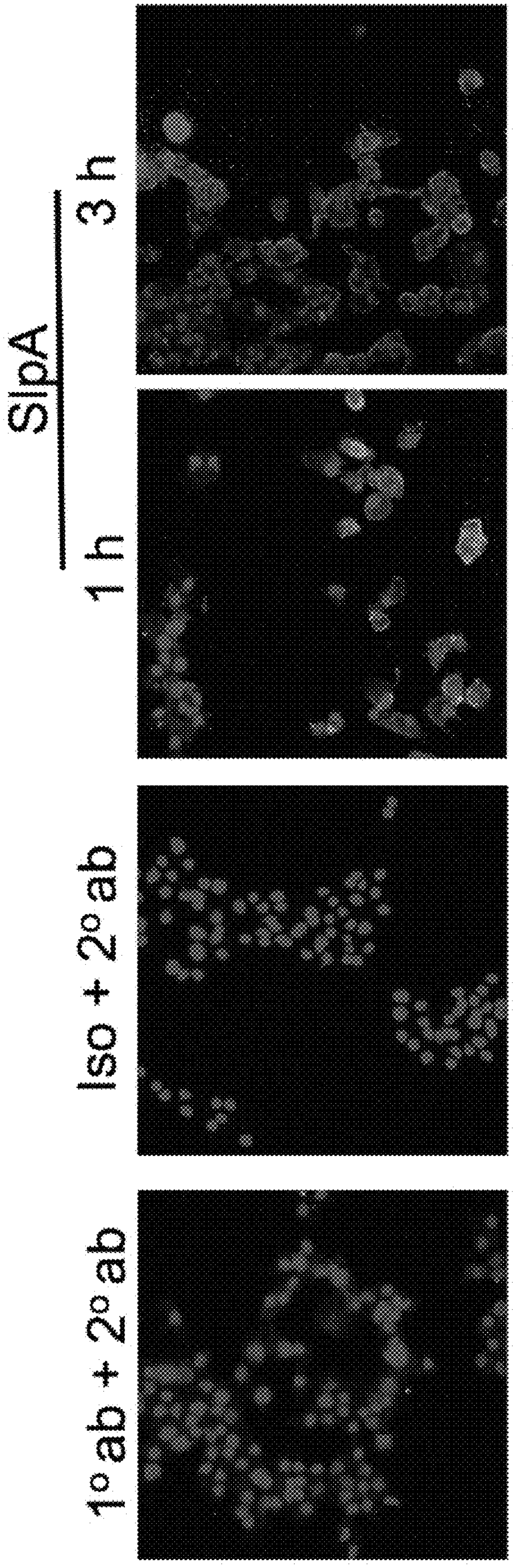
Figure 17D:
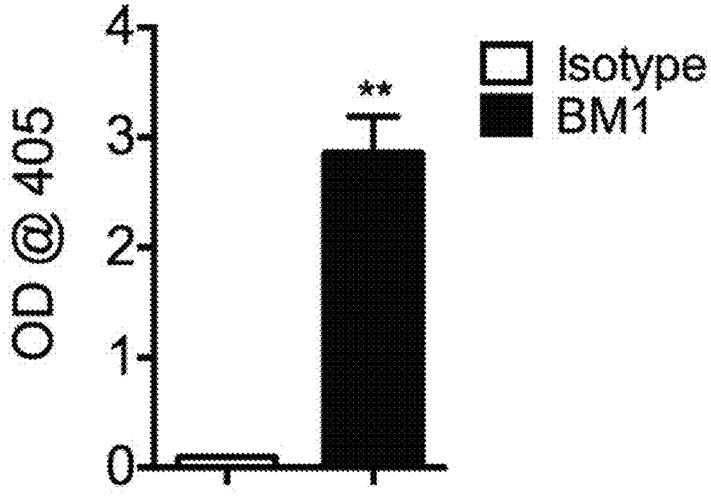
Figure 17E:
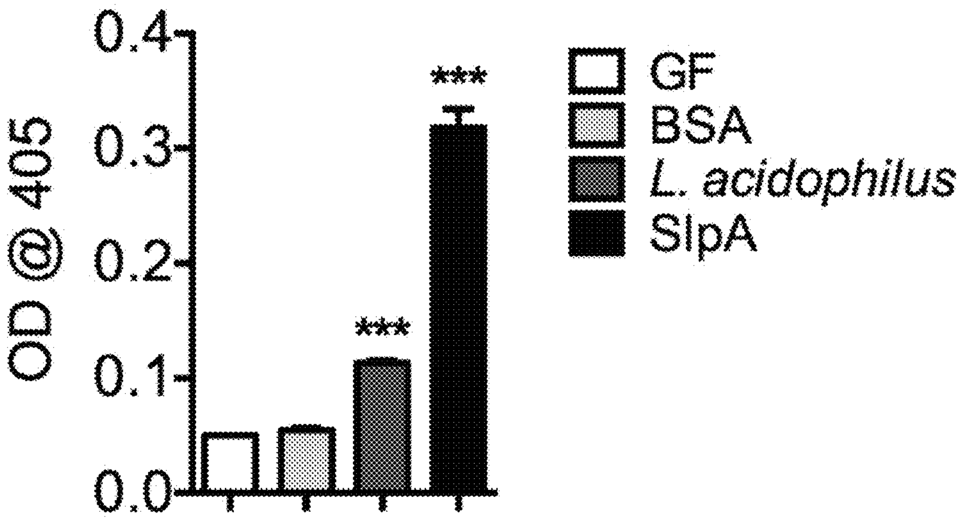

We then elected to generate a specific monoclonal antibody against purified SlpA (Bergeron et al., 2009; Simrell et al., 1979).29, 30 Thus, groups of C57BL/6 mice were immunized with purified SlpA with L. gasseri as an adjuvant for 3 months (every week/100 μg of SlpA). Subsequently, spleen cells were derived to generate hybridoma cells producing monoclonal antibody (mAb) recognizing SlpA. As seen in FIG. 17, the antibody derived from one of our hybridoma cell clones, BM1, recognized SlpA by Western blot (FIG. 17A). Furthermore, this mAb also recognized SlpA on the surface of SlpA-coated beads, and on SlpA-pulsed RAW 264.7 macrophages (FIGS. 17B-C, respectively). As we previously noted significant immunomodulatory effects by purified SlpA in the colon, these data suggested that SlpA dissolved in PBS may resist the hostile acidic milieu of the upper gastrointestinal tract and/or enzymatic degradation within the intestinal lumen. To verify this, we established an ELISA using the mAb, BM1, that can detect SlpA (FIG. 17D). Data clearly show that using this developed ELISA, SlpA can be detected in the fecal samples from mono-associated germ-free B6 mice (FIG. 17E), indicating that SlpA can potentially resist the harsh conditions of the gastrointestinal system. These data may be useful for initiating Phase I clinical trials using NaCl-purified SlpA to demonstrate its ability to potentially downregulate induced colonic inflammation in man.

CONCLUDING REMARKS

To gain further insights into the physiological effects of SlpA, studies have been performed to elucidate the feasibility of Phase I clinical trials using this protein. It appears that SlpA using the newly employed purification method does not elicit potential toxicity when administered orally to animals, and that the structural epitope(s) of this bacterial protein can still be recognized by the mAb generated in our laboratory even after it is excreted through the feces. Nonetheless, further mechanistic studies, such as local and peripheral, targeted and untargeted metabolomics in treated animals, are required to demonstrate the role of SlpA on the host physiology, as well as its effects on other intestinal immune cells, including epithelial cells, colonic B cells, which mount critical humoral immune responses (e.g., IgA), and innate lymphoid cells (ILCs) in steady state and colonic disease.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

```
(Genbank Accession No. AAV42337.1)
                                                         SEQ ID NO: 1
  1 MERTKSFFKW LTQTKLGFFT IVLVLFWLKT YYIYLTKFNL GAVGPMQQFL LLINPIPSGM

 61 LLLGIGLFFK GRKSYWIILI IDFLLTLWLF SNILYYREFS NFLSFSIIKT SGSTSDNLGK

121 SIAGITLASD FLAFLDIAVI IALLATKVIK MDVRPLKLKV SLLIEFLALS LMGLNLLMAQ

181 KDRSGLLTRT FDNNYIVKYL GINEYAIYDG YKTAQTSAQM AKANVSDLKS VRNYLNANKV

241 KPNPEYTGVA KGKNVLVIHL ESFQQFLIGY KWKGKEVTPN LNKIYHQKDT ISFDNFFNQV

301 GQGKTSDAEM MLENSLYGLQ SGSAMSTYGT SNTFESAPAI LHQQAGYTTA VMHGGAGSFW

361 NRNNAYKSFG YQYFMPLSFY ENKPSYYIGY GLKDKIFFDQ SIKYIERLPQ PFYLKMITVT

421 NHYPYDIDKK NQSIAKTNTG DETVDGYVQT AHYLDQAIGE LMSWMKKTGL DKKTLIVFYG

481 DHYGISGNHH KASAQLLKKK SFNDFDNLQF QRVPLMFHMK GLKGGINHTY GGEIDVLPTL

541 LNLLGIKDSD TIQFGYDLLS KNAPQIVAQR NGDFITPEYS KVGSDYYYTK TGKRIKPNKK

601 LKAELTAISN TVTTQLSLSD RVINGNLLRF YRPKWFTKVK PKDYDYNKEP SLKRLFNDPS

661 KTSLWYQNHK KTTQKDFKTD APELKK
```

-continued (Genbank Accession No. YP_193105)

SEQ ID NO: 2

1 MKKNLRIVSA AAAALLAVAP VAASAVSTVN AAAVNAIAVG GSATPLPNNS DVQISSSVAG

61 VTTKNGSSYT NGRISGSINA SYNGTSYSAN FSSSNAGVVV STPGHTELSG EQINGLEPGS

121 AVTVTLRDGV SFNGFSTNAN KTITLAFPKN VSAAGLADAN KVSATSETSV DAGKTIQVKT

181 DKNGVVSFGS AQVLNVKVVE TSDVRAVSFY DIQTGKTVEN GTLSIVAGSN ARANVQEIVN

241 AFNAKYQASQ LNNANSNANV RLTDNNAQAV ATMLRAQNID VDAQGYFTAP ASLSLTFHAE

301 STQNNETAQL PVTVSVTNGK EVTPSTVDSV SKRIMHNAYY YDKDAKRVGT DSVKRYNSVS

361 VLPNTTTING KAYYQVVENG KAVDKYINAA NIDGTKRTLK HNAYVYASSK KRANKVVLKK

421 GEVVTTYGAS YTFKNGQKYY KIGDNTDKTY VKVANFR (Genbank Accession No. YP_193425)

SEQ ID NO: 3

1 MKKNRKMLGL AAATLLAVAP VATSVVPVQA DTAVNVGSAA GTGANTTNTT TQAPQNKPYF

61 TYNNEIIGEA TQSNPLGNVV RTTISFKSDD KVSDLISTIS KAVQFHKNNS ASGENVTINE

121 NDFINQLKAN GVTVKTVQPS NKNEKAYEAI DKVPSTSFNI TLSATGDNNQ TATIQIPMVP

181 QGASTPTDTT QNPQINWTKG GQAQSSSLNG QVFQVAVGSN FNPLNFTNSN GENIIVSAQQ

241 SKNNTTFASI EATSNPVNTS EAGRYYNVTL TATGNTGKKT TATYTVLITS SQKQTLYGNG

301 ESTISTYSIY GNNVLSNSTT FKDGDQVYVS DQTKTVGGVS YSQVSPKSKN DANSSNIWVK

361 TSALVKPAGD TNVKTYPVMV DSRAYDKNGN YLGHMYYAYD NIDIVPTVVT INGKTYYKVA

421 NKDEYVRVTN ITGNQRTLKH NAYIYWSSYR RTPGTGKMYR GQTVTTYGPQ MKFKNGKKYY

481 RIEGCRNNNK RYIKAVNFY (Genbank Accession No. P35829)

SEQ ID NO: 4

1 MKKNLRIVSA AAAALLAVAP VAASAVSTVS AATTINASSS AINTNTNAKY DVDVTPSVSA

61 VAANTANNTP AIAGNLTGTI SASYNGKTYT ANLKADTENA TITAAGSTTA VKPAELAAGV

121 AYTVTVNDVS FNFGSENAGK TVTLGSANSN VKFTGTNSDN QTETNVSTLK VKLDQNGVAS

181 LTNVSIANVY AINTTDNSNV NFYDVTSGAT VTNGAVSVNA DNQGQVNVAN VVAAINSKYF

241 AAQYADKKLN TRTANTEDAI KAALKDQKID VNSVGYFKAP HTFTVNVKAT SNTNGKSATL

301 PVVVTVPNVA EPTVASVSKR IMHNAYYYDK DAKRVGTDSV KRYNSVSVLP NTTTINGKTY

361 YQVVENGKAV DKYINAANID GTKRTLKHNA YVYASSKKRA NKVVLKKGEV VTTYGASYTF

421 KNGQKYYKIG DNTDKTYVKV ANFR

Uniprot Access Number C2HR60

SEQ ID NO: 47

AATTINASSSAINTNTNAKYDVDVTPSVSAVAAVAANTANNTPAIAGNLTGTISASYNGK

TYTANLKADTENATITAAGSTTAVKPAELAAGVAYTVTVNDVSFNFGSENAGKTVTLGSA

NSNVKFTGTNSDNQTETNVSTLKVKLDQNGVASLTNVSIANVYAINTTDNSNVNFYDVTS

GATVTNGAVSVNADNQGQVNVANVVAAINSKYFAAQYADKKLNTRTANTEDAIKAALKDQ

KIDVSNVGYFKAPHTFTVNVKATSNTNGKSATLPVVVTVPNVAEPTVA

Uniprot Access Number P35829

SEQ ID NO: 48

MKKNLRIVSAAAAALLAVAPVAASAVSTVSAATTINASSSAINTNTNAKYDVDVTPSVSA

VAANTANNTPAIAGNLTGTISASYNGKTYTANLKADTENATITAAGSTTAVKPAELAAGV

AYTVTVNDVSFNFGSENAGKTVTLGSANSNVKFTGTNSDNQTETNVSTLKVKLDQNGVAS

LTNVSIANVYAINTTDNSNVNFYDVTSGATVTNGAVSVNADNQGQVNVANVVAAINSKYF

AAQYADKKLNTRTANTEDAIKAALKDQKIDVNSVGYFKAPHTFTVNVKATSNTNGKSATL

PVVVTVPNVAEPTVASVSKRIMHNAYYYDKDAKRVGTDSVKRYNSVSVLPNTTTINGKTY

-continued

YQVVENGKAVDKYINAANIDGTKRTLKHNAYVYASSKKRANKVVLKKGEVVTTYGASYTF

KNGQKYYKIGDNTDKTYVKVANFR

Uniprot Access Number G1UE81

SEQ ID NO: 49

MFGGRKIMQSSLKKSLYLGLAALSFAGVAAVSTTASAKSYATAGAYTTLKTDATKRNVEA

TGTNALYTKPGTVKGAKVVASKATMAKLASSKKSADYFRAYGVKTTNRGSVYYRVVSMDG

KYRGYVYGGKSDTAFAGGIKSADTTTTATTPTRTTGYYLKDVSKNTLWTAPKNTQYKASK

VSLYGVKSTDTFKVDSAATKTREGSLYYHVTDTQNTSVSGWIYAGKGYVAGATTQDLGGL

SLTMSDAAATSDNSVKVVYRASGSQVGTATWVTAAAGTKAGATVGTTAVNAAGVKLADFV

TNSLPSGYTTTGTVDTASATYGNTVYVDVTAAATSKVQLVADNVDNTASTTDNAVAGVLA

NGAKLSSSDLSATLKEAGIKALTGTKGEAIGATNLATISGAFDTAEINGSKTYYAANGDA

YHYVFTYEPANFANDNRLATYGDTLTASFKAVLTKGAPSASSSNSSWIA

Uniprot Access Number Q9Z4J9

SEQ ID NO: 50

MKKNLRIVSAAAAALLAVAPVAASAVSVNAADNTVATTTNTANTVINADGTAINTPADAK

YDVDVTPNLTATAASTVNGQTINGSITGNITASYNGQSYTGTLDTKNGKVSVADSKGTAV

TDFSKLTNGSYTVTVSGVSFNFGTANANKTITLGSKNSNVKFAGADGKFADTVKVELGQN

GTLTTPISVQVSNVNALDLSNANGVNFYNASNGSQVTKGSVNVTAGLIGRLNVSTVASEI

LKNCAAYQVSNGKPVSQLPDQKAVVADVNAALKAANIPVDNAGWFTAPISLSVNVKASSS

INGVGCYFTCTVNVANGKDMTVPSQSKTIMHNAYYYDKDAKRVGTDKLTRYNSVTVAMNT

TTINGKAYYEVIENGKATGKFINADNIDGTKRTLKHNAYVYKTSKKRANKVTLKKGTEVT

TYGGTYTFKNGKQYYKIGNNTDKTYVKASNF

Uniprot Access Number H6VTN4

SEQ ID NO: 51

MKKNLRIVSAAAAALLAVAPVAAAGVSSVTASSIEFVGSSNSSLLPEVNDHTVNFGINFN

AIGAYGNVPSSVSATAEVTINGQKTTINLPENQKSYIYYATTNESVDASKLVAGQKYYTG

INNASLNLGSPNHDKDITLEGSNVSFKTNDSDPYTKTLKVNTDKNGVISNLSIKSANFDA

VDVNNARTVSFYDADTGNIVTSGALEINAGPNAQMNVQTILAKFEQKYQAAQLNNAGTTN

NVSYNNDLISTTPADLAAQLKKAGYSVDNNGYFTAKHSFTVNFSAKSGQNGYTTTMPVTV

TVPNVAEETVPSQIRTVMHNAFFYDKNGKRVGSDKVTRYNSATVAMNTTTIIGKAYYEVI

ENGKATGKFINAANIDGTKRTLKHNAYVYKSSKKRANKVVLKKGETVVTYGGAYTFKNGK

QYYKIGNNTDKTYVKVANF

Uniprot Access Number Q09FM2

SEQ ID NO: 52

MKKNLRIVSAAAAALLAVAPVAASAVSVNAASSSAVQTATNKGTVLPLTDGSTVNVKPNI

SLNTSAYEGVKANISVSFSATVDGTTATSNFTPNASTIELWKNEKNKVTQVTYLQQVTSS

NAGATYQVKMTQVGLNFGSQNANKKVTLTFPEGDMFKTADTSLAQSHEVKLDQNGTITLP

EVVMNVTAKDFANPAVVNWYNTATNAVVSTGNIELFAGSDAGKMNVAQVVSATEKKYHAS

NYGTKANQESSTISYTNNLKDALKAMNVDVDAQGWFVAPKSFTFNMTAKANNNDASSTLA

VTVSVPNGKDMTVPSQSKTVMHNAFFYDKNGKRVGSDKVTRYNSATVAMNTTTINGKAYY

EVIENGKATGKFINAANIDGTKRTLKHNAYVYKSSKKRANKVVLKKGTEVVTYGGAYTFK

NGKQYYKIGNNTDKTYVKVSNF

-continued

Uniprot Access Number L7YE91

SEQ ID NO: 53

```
SVSESKDTVNVTPSFTLTSAIPAKGVPATLQGSIEASLNGTSVTADVADVAKDVTLTDGN

KTVYSYNERENKVDNNLSAVEASKEYTMTLSGVGFSFGKANAGKTLTFKLPKNVKVNDTS

NDVKVSLDQYGNATNLKFVISNIKAYDSANTNAVSFYAAKSGLVATQGSYMTLADENGNL

NVNTLLDKLKGKYEAMQFKDSKFETVNVNTTADDVKAELEKAGIKVDAANNFEAPDTFTV

TLNAKSDVNGKTASLPVVVTVPNGKSTVVPSQSKTIMHNAYYYDKDAKRVGTDKVTRYNA

VTVAMNTTKLANGISYYEVIEN
```

Uniprot Access Number K8DVK7

SEQ ID NO: 54

```
ADSAINANTNAKYDVDVTPSISAIAAVAKSDTMPAIPGSLTGSISASYNGKSYTANLPKD

SGNATITDSNNNTVKPAKLEADKAYTVTVPDVSFNFGSENAGKVITIGSANPNVTFTKKT

GDQPASTVKVTLDQDGVAKLSSVQIKNVYAIDTTYNSNVNFYDVTTGAIVTTGAVSIDAD

NQGQLNITSVVAAINSKYFAAQYDKKQLTNDVTFDTETAVKDALKAQKIEVSSVGYFKAP

HTFTVNVKATSNKNGKSATLPVTVTVPNVADPVVPSQSKTIMHNAYFYDKDAKRVGTDKV

TRYNTVTVAMNTTKLANGISYYEVIENGKA
```

Uniprot Access Number F0NUB7

SEQ ID NO: 55

```
MDHVSKGFVHYRLLSHAEPMAYYIFYISRRKDHMKKNLRIVSAAAAALLAVAPVAATAMP

VNAATTINADSAINANTNAKYDVDVTPSISAIAKVTGSATIPGSLTGSISASYNGKSYTA

NLPKDSGNATIADKHGNPVKPADLEADKAYTVTVPDVSFNFGSENAGKEITIGSANQNVT

FTTKDSQSGSTVSGSTVKVTLDQDGVAKLSSVQIKDVYAIDTTYNSNVNFYDVTTGAIVT

TGAVSIDADNQGQLNTASVVAAISSKYFAAQYADKNLTSDNVTYNIETAVKDALKAQKIE

VSSVGYFKAPHTFTVNVKATSNKNGKSATLPVTVTVPNVADPVVPSQSKTIMHNAYFYDK

DAKRVGTDKVTRYNTVTVAMNTTKLANGISYYEVIENGKATGKYINADNIDGTKRTLKHN

AYVYKTSKKRANKVVLKKGTEVTTYGGSYKFKNGKKYYKIGADTKKTYVRVENFD
```

REFERENCES

Ahern, P. P., Faith, J. J., and Gordon, J. I. (2014). Mining the Human Gut Microbiota for Effector Strains that Shape the Immune System. Immunity 40, 815-823.

Atarashi, K., Tanoue, T., Oshima, K., Suda, W., Nagano, Y., Nishikawa, H., Fukuda, S., Saito, T., Narushima, S., Hase, K., et al. (2013). Treg induction by a rationally selected mixture of Clostridia strains from the human microbiota. Nature 500, 232-236.

Avall-Jaaskelainen, S., Lindholm, A., Palva, A. (2003). Surface display of the receptor-binding region of the *Lactobacillus brevis* S-layer protein in *Lactococcus lactis* provides nonadhesive lactococci with the ability to adhere to intestinal epithelial cells. Appl Environ Microbiol; 69:2230-6.

Avall-Jaaskelainen, S., Palva, A. (2005). *Lactobacillus* surface layers and their applications. FEMS Microbiol Rev; 29:511-29.

Belkaid, Y., Hand, T. W. (2014). Role of the microbiota in immunity and inflammation. Cell; 157:121-41.

Bergeron, R. J., Bharti, N., Singh, S., McManis, J. S., Wiegand, J., Green, L. G. (2009). Vibriobactin antibodies: a vaccine strategy. J Med Chem; 52:3801-13.

Center, S. A. (2007). Interpretation of liver enzymes. Vet Clin North Am Small Anim Pract; 37:297-333, vii.

Cheng, S. X., Lightfoot, Y. L., Yang, T., Zadeh, M., Tang, L., Sahay, B., Wang, G. P., Owen, J. L., and Mohamadzadeh, M. (2014). Epithelial CaSR deficiency alters intestinal integrity and promotes proinflammatory immune responses. FEBS Lett.

Coccia, M., Harrison, O. J., Schiering, C., Asquith, M. J., Becher, B., Powrie, F., and Maloy, K. J. (2012). IL-1β mediates chronic intestinal inflammation by promoting the accumulation of IL-17A secreting innate lymphoid cells and CD4(+) Th17 cells. J Exp Med 209, 1595-1609.

Ehlers, S. (2010). DC-SIGN and mannosylated surface structures of *Mycobacterium tuberculosis*: a deceptive liaison. Eur J Cell Biol 89, 95-101.

Engering, A., Geijtenbeek, T. B., and van Kooyk, Y. (2002). Immune escape through C-type lectins on dendritic cells. Trends Immunol 23, 480-485.

Eriksson, M., Johannssen, T., von Smolinski, D., Gruber, A. D., Seeberger, P. H., and Lepenies, B. (2013). The C-Type Lectin Receptor SIGNR3 Binds to Fungi Present in Commensal Microbiota and Influences Immune Regulation in Experimental Colitis. Front Immunol 4, 196.

Frank, D. N., St Amand, A. L., Feldman, R. A., Boedeker, E. C., Harpaz, N., and Pace, N. R. (2007). Molecular-phylogenetic characterization of microbial community imbalances in human inflammatory bowel diseases. Proc Natl Acad Sci USA 104, 13780-13785.

Geremia, A., Biancheri, P., Allan, P., Corazza, G. R., and Di Sabatino, A. (2014). Innate and adaptive immunity in inflammatory bowel disease. Autoimmun Rev; 13:3-10.

Goh, Y. J., Azcarate-Peril, M. A., O'Flaherty, S., Durmaz, E., Valence, F., Jardin, J., Lortal, S., and Klaenhammer, T. R. (2009). Development and application of a upp-based counterselective gene replacement system for the study of the S-layer protein SlpX of *Lactobacillus acidophilus* NCFM. Appl Environ Microbiol 75, 3093-3105.

Hold, G. L., Smith, M., Grange, C., Watt, E. R., El-Omar, E. M., and Mukhopadhya, I. (2014). Role of the gut microbiota in inflammatory bowel disease pathogenesis: what have we learnt in the past 10 years? World J Gastroenterol 20, 1192-1210.

Hovhannisyan, Z., Treatman, J., Littman, D. R., and Mayer, L. (2011). Characterization of interleukin-17-producing regulatory T cells in inflamed intestinal mucosa from patients with inflammatory bowel diseases. Gastroenterology 140, 957-965.

Huttenhower, C., Kostic, A. D., and Xavier, R. J. (2014). Inflammatory Bowel Disease as a Model for Translating the Microbiome. Immunity 40, 843-854.

Iliev, I. D., Funari, V. A., Taylor, K. D., Nguyen, Q., Reyes, C. N., Strom, S. P., Brown, J., Becker, C. A., Fleshner, P. R., Dubinsky, M., et al. (2012). Interactions between commensal fungi and the C-type lectin receptor Dectin-1 influence colitis. Science 336, 1314-1317.

Ivanov, I. I., and Honda, K. (2012). Intestinal commensal microbes as immune modulators. Cell Host Microbe 12, 496-508.

Johnson, B., Selle, K., O'Flaherty, S., Goh, Y. J., and Klaenhammer, T. (2013). Identification of extracellular surface-layer associated proteins in *Lactobacillus acidophilus* NCFM. Microbiology 159, 2269-2282.

Kappelman, M. D., Moore, K. R., Allen, J. K., Cook, S. F. (2013). Recent trends in the prevalence of Crohn's disease and ulcerative colitis in a commercially insured US population. Dig Dis Sci; 58:519-25.

Kappelman, M. D., Rifas-Shiman S L, Kleinman K, Ollendorf D, Bousvaros A, Grand R J, et al. (2007). The prevalence and geographic distribution of Crohn's disease and ulcerative colitis in the United States. Clinical gastroenterology and hepatology: the official clinical practice journal of the American Gastroenterological Association; 5:1424-9.

Khazaie, K., Zadeh, M., Khan, M. W., Bere, P., Gounari, F., Dennis, K., Blatner, N. R., Owen, J. L., Klaenhammer, T. R., and Mohamadzadeh, M. (2012). Abating colon cancer polyposis by *Lactobacillus acidophilus* deficient in lipoteichoic acid. Proc Natl Acad Sci USA 109, 10462-10467.

Konstantinov, S. R., Smidt, H., de Vos, W. M., Bruijns, S. C., Singh, S. K., Valence, F., Molle, D., Lortal, S., Altermann, E., Klaenhammer, T. R., et al. (2008a). S layer protein A of *Lactobacillus acidophilus* NCFM regulates immature dendritic cell and T cell functions. Proc Natl Acad Sci USA 105, 19474-19479.

Konstantinov, S.R., Smidt, H., Akkermans, A.D., Casini, L., Trevisi. P., Mazzoni, M., et al (2008b). Feeding of *Lactobacillus sobrius* reduces *Escherichia coli* F4 levels in the gut and promotes growth of infected piglets. FEMS Microbiol Ecol; 66:599-607.

Khan, M. W., Zadeh, M., Bere, P., Gounaris, E., Owen, J., Klaenhammer, T., et al (2012). Modulating intestinal immune responses by lipoteichoic acid-deficient *Lactobacillus acidophilus*. Immunotherapy; 4:151-61.

Kuhn, R., Lohler, J., Rennick, D., Rajewsky, K., and Muller, W. (1993). Interleukin-10-deficient mice develop chronic enterocolitis. Cell 75, 263-274.

Lee, Y. K., Mazmanian, S. K. (2010). Has the microbiota played a critical role in the evolution of the adaptive immune system? Science; 330:1768-73.

Lefevre, L., Lugo-Villarino, G., Meunier, E., Valentin, A., Olagnier, D., Authier, H., Duval, C., Dardenne, C., Bernad, J., Lemesre, J. L., et al. (2013). The C-type lectin receptors dectin-1, MR, and SIGNR3 contribute both positively and negatively to the macrophage response to *Leishmania infantum*. Immunity 38, 1038-1049.

Ley, R. E., Peterson, D. A., and Gordon, J. I. (2006). Ecological and evolutionary forces shaping microbial diversity in the human intestine. Cell 124, 837-848.

Lightfoot, Y. L., Yang, T., Sahay, B., Mohamadzadeh, M. (2012). Targeting aberrant colon cancer-specific DNA methylation with lipoteichoic acid-deficient *Lactobacillus acidophilus*. Gut Microbes; 4.

Lightfoot, Y. L., and Mohamadzadeh, M. (2013). Tailoring gut immune responses with lipoteichoic acid-deficient *Lactobacillus acidophilus*. Front Immunol 4, 25.

Lightfoot, Y. L., Yang, T., Sahay, B., Zadeh, M., Cheng, S. X., Wang, G. P., Owen, J. L., and Mohamadzadeh, M. (2014). Colonic Immune Suppression, Barrier Dysfunction, and Dysbiosis by Gastrointestinal *Bacillus anthracis* Infection. PLoS One 9, e100532.

Lightfoot Y L, Selle K, Yang T, Goh Y J, Sahay B, Zadeh M, et al. (2015). SIGNR3-dependent immune regulation by *Lactobacillus acidophilus* surface layer protein A in colitis. EMBO J.; 34(7):829-973.

Major, G., Spiller, R. (2014). Irritable bowel syndrome, inflammatory bowel disease and the microbiome. Curr Opin Endocrinol Diabetes Obes; 21:15-21.

Maslowski, K. M., and Mackay, C. R. (2011). Diet, gut microbiota and immune responses. Nat Immunol 12, 5-9.

McDermott, A. J., and Huffnagle, G. B. (2014). The microbiome and regulation of mucosal immunity. Immunology 142, 24-31.

Mohamadzadeh, M., Pfeiler, E. A., Brown, J. B., Zadeh, M., Gramarossa, M., Managlia, E., Bere, P., Sarraj, B., Khan, M. W., Pakanati, K. C., et al. (2011a). Regulation of induced colonic inflammation by *Lactobacillus acidophilus* deficient in lipoteichoic acid. Proc Natl Acad Sci USA 108 Suppl 1, 4623-4630.

Mohamadzadeh, M., Owen, J. L. (201 b). Reprogramming intestinal immunity is the answer to induced pathogenic inflammation. Immunotherapy; 3:1415-7.

Napolitano, L. M., Koruda, M. J., Meyer, A. A., and Baker, C. C. (1996). The impact of femur fracture with associated soft tissue injury on immune function and intestinal permeability. Shock 5, 202-207.

Neurath, M. F. (2014). Cytokines in inflammatory bowel disease. Nat Rev Immunol 14, 329-342.

Nicholson, J. K., Holmes, E., Kinross, J., Burcelin, R., Gibson, G., Jia, W., and Pettersson, S. (2012). Host-gut microbiota metabolic interactions. Science 336, 1262-1267.

Osorio, F., and Reis e Sousa, C. (2011). Myeloid C-type lectin receptors in pathogen recognition and host defense. Immunity 34, 651-664.

Powlesland, A. S., Ward, E. M., Sadhu, S. K., Guo, Y., Taylor, M. E., and Drickamer, K. (2006). Widely divergent biochemical properties of the complete set of mouse DC-SIGN-related proteins. The Journal of biological chemistry 281, 20440-20449.

Qin, J., Li, R., Raes, J., Arumugam, M., Burgdorf, K. S., Manichanh, C., Nielsen, T., Pons, N., Levenez, F., Yamada, T., et al. (2010). A human gut microbial gene catalogue established by metagenomic sequencing. Nature 464, 59-65.

Saber, R., Zadeh, M., Pakanati, K. C., Bere, P., Klaenhammer, T., Mohamadzadeh, M. (2011). Lipoteichoic acid-deficient *Lactobacillus acidophilus* regulates downstream signals. Immunotherapy 2011; 3:337-47.

Sara, M., Sleytr, U. B. (2000). S-Layer proteins. J Bacteriol; 182:859-68.

Saunders, S. P., Barlow, J. L., Walsh, C. M., Bellsoi, A., Smith, P., McKenzie, A. N., and Fallon, P. G. (2010). C-type lectin SIGN-R1 has a role in experimental colitis and responsiveness to lipopolysaccharide. J Immunol 184, 2627-2637.

Searle B C. (2010). Scaffold: a bioinformatic tool for validating MS/MS-based proteomic studies. Proteomics; 10:1265-9.

Simrell, C. R., Klein, P. A. (1979). Antibody responses of tumor-bearing mice to their own tumors captured and perpetuated as hybridomas. J Immunol; 123:2386-94.

Snelgrove, R. J., Jackson, P. L., Hardison, M. T., Noerager, B. D., Kinloch, A., Gaggar, A., Shastry, S., Rowe, S. M., Shim, Y. M., Hussell, T., et al. (2010). A critical role for LTA4H in limiting chronic pulmonary neutrophilic inflammation. Science 330, 90-94.

Sokol, H., Seksik, P., Rigottier-Gois, L., Lay, C., Lepage, P., Podglajen, I., Marteau, P., and Doré, J. (2006). Specificities of the fecal microbiota in inflammatory bowel disease. Inflamm Bowel Dis 12, 106-111.

Subramanian, S., Huq, S., Yatsunenko, T., Haque, R., Mahfuz, M., Alam, M. A., Benezra, A., DeStefano, J., Meier, M. F., Muegge, B. D., et al. (2014). Persistent gut microbiota immaturity in malnourished Bangladeshi children. Nature 509, 417-421.

Tanne, A., Ma, B., Boudou, F., Tailleux, L., Botella, H., Badell, E., Levillain, F., Taylor, M. E., Drickamer, K., Nigou, J., et al. (2009). A murine DC-SIGN homologue contributes to early host defense against *Mycobacterium tuberculosis*. J Exp Med 206, 2205-2220.

Thrall, M. A., Weiser, G., Allison, R. W., Campbell, T. W., eds (2012). Veterinary Hematology and Clinical Chemistry. Ames, Iowa: Wiley-Blackwell.

Tobin, D. M., Vary, J. C., Jr., Ray, J. P., Walsh, G. S., Dunstan, S. J., Bang, N. D., Hagge, D. A., Khadge, S., King, M. C., Hawn, T. R., et al. (2010). The lta4h locus modulates susceptibility to mycobacterial infection in zebrafish and humans. Cell 140, 717-730.

Underhill, D. M., Ozinsky, A. (2002). Toll-like receptors: key mediators of microbe detection. Curr Opin Immunol; 14:103-10.

van Kooyk, Y., and Geijtenbeek, T. B. (2003). DC-SIGN: escape mechanism for pathogens. Nat Rev Immunol 3, 697-709.

Varley, K. E., Mitra, R. D. (2010). Bisulfite Patch PCR enables multiplexed sequencing of promoter methylation across cancer samples. Genome Res; 20:1279-87.

Weis, W. I., Taylor, M. E., Drickamer, K. (1998). The C-type lectin superfamily in the immune system. Immunol Rev; 163:19-34.

Yang, T., Owen, J. L., Lightfoot, Y. L., Kladde, M. P., Mohamadzadeh, M. (2013). Microbiota impact on the epigenetic regulation of colorectal cancer. Trends Mol Med; 19:714-25.

Yang, Y., Torchinsky, M. B., Gobert, M., Xiong, H., Xu, M., Linehan, J. L., Alonzo, F., Ng, C., Chen, A., Lin, X., et al. (2014). Focused specificity of intestinal TH17 cells towards commensal bacterial antigens. Nature 510, 152-156.

Zadeh, M., Khan, M. W., Goh, Y. J., Selle, K., Owen, J. L., Klaenhammer, T., et al (2012). Induction of intestinal proinflammatory immune responses by lipoteichoic acid. J Inflamm (Lond); 9:7.

We claim:

1. A method of treating an inflammatory disease of the gastrointestinal system in a subject having said inflammatory disease, the method comprising orally administering a therapeutically effective amount of a recombinant lactic acid bacterium or a composition comprising said recombinant lactic acid bacterium to the subject, wherein the inflammatory disease of the gastrointestinal system is inflammatory bowel disease and said bacterium is:

a) genetically modified to eliminate the display of lipoteichoic acid (LTA) on its surface by eliminating the expression of phosphoglycerol transferase protein, to eliminate the display of surface layer protein B (SlpB) and surface layer protein X (SlpX) on the surface of said bacterium and to express surface layer protein A (SlpA) on its surface, wherein the SlpA has the amino acid sequence of SEQ ID NO: 4, the SlpB has the amino acid sequence of SEQ ID NO: 2 or an amino acid sequence at least 95% identical thereto, the SlpX has the amino acid sequence of SEQ ID NO: 3 or an amino acid sequence at least 95% identical thereto, and the phosphoglycerol transferase protein has the amino acid sequence of SEQ ID NO: 1 or an amino acid sequence at least 95% identical thereto; or b) lacking expression of LTA, SlpB and SlpX on the surface of said bacterium and is genetically modified to express SlpA on its surface, wherein the SlpA has the amino acid sequence of SEQ ID NO: 4, the SlpB has the amino acid sequence of SEQ ID NO: 2 or an amino acid sequence at least 95% identical thereto, the SlpX has the amino acid sequence of SEQ ID NO: 3 or an amino acid sequence at least 95% identical thereto, and the phosphoglycerol transferase protein has the amino acid sequence of SEQ ID NO: 1 or an amino acid sequence at least 95% identical thereto.

2. The method of claim 1, wherein the inflammatory bowel disease is ulcerative colitis.

3. The method of claim 1, wherein the inflammatory bowel disease is Crohn's disease.

4. The method of claim 1, wherein said bacterium is genetically modified to eliminate the display of the lipoteichoic acid (LTA) on its surface by eliminating the expression of the phosphoglycerol transferase protein, to eliminate the display of the surface layer protein B (SlpB) and the surface layer protein X (SlpX) on the surface of said bacterium and to express the surface layer protein A (SlpA) on its surface, wherein the SlpA has the amino acid sequence of SEQ ID NO: 4, the SlpB has the amino acid sequence of SEQ ID NO: 2 or an amino acid sequence at least 95% identical thereto, the SlpX has the amino acid sequence of SEQ ID NO: 3 or an amino acid sequence at least 95% identical thereto, and the phosphoglycerol transferase protein has the amino acid sequence of SEQ ID NO: 1 or an amino acid sequence at least 95% identical thereto.

5. The method of claim 1, said bacterium lacking expression of the LTA, the SlpB and the SlpX on the surface of said bacterium and is genetically modified to express the SlpA on its surface, wherein the SlpA has the amino acid sequence of SEQ ID NO: 4, the SlpB has the amino acid sequence of SEQ ID NO: 2 or an amino acid sequence at least 95% identical thereto, the SlpX has the amino acid sequence of SEQ ID NO: 3 or an amino acid sequence at least 95% identical thereto, and the phosphoglycerol transferase protein has the amino acid sequence of SEQ ID NO: 1 or an amino acid sequence at least 95% identical thereto.

* * * * *

UNITED STATES PATENT AND TRADEMARK OFFICE

CERTIFICATE OF CORRECTION

PATENT NO. : 11,098,088 B2
APPLICATION NO. : 16/790793
DATED : August 24, 2021
INVENTOR(S) : Yaima L. Lightfoot, Bikash Sahay and Mansour Mohamadzadeh It is certified that error appears in the above-identified patent and that said Letters Patent is hereby corrected as shown below:

In the Specification

Column 2,
Line 18, "(MPs)" should read --(MΦs)--.

Column 5,
Line 9, "IL-β" should read --IL-1β--.

Column 5,
Line 64, "IL-113" should read --IL-1β--.

Column 7,
Line 19, "gi|158336516" should read --gi|58336516--.

Column 33,
Line 54, "MKKNLRIVSAAAAALLAVAPVAASAVSVNAASSSAVQTATNKGT VLPLTDGSTVNVKPNI" should read --MKKNLRIVSAAAAALLAVAPVAASA VSVNAASSSAVQTATNIGTVLPLTDGSTVNVKPNI--.

Column 38,
Line 45, "(201 b)" should read --(2011b)--.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 56

<210> SEQ ID NO 1
<211> LENGTH: 686
<212> TYPE: PRT
<213> ORGANISM: Lactobacillus acidophilus
<220> FEATURE:
<221> NAME/KEY: MISC_FEATURE
<223> OTHER INFORMATION: Amino acid sequence of phosphoglycerol
      transferase protein

<400> SEQUENCE: 1

Met Glu Arg Thr Lys Ser Phe Phe Lys Trp Leu Thr Gln Thr Lys Leu
1               5                   10                  15

Gly Phe Phe Thr Ile Val Leu Val Leu Phe Trp Leu Lys Thr Tyr Tyr
            20                  25                  30

Ile Tyr Leu Thr Lys Phe Asn Leu Gly Ala Val Gly Pro Met Gln Gln
        35                  40                  45

Phe Leu Leu Leu Ile Asn Pro Ile Pro Ser Gly Met Leu Leu Leu Gly
    50                  55                  60

Ile Gly Leu Phe Phe Lys Gly Arg Lys Ser Tyr Trp Ile Ile Leu Ile
65                  70                  75                  80

Ile Asp Phe Leu Leu Thr Leu Trp Leu Phe Ser Asn Ile Leu Tyr Tyr
                85                  90                  95

Arg Glu Phe Ser Asn Phe Leu Ser Phe Ser Ile Ile Lys Thr Ser Gly
```

-continued

```
            100                 105                 110

Ser Thr Ser Asp Asn Leu Gly Lys Ser Ile Ala Gly Ile Thr Leu Ala
        115                 120                 125

Ser Asp Phe Leu Ala Phe Leu Asp Ile Ala Val Ile Ile Ala Leu Leu
    130                 135                 140

Ala Thr Lys Val Ile Lys Met Asp Val Arg Pro Leu Lys Leu Lys Val
145                 150                 155                 160

Ser Leu Leu Ile Glu Phe Leu Ala Leu Ser Leu Met Gly Leu Asn Leu
                165                 170                 175

Leu Met Ala Gln Lys Asp Arg Ser Gly Leu Leu Thr Arg Thr Phe Asp
            180                 185                 190

Asn Asn Tyr Ile Val Lys Tyr Leu Gly Ile Asn Glu Tyr Ala Ile Tyr
        195                 200                 205

Asp Gly Tyr Lys Thr Ala Gln Thr Ser Ala Gln Met Ala Lys Ala Asn
    210                 215                 220

Val Ser Asp Leu Lys Ser Val Arg Asn Tyr Leu Asn Ala Asn Lys Val
225                 230                 235                 240

Lys Pro Asn Pro Glu Tyr Thr Gly Val Ala Lys Gly Lys Asn Val Leu
                245                 250                 255

Val Ile His Leu Glu Ser Phe Gln Gln Phe Leu Ile Gly Tyr Lys Trp
            260                 265                 270

Lys Gly Lys Glu Val Thr Pro Asn Leu Asn Lys Ile Tyr His Gln Lys
        275                 280                 285

Asp Thr Ile Ser Phe Asp Asn Phe Phe Asn Gln Val Gly Gln Gly Lys
    290                 295                 300

Thr Ser Asp Ala Glu Met Met Leu Glu Asn Ser Leu Tyr Gly Leu Gln
305                 310                 315                 320

Ser Gly Ser Ala Met Ser Thr Tyr Gly Thr Ser Asn Thr Phe Glu Ser
                325                 330                 335

Ala Pro Ala Ile Leu His Gln Gln Ala Gly Tyr Thr Thr Ala Val Met
            340                 345                 350

His Gly Gly Ala Gly Ser Phe Trp Asn Arg Asn Asn Ala Tyr Lys Ser
        355                 360                 365

Phe Gly Tyr Gln Tyr Phe Met Pro Leu Ser Phe Tyr Glu Asn Lys Pro
    370                 375                 380

Ser Tyr Tyr Ile Gly Tyr Gly Leu Lys Asp Lys Ile Phe Phe Asp Gln
385                 390                 395                 400

Ser Ile Lys Tyr Ile Glu Arg Leu Pro Gln Pro Phe Tyr Leu Lys Met
                405                 410                 415

Ile Thr Val Thr Asn His Tyr Pro Tyr Asp Ile Asp Lys Lys Asn Gln
            420                 425                 430

Ser Ile Ala Lys Thr Asn Thr Gly Asp Glu Thr Val Asp Gly Tyr Val
        435                 440                 445

Gln Thr Ala His Tyr Leu Asp Gln Ala Ile Gly Glu Leu Met Ser Trp
    450                 455                 460

Met Lys Lys Thr Gly Leu Asp Lys Lys Thr Leu Ile Val Phe Tyr Gly
465                 470                 475                 480

Asp His Tyr Gly Ile Ser Gly Asn His His Lys Ala Ser Ala Gln Leu
                485                 490                 495

Leu Lys Lys Lys Ser Phe Asn Asp Phe Asp Asn Leu Gln Phe Gln Arg
            500                 505                 510

Val Pro Leu Met Phe His Met Lys Gly Leu Lys Gly Gly Ile Asn His
        515                 520                 525
```

```
Thr Tyr Gly Gly Glu Ile Asp Val Leu Pro Thr Leu Leu Asn Leu Leu
    530                 535                 540

Gly Ile Lys Asp Ser Asp Thr Ile Gln Phe Gly Tyr Asp Leu Leu Ser
545                 550                 555                 560

Lys Asn Ala Pro Gln Ile Val Ala Gln Arg Asn Gly Asp Phe Ile Thr
                565                 570                 575

Pro Glu Tyr Ser Lys Val Gly Ser Asp Tyr Tyr Tyr Thr Lys Thr Gly
            580                 585                 590

Lys Arg Ile Lys Pro Asn Lys Lys Leu Lys Ala Glu Leu Thr Ala Ile
        595                 600                 605

Ser Asn Thr Val Thr Thr Gln Leu Ser Leu Ser Asp Arg Val Ile Asn
    610                 615                 620

Gly Asn Leu Leu Arg Phe Tyr Arg Pro Lys Trp Phe Thr Lys Val Lys
625                 630                 635                 640

Pro Lys Asp Tyr Asp Tyr Asn Lys Glu Pro Ser Leu Lys Arg Leu Phe
                645                 650                 655

Asn Asp Pro Ser Lys Thr Ser Leu Trp Tyr Gln Asn His Lys Lys Thr
            660                 665                 670

Thr Gln Lys Asp Phe Lys Thr Asp Ala Pro Glu Leu Lys Lys
        675                 680                 685


<210> SEQ ID NO 2
<211> LENGTH: 457
<212> TYPE: PRT
<213> ORGANISM: Lactobacillus acidophilus
<220> FEATURE:
<221> NAME/KEY: MISC_FEATURE
<223> OTHER INFORMATION: Amino acid sequence of SlpB protein

<400> SEQUENCE: 2

Met Lys Lys Asn Leu Arg Ile Val Ser Ala Ala Ala Ala Ala Leu Leu
1               5                   10                  15

Ala Val Ala Pro Val Ala Ala Ser Ala Val Ser Thr Val Asn Ala Ala
            20                  25                  30

Ala Val Asn Ala Ile Ala Val Gly Gly Ser Ala Thr Pro Leu Pro Asn
        35                  40                  45

Asn Ser Asp Val Gln Ile Ser Ser Ser Val Ala Gly Val Thr Thr Lys
    50                  55                  60

Asn Gly Ser Ser Tyr Thr Asn Gly Arg Ile Ser Gly Ser Ile Asn Ala
65                  70                  75                  80

Ser Tyr Asn Gly Thr Ser Tyr Ser Ala Asn Phe Ser Ser Ser Asn Ala
                85                  90                  95

Gly Val Val Val Ser Thr Pro Gly His Thr Glu Leu Ser Gly Glu Gln
            100                 105                 110

Ile Asn Gly Leu Glu Pro Gly Ser Ala Val Thr Val Thr Leu Arg Asp
        115                 120                 125

Gly Val Ser Phe Asn Phe Gly Ser Thr Asn Ala Asn Lys Thr Ile Thr
    130                 135                 140

Leu Ala Phe Pro Lys Asn Val Ser Ala Ala Gly Leu Ala Asp Ala Asn
145                 150                 155                 160

Lys Val Ser Ala Thr Ser Glu Thr Ser Val Asp Ala Gly Lys Thr Ile
                165                 170                 175

Gln Val Lys Thr Asp Lys Asn Gly Val Val Ser Phe Gly Ser Ala Gln
            180                 185                 190

Val Leu Asn Val Lys Val Val Glu Thr Ser Asp Val Arg Ala Val Ser
```

-continued

```
        195                 200                 205

Phe Tyr Asp Ile Gln Thr Gly Lys Thr Val Glu Asn Gly Thr Leu Ser
    210                 215                 220

Ile Val Ala Gly Ser Asn Ala Arg Ala Asn Val Gln Glu Ile Val Asn
225                 230                 235                 240

Ala Phe Asn Ala Lys Tyr Gln Ala Ser Gln Leu Asn Asn Ala Asn Ser
                245                 250                 255

Asn Ala Asn Val Arg Leu Thr Asp Asn Asn Ala Gln Ala Val Ala Thr
            260                 265                 270

Met Leu Arg Ala Gln Asn Ile Asp Val Asp Ala Gln Gly Tyr Phe Thr
        275                 280                 285

Ala Pro Ala Ser Leu Ser Leu Thr Phe His Ala Glu Ser Thr Gln Asn
    290                 295                 300

Asn Glu Thr Ala Gln Leu Pro Val Thr Val Ser Val Thr Asn Gly Lys
305                 310                 315                 320

Glu Val Thr Pro Ser Thr Val Asp Ser Val Ser Lys Arg Ile Met His
                325                 330                 335

Asn Ala Tyr Tyr Tyr Asp Lys Asp Ala Lys Arg Val Gly Thr Asp Ser
            340                 345                 350

Val Lys Arg Tyr Asn Ser Val Ser Val Leu Pro Asn Thr Thr Thr Ile
        355                 360                 365

Asn Gly Lys Ala Tyr Tyr Gln Val Val Glu Asn Gly Lys Ala Val Asp
    370                 375                 380

Lys Tyr Ile Asn Ala Ala Asn Ile Asp Gly Thr Lys Arg Thr Leu Lys
385                 390                 395                 400

His Asn Ala Tyr Val Tyr Ala Ser Ser Lys Lys Arg Ala Asn Lys Val
                405                 410                 415

Val Leu Lys Lys Gly Glu Val Val Thr Thr Tyr Gly Ala Ser Tyr Thr
            420                 425                 430

Phe Lys Asn Gly Gln Lys Tyr Tyr Lys Ile Gly Asp Asn Thr Asp Lys
        435                 440                 445

Thr Tyr Val Lys Val Ala Asn Phe Arg
    450                 455


<210> SEQ ID NO 3
<211> LENGTH: 499
<212> TYPE: PRT
<213> ORGANISM: Lactobacillus acidophilus
<220> FEATURE:
<221> NAME/KEY: MISC_FEATURE
<223> OTHER INFORMATION: Amino acid sequence of SlpX protein

<400> SEQUENCE: 3

Met Lys Lys Asn Arg Lys Met Leu Gly Leu Ala Ala Ala Thr Leu Leu
1               5                   10                  15

Ala Val Ala Pro Val Ala Thr Ser Val Val Pro Val Gln Ala Asp Thr
            20                  25                  30

Ala Val Asn Val Gly Ser Ala Ala Gly Thr Gly Ala Asn Thr Thr Asn
        35                  40                  45

Thr Thr Thr Gln Ala Pro Gln Asn Lys Pro Tyr Phe Thr Tyr Asn Asn
    50                  55                  60

Glu Ile Ile Gly Glu Ala Thr Gln Ser Asn Pro Leu Gly Asn Val Val
65                  70                  75                  80

Arg Thr Thr Ile Ser Phe Lys Ser Asp Asp Lys Val Ser Asp Leu Ile
                85                  90                  95
```

-continued

```
Ser Thr Ile Ser Lys Ala Val Gln Phe His Lys Asn Asn Ser Ala Ser
            100                 105                 110

Gly Glu Asn Val Thr Ile Asn Glu Asn Asp Phe Ile Asn Gln Leu Lys
        115                 120                 125

Ala Asn Gly Val Thr Val Lys Thr Val Gln Pro Ser Asn Lys Asn Glu
    130                 135                 140

Lys Ala Tyr Glu Ala Ile Asp Lys Val Pro Ser Thr Ser Phe Asn Ile
145                 150                 155                 160

Thr Leu Ser Ala Thr Gly Asp Asn Asn Gln Thr Ala Thr Ile Gln Ile
                165                 170                 175

Pro Met Val Pro Gln Gly Ala Ser Thr Pro Thr Asp Thr Thr Gln Asn
            180                 185                 190

Pro Gln Ile Asn Trp Thr Lys Gly Gly Gln Ala Gln Ser Ser Ser Leu
        195                 200                 205

Asn Gly Gln Val Phe Gln Val Ala Val Gly Ser Asn Phe Asn Pro Leu
    210                 215                 220

Asn Phe Thr Asn Ser Asn Gly Glu Asn Ile Ile Val Ser Ala Gln Gln
225                 230                 235                 240

Ser Lys Asn Asn Thr Thr Phe Ala Ser Ile Glu Ala Thr Ser Asn Pro
                245                 250                 255

Val Asn Thr Ser Glu Ala Gly Arg Tyr Tyr Asn Val Thr Leu Thr Ala
            260                 265                 270

Thr Gly Asn Thr Gly Lys Lys Thr Thr Ala Thr Tyr Thr Val Leu Ile
        275                 280                 285

Thr Ser Ser Gln Lys Gln Thr Leu Tyr Gly Asn Gly Glu Ser Thr Ile
    290                 295                 300

Ser Thr Tyr Ser Ile Tyr Gly Asn Asn Val Leu Ser Asn Ser Thr Thr
305                 310                 315                 320

Phe Lys Asp Gly Asp Gln Val Tyr Val Ser Asp Gln Thr Lys Thr Val
                325                 330                 335

Gly Gly Val Ser Tyr Ser Gln Val Ser Pro Lys Ser Lys Asn Asp Ala
            340                 345                 350

Asn Ser Ser Asn Ile Trp Val Lys Thr Ser Ala Leu Val Lys Pro Ala
        355                 360                 365

Gly Asp Thr Asn Val Lys Thr Tyr Pro Val Met Val Asp Ser Arg Ala
    370                 375                 380

Tyr Asp Lys Asn Gly Asn Tyr Leu Gly His Met Tyr Tyr Ala Tyr Asp
385                 390                 395                 400

Asn Ile Asp Ile Val Pro Thr Val Val Thr Ile Asn Gly Lys Thr Tyr
                405                 410                 415

Tyr Lys Val Ala Asn Lys Asp Glu Tyr Val Arg Val Thr Asn Ile Thr
            420                 425                 430

Gly Asn Gln Arg Thr Leu Lys His Asn Ala Tyr Ile Tyr Trp Ser Ser
        435                 440                 445

Tyr Arg Arg Thr Pro Gly Thr Gly Lys Met Tyr Arg Gly Gln Thr Val
    450                 455                 460

Thr Thr Tyr Gly Pro Gln Met Lys Phe Lys Asn Gly Lys Lys Tyr Tyr
465                 470                 475                 480

Arg Ile Glu Gly Cys Arg Asn Asn Asn Lys Arg Tyr Ile Lys Ala Val
                485                 490                 495

Asn Phe Tyr
```

<210> SEQ ID NO 4

-continued

<211> LENGTH: 444
<212> TYPE: PRT
<213> ORGANISM: Lactobacillus acidophilus
<220> FEATURE:
<221> NAME/KEY: MISC_FEATURE
<223> OTHER INFORMATION: Amino acid sequence of SlpA protein

<400> SEQUENCE: 4

```
Met Lys Lys Asn Leu Arg Ile Val Ser Ala Ala Ala Ala Ala Leu Leu
1               5                   10                  15

Ala Val Ala Pro Val Ala Ala Ser Ala Val Ser Thr Val Ser Ala Ala
            20                  25                  30

Thr Thr Ile Asn Ala Ser Ser Ser Ala Ile Asn Thr Asn Thr Asn Ala
        35                  40                  45

Lys Tyr Asp Val Asp Val Thr Pro Ser Val Ser Ala Val Ala Ala Asn
    50                  55                  60

Thr Ala Asn Asn Thr Pro Ala Ile Ala Gly Asn Leu Thr Gly Thr Ile
65                  70                  75                  80

Ser Ala Ser Tyr Asn Gly Lys Thr Tyr Thr Ala Asn Leu Lys Ala Asp
                85                  90                  95

Thr Glu Asn Ala Thr Ile Thr Ala Ala Gly Ser Thr Thr Ala Val Lys
            100                 105                 110

Pro Ala Glu Leu Ala Ala Gly Val Ala Tyr Thr Val Thr Val Asn Asp
        115                 120                 125

Val Ser Phe Asn Phe Gly Ser Glu Asn Ala Gly Lys Thr Val Thr Leu
    130                 135                 140

Gly Ser Ala Asn Ser Asn Val Lys Phe Thr Gly Thr Asn Ser Asp Asn
145                 150                 155                 160

Gln Thr Glu Thr Asn Val Ser Thr Leu Lys Val Lys Leu Asp Gln Asn
                165                 170                 175

Gly Val Ala Ser Leu Thr Asn Val Ser Ile Ala Asn Val Tyr Ala Ile
            180                 185                 190

Asn Thr Thr Asp Asn Ser Asn Val Asn Phe Tyr Asp Val Thr Ser Gly
        195                 200                 205

Ala Thr Val Thr Asn Gly Ala Val Ser Val Asn Ala Asp Asn Gln Gly
    210                 215                 220

Gln Val Asn Val Ala Asn Val Val Ala Ala Ile Asn Ser Lys Tyr Phe
225                 230                 235                 240

Ala Ala Gln Tyr Ala Asp Lys Lys Leu Asn Thr Arg Thr Ala Asn Thr
                245                 250                 255

Glu Asp Ala Ile Lys Ala Ala Leu Lys Asp Gln Lys Ile Asp Val Asn
            260                 265                 270

Ser Val Gly Tyr Phe Lys Ala Pro His Thr Phe Thr Val Asn Val Lys
        275                 280                 285

Ala Thr Ser Asn Thr Asn Gly Lys Ser Ala Thr Leu Pro Val Val Val
    290                 295                 300

Thr Val Pro Asn Val Ala Glu Pro Thr Val Ala Ser Val Ser Lys Arg
305                 310                 315                 320

Ile Met His Asn Ala Tyr Tyr Tyr Asp Lys Asp Ala Lys Arg Val Gly
                325                 330                 335

Thr Asp Ser Val Lys Arg Tyr Asn Ser Val Ser Val Leu Pro Asn Thr
            340                 345                 350

Thr Thr Ile Asn Gly Lys Thr Tyr Tyr Gln Val Val Glu Asn Gly Lys
        355                 360                 365

Ala Val Asp Lys Tyr Ile Asn Ala Ala Asn Ile Asp Gly Thr Lys Arg
```

```
    370                 375                 380

Thr Leu Lys His Asn Ala Tyr Val Tyr Ala Ser Ser Lys Lys Arg Ala
385                 390                 395                 400

Asn Lys Val Val Leu Lys Lys Gly Glu Val Val Thr Thr Tyr Gly Ala
                405                 410                 415

Ser Tyr Thr Phe Lys Asn Gly Gln Lys Tyr Tyr Lys Ile Gly Asp Asn
            420                 425                 430

Thr Asp Lys Thr Tyr Val Lys Val Ala Asn Phe Arg
        435                 440


<210> SEQ ID NO 5
<211> LENGTH: 20
<212> TYPE: DNA
<213> ORGANISM: Artificial Sequence
<220> FEATURE:
<223> OTHER INFORMATION: 111b Forward primer sequence

<400> SEQUENCE: 5

aaggagaacc aagcaacgac                                                 20


<210> SEQ ID NO 6
<211> LENGTH: 20
<212> TYPE: DNA
<213> ORGANISM: Artificial Sequence
<220> FEATURE:
<223> OTHER INFORMATION: 111b Reverse primer sequence

<400> SEQUENCE: 6

gagattgagc tgtctgctca                                                 20


<210> SEQ ID NO 7
<211> LENGTH: 20
<212> TYPE: DNA
<213> ORGANISM: Artificial Sequence
<220> FEATURE:
<223> OTHER INFORMATION: Ocln Forward primer sequence

<400> SEQUENCE: 7

gctgtgatgt gtgtgagctg                                                 20


<210> SEQ ID NO 8
<211> LENGTH: 20
<212> TYPE: DNA
<213> ORGANISM: Artificial Sequence
<220> FEATURE:
<223> OTHER INFORMATION: Ocln Reverse primer sequence

<400> SEQUENCE: 8

gacggtctac ctggaggaac                                                 20


<210> SEQ ID NO 9
<211> LENGTH: 23
<212> TYPE: DNA
<213> ORGANISM: Artificial Sequence
<220> FEATURE:
<223> OTHER INFORMATION: Cd209a Forward primer sequence

<400> SEQUENCE: 9

tctggattca gtagcttcac agg                                             23


<210> SEQ ID NO 10
<211> LENGTH: 23
<212> TYPE: DNA
<213> ORGANISM: Artificial Sequence
```

```
<220> FEATURE:
<223> OTHER INFORMATION: Cd209a Reverse primer sequence

<400> SEQUENCE: 10

gggtcagttc ttggtagaca ttc                                            23


<210> SEQ ID NO 11
<211> LENGTH: 21
<212> TYPE: DNA
<213> ORGANISM: Artificial Sequence
<220> FEATURE:
<223> OTHER INFORMATION: Cd209b Forward primer sequence

<400> SEQUENCE: 11

ttgatggtca gcggcagcag g                                              21


<210> SEQ ID NO 12
<211> LENGTH: 21
<212> TYPE: DNA
<213> ORGANISM: Artificial Sequence
<220> FEATURE:
<223> OTHER INFORMATION: Cd209b Reverse primer sequence

<400> SEQUENCE: 12

tcagcaggag cccagccaag a                                              21


<210> SEQ ID NO 13
<211> LENGTH: 22
<212> TYPE: DNA
<213> ORGANISM: Artificial Sequence
<220> FEATURE:
<223> OTHER INFORMATION: Cd209c Forward primer sequence

<400> SEQUENCE: 13

ctggaatgac tctgtcaatg cc                                             22


<210> SEQ ID NO 14
<211> LENGTH: 21
<212> TYPE: DNA
<213> ORGANISM: Artificial Sequence
<220> FEATURE:
<223> OTHER INFORMATION: Cd209c Reverse primer sequence

<400> SEQUENCE: 14

gccatctgcc ttcatgcttc a                                              21


<210> SEQ ID NO 15
<211> LENGTH: 20
<212> TYPE: DNA
<213> ORGANISM: Artificial Sequence
<220> FEATURE:
<223> OTHER INFORMATION: Cd209d Forward primer sequence

<400> SEQUENCE: 15

gggcccaact ggtcatcata                                                20


<210> SEQ ID NO 16
<211> LENGTH: 20
<212> TYPE: DNA
<213> ORGANISM: Artificial Sequence
<220> FEATURE:
<223> OTHER INFORMATION: Cd209d Reverse primer sequence

<400> SEQUENCE: 16

agcgtgtaaa gctgggtgac                                                20
```

<210> SEQ ID NO 17
<211> LENGTH: 19
<212> TYPE: DNA
<213> ORGANISM: Artificial Sequence
<220> FEATURE:
<223> OTHER INFORMATION: Cd209e Forward primer sequence

<400> SEQUENCE: 17
ccacattccc ctggtgttg 19

<210> SEQ ID NO 18
<211> LENGTH: 21
<212> TYPE: DNA
<213> ORGANISM: Artificial Sequence
<220> FEATURE:
<223> OTHER INFORMATION: Cd209e Reverse primer sequence

<400> SEQUENCE: 18
cagaggcgac agagtctatc a 21

<210> SEQ ID NO 19
<211> LENGTH: 21
<212> TYPE: DNA
<213> ORGANISM: Artificial Sequence
<220> FEATURE:
<223> OTHER INFORMATION: Cd209f Forward primer sequence

<400> SEQUENCE: 19
ctctttgggc ctctttttgc t 21

<210> SEQ ID NO 20
<211> LENGTH: 21
<212> TYPE: DNA
<213> ORGANISM: Artificial Sequence
<220> FEATURE:
<223> OTHER INFORMATION: Cd209f Reverse primer sequence

<400> SEQUENCE: 20
agtatgcacg aatcctggag a 21

<210> SEQ ID NO 21
<211> LENGTH: 20
<212> TYPE: DNA
<213> ORGANISM: Artificial Sequence
<220> FEATURE:
<223> OTHER INFORMATION: Cd209g Forward primer sequence

<400> SEQUENCE: 21
ggcctcagcg atcacagaag 20

<210> SEQ ID NO 22
<211> LENGTH: 22
<212> TYPE: DNA
<213> ORGANISM: Artificial Sequence
<220> FEATURE:
<223> OTHER INFORMATION: Cd209g Reverse primer sequence

<400> SEQUENCE: 22
acaacggctg tcattccatt ta 22

<210> SEQ ID NO 23
<211> LENGTH: 20
<212> TYPE: DNA
<213> ORGANISM: Artificial Sequence
<220> FEATURE:
<223> OTHER INFORMATION: Muc2 Forward primer sequence

<400> SEQUENCE: 23
gtgtgggacc tgacaatgtg 20

<210> SEQ ID NO 24
<211> LENGTH: 20
<212> TYPE: DNA
<213> ORGANISM: Artificial Sequence
<220> FEATURE:
<223> OTHER INFORMATION: Muc2 Reverse primer sequence

<400> SEQUENCE: 24
acaacgaggt aggtgccatc 20

<210> SEQ ID NO 25
<211> LENGTH: 21
<212> TYPE: DNA
<213> ORGANISM: Artificial Sequence
<220> FEATURE:
<223> OTHER INFORMATION: Muc3 Forward primer sequence

<400> SEQUENCE: 25
gccgtgaatt gtatgaacgg a 21

<210> SEQ ID NO 26
<211> LENGTH: 21
<212> TYPE: DNA
<213> ORGANISM: Artificial Sequence
<220> FEATURE:
<223> OTHER INFORMATION: Muc3 Reverse primer sequence

<400> SEQUENCE: 26
cgcagttgac cacgttgact a 21

<210> SEQ ID NO 27
<211> LENGTH: 20
<212> TYPE: DNA
<213> ORGANISM: Artificial Sequence
<220> FEATURE:
<223> OTHER INFORMATION: Tjp1 Forward primer sequence

<400> SEQUENCE: 27
aggacaccaa agcatgtgag 20

<210> SEQ ID NO 28
<211> LENGTH: 19
<212> TYPE: DNA
<213> ORGANISM: Artificial Sequence
<220> FEATURE:
<223> OTHER INFORMATION: Tjp1 Reverse primer sequence

<400> SEQUENCE: 28
ggcattcctg ctggttaca 19

<210> SEQ ID NO 29
<211> LENGTH: 20
<212> TYPE: DNA
<213> ORGANISM: Artificial Sequence
<220> FEATURE:
<223> OTHER INFORMATION: Tjp2 Forward primer sequence

<400> SEQUENCE: 29
atgggagcag tacaccgtga 20

<210> SEQ ID NO 30

<211> LENGTH: 22
<212> TYPE: DNA
<213> ORGANISM: Artificial Sequence
<220> FEATURE:
<223> OTHER INFORMATION: Tjp2 Reverse primer sequence

<400> SEQUENCE: 30
tgaccaccct gtcattttct tg 22

<210> SEQ ID NO 31
<211> LENGTH: 20
<212> TYPE: DNA
<213> ORGANISM: Artificial Sequence
<220> FEATURE:
<223> OTHER INFORMATION: Tjp3 Forward primer sequence

<400> SEQUENCE: 31
tcggcatagc tgtctctgga 20

<210> SEQ ID NO 32
<211> LENGTH: 20
<212> TYPE: DNA
<213> ORGANISM: Artificial Sequence
<220> FEATURE:
<223> OTHER INFORMATION: Tjp3 Reverse primer sequence

<400> SEQUENCE: 32
gttggctgtt ttggtgcagg 20

<210> SEQ ID NO 33
<211> LENGTH: 20
<212> TYPE: DNA
<213> ORGANISM: Artificial Sequence
<220> FEATURE:
<223> OTHER INFORMATION: Cldn1 Forward primer sequence

<400> SEQUENCE: 33
tccttgttcg gctatgtgtc 20

<210> SEQ ID NO 34
<211> LENGTH: 20
<212> TYPE: DNA
<213> ORGANISM: Artificial Sequence
<220> FEATURE:
<223> OTHER INFORMATION: Cldn1 Reverse primer sequence

<400> SEQUENCE: 34
ggcatgcacc taagaatcag 20

<210> SEQ ID NO 35
<211> LENGTH: 19
<212> TYPE: DNA
<213> ORGANISM: Artificial Sequence
<220> FEATURE:
<223> OTHER INFORMATION: Cldn2 Forward primer sequence

<400> SEQUENCE: 35
ggctgttagg cacatccat 19

<210> SEQ ID NO 36
<211> LENGTH: 20
<212> TYPE: DNA
<213> ORGANISM: Artificial Sequence
<220> FEATURE:
<223> OTHER INFORMATION: Cldn2 Reverse primer sequence

<400> SEQUENCE: 36
tggcaccaac ataggaactc 20

<210> SEQ ID NO 37
<211> LENGTH: 20
<212> TYPE: DNA
<213> ORGANISM: Artificial Sequence
<220> FEATURE:
<223> OTHER INFORMATION: Cldn3 Forward primer sequence

<400> SEQUENCE: 37
tggcaccaac ataggaactc 20

<210> SEQ ID NO 38
<211> LENGTH: 19
<212> TYPE: DNA
<213> ORGANISM: Artificial Sequence
<220> FEATURE:
<223> OTHER INFORMATION: Cldn3 Reverse primer sequence

<400> SEQUENCE: 38
ctggcaagta gctgcagtg 19

<210> SEQ ID NO 39
<211> LENGTH: 22
<212> TYPE: DNA
<213> ORGANISM: Artificial Sequence
<220> FEATURE:
<223> OTHER INFORMATION: Cldn5 Forward primer sequence

<400> SEQUENCE: 39
gcaaggtgta tgaatctgtg ct 22

<210> SEQ ID NO 40
<211> LENGTH: 22
<212> TYPE: DNA
<213> ORGANISM: Artificial Sequence
<220> FEATURE:
<223> OTHER INFORMATION: Cldn5 Reverse primer sequence

<400> SEQUENCE: 40
gtcaaggtaa caaagagtgc ca 22

<210> SEQ ID NO 41
<211> LENGTH: 20
<212> TYPE: DNA
<213> ORGANISM: Artificial Sequence
<220> FEATURE:
<223> OTHER INFORMATION: Cldn8 Forward primer sequence

<400> SEQUENCE: 41
gccggaatca tcttcttcat 20

<210> SEQ ID NO 42
<211> LENGTH: 20
<212> TYPE: DNA
<213> ORGANISM: Artificial Sequence
<220> FEATURE:
<223> OTHER INFORMATION: Cldn8 Reverse primer sequence

<400> SEQUENCE: 42
catccaccag tgggttgtag 20

<210> SEQ ID NO 43
<211> LENGTH: 19
<212> TYPE: DNA

<213> ORGANISM: Artificial Sequence
<220> FEATURE:
<223> OTHER INFORMATION: Hsp25 Forward primer sequence

<400> SEQUENCE: 43
ggttgcccga tgagtggtc 19

<210> SEQ ID NO 44
<211> LENGTH: 19
<212> TYPE: DNA
<213> ORGANISM: Artificial Sequence
<220> FEATURE:
<223> OTHER INFORMATION: Hsp25 Reverse primer sequence

<400> SEQUENCE: 44
ctgagctgtc ggttgagcg 19

<210> SEQ ID NO 45
<211> LENGTH: 19
<212> TYPE: DNA
<213> ORGANISM: Artificial Sequence
<220> FEATURE:
<223> OTHER INFORMATION: Hsp72 Forward primer sequence

<400> SEQUENCE: 45
ctccctcttg cgttgcctc 19

<210> SEQ ID NO 46
<211> LENGTH: 21
<212> TYPE: DNA
<213> ORGANISM: Artificial Sequence
<220> FEATURE:
<223> OTHER INFORMATION: Hsp72 Forward primer sequence

<400> SEQUENCE: 46
acccgcagta atagccatct g 21

<210> SEQ ID NO 47
<211> LENGTH: 288
<212> TYPE: PRT
<213> ORGANISM: Artificial Sequence
<220> FEATURE:
<223> OTHER INFORMATION: SlpA protein sequence

<400> SEQUENCE: 47

```
Ala Ala Thr Thr Ile Asn Ala Ser Ser Ser Ala Ile Asn Thr Asn Thr
1               5                   10                  15

Asn Ala Lys Tyr Asp Val Asp Val Thr Pro Ser Val Ser Ala Val Ala
            20                  25                  30

Ala Val Ala Ala Asn Thr Ala Asn Asn Thr Pro Ala Ile Ala Gly Asn
        35                  40                  45

Leu Thr Gly Thr Ile Ser Ala Ser Tyr Asn Gly Lys Thr Tyr Thr Ala
    50                  55                  60

Asn Leu Lys Ala Asp Thr Glu Asn Ala Thr Ile Thr Ala Ala Gly Ser
65                  70                  75                  80

Thr Thr Ala Val Lys Pro Ala Glu Leu Ala Ala Gly Val Ala Tyr Thr
                85                  90                  95

Val Thr Val Asn Asp Val Ser Phe Asn Phe Gly Ser Glu Asn Ala Gly
            100                 105                 110

Lys Thr Val Thr Leu Gly Ser Ala Asn Ser Asn Val Lys Phe Thr Gly
        115                 120                 125

Thr Asn Ser Asp Asn Gln Thr Glu Thr Asn Val Ser Thr Leu Lys Val
```

```
    130                 135                 140

Lys Leu Asp Gln Asn Gly Val Ala Ser Leu Thr Asn Val Ser Ile Ala
145                 150                 155                 160

Asn Val Tyr Ala Ile Asn Thr Thr Asp Asn Ser Asn Val Asn Phe Tyr
                165                 170                 175

Asp Val Thr Ser Gly Ala Thr Val Thr Asn Gly Ala Val Ser Val Asn
            180                 185                 190

Ala Asp Asn Gln Gly Gln Val Asn Val Ala Asn Val Val Ala Ala Ile
        195                 200                 205

Asn Ser Lys Tyr Phe Ala Ala Gln Tyr Ala Asp Lys Lys Leu Asn Thr
    210                 215                 220

Arg Thr Ala Asn Thr Glu Asp Ala Ile Lys Ala Ala Leu Lys Asp Gln
225                 230                 235                 240

Lys Ile Asp Val Asn Ser Val Gly Tyr Phe Lys Ala Pro His Thr Phe
                245                 250                 255

Thr Val Asn Val Lys Ala Thr Ser Asn Thr Asn Gly Lys Ser Ala Thr
            260                 265                 270

Leu Pro Val Val Val Thr Val Pro Asn Val Ala Glu Pro Thr Val Ala
        275                 280                 285


<210> SEQ ID NO 48
<211> LENGTH: 444
<212> TYPE: PRT
<213> ORGANISM: Artificial Sequence
<220> FEATURE:
<223> OTHER INFORMATION: SlpA protein sequence

<400> SEQUENCE: 48

Met Lys Lys Asn Leu Arg Ile Val Ser Ala Ala Ala Ala Ala Leu Leu
1               5                   10                  15

Ala Val Ala Pro Val Ala Ala Ser Ala Val Ser Thr Val Ser Ala Ala
            20                  25                  30

Thr Thr Ile Asn Ala Ser Ser Ser Ala Ile Asn Thr Asn Thr Asn Ala
        35                  40                  45

Lys Tyr Asp Val Asp Val Thr Pro Ser Val Ser Ala Val Ala Ala Asn
    50                  55                  60

Thr Ala Asn Asn Thr Pro Ala Ile Ala Gly Asn Leu Thr Gly Thr Ile
65                  70                  75                  80

Ser Ala Ser Tyr Asn Gly Lys Thr Tyr Thr Ala Asn Leu Lys Ala Asp
                85                  90                  95

Thr Glu Asn Ala Thr Ile Thr Ala Ala Gly Ser Thr Thr Ala Val Lys
            100                 105                 110

Pro Ala Glu Leu Ala Ala Gly Val Ala Tyr Thr Val Thr Val Asn Asp
        115                 120                 125

Val Ser Phe Asn Phe Gly Ser Glu Asn Ala Gly Lys Thr Val Thr Leu
    130                 135                 140

Gly Ser Ala Asn Ser Asn Val Lys Phe Thr Gly Thr Asn Ser Asp Asn
145                 150                 155                 160

Gln Thr Glu Thr Asn Val Ser Thr Leu Lys Val Lys Leu Asp Gln Asn
                165                 170                 175

Gly Val Ala Ser Leu Thr Asn Val Ser Ile Ala Asn Val Tyr Ala Ile
            180                 185                 190

Asn Thr Thr Asp Asn Ser Asn Val Asn Phe Tyr Asp Val Thr Ser Gly
        195                 200                 205

Ala Thr Val Thr Asn Gly Ala Val Ser Val Asn Ala Asp Asn Gln Gly
```

```
    210                 215                 220

Gln Val Asn Val Ala Asn Val Val Ala Ala Ile Asn Ser Lys Tyr Phe
225                 230                 235                 240

Ala Ala Gln Tyr Ala Asp Lys Lys Leu Asn Thr Arg Thr Ala Asn Thr
                245                 250                 255

Glu Asp Ala Ile Lys Ala Ala Leu Lys Asp Gln Lys Ile Asp Val Asn
            260                 265                 270

Ser Val Gly Tyr Phe Lys Ala Pro His Thr Phe Thr Val Asn Val Lys
        275                 280                 285

Ala Thr Ser Asn Thr Asn Gly Lys Ser Ala Thr Leu Pro Val Val Val
    290                 295                 300

Thr Val Pro Asn Val Ala Glu Pro Thr Val Ala Ser Val Ser Lys Arg
305                 310                 315                 320

Ile Met His Asn Ala Tyr Tyr Tyr Asp Lys Asp Ala Lys Arg Val Gly
                325                 330                 335

Thr Asp Ser Val Lys Arg Tyr Asn Ser Val Ser Val Leu Pro Asn Thr
            340                 345                 350

Thr Thr Ile Asn Gly Lys Thr Tyr Tyr Gln Val Val Glu Asn Gly Lys
        355                 360                 365

Ala Val Asp Lys Tyr Ile Asn Ala Ala Asn Ile Asp Gly Thr Lys Arg
    370                 375                 380

Thr Leu Lys His Asn Ala Tyr Val Tyr Ala Ser Ser Lys Lys Arg Ala
385                 390                 395                 400

Asn Lys Val Val Leu Lys Lys Gly Glu Val Val Thr Thr Tyr Gly Ala
                405                 410                 415

Ser Tyr Thr Phe Lys Asn Gly Gln Lys Tyr Tyr Lys Ile Gly Asp Asn
            420                 425                 430

Thr Asp Lys Thr Tyr Val Lys Val Ala Asn Phe Arg
        435                 440


<210> SEQ ID NO 49
<211> LENGTH: 469
<212> TYPE: PRT
<213> ORGANISM: Artificial Sequence
<220> FEATURE:
<223> OTHER INFORMATION: SlpA protein sequence

<400> SEQUENCE: 49

Met Phe Gly Gly Arg Lys Ile Met Gln Ser Ser Leu Lys Lys Ser Leu
1               5                   10                  15

Tyr Leu Gly Leu Ala Ala Leu Ser Phe Ala Gly Val Ala Ala Val Ser
            20                  25                  30

Thr Thr Ala Ser Ala Lys Ser Tyr Ala Thr Ala Gly Ala Tyr Thr Thr
        35                  40                  45

Leu Lys Thr Asp Ala Thr Lys Arg Asn Val Glu Ala Thr Gly Thr Asn
    50                  55                  60

Ala Leu Tyr Thr Lys Pro Gly Thr Val Lys Gly Ala Lys Val Val Ala
65                  70                  75                  80

Ser Lys Ala Thr Met Ala Lys Leu Ala Ser Ser Lys Lys Ser Ala Asp
                85                  90                  95

Tyr Phe Arg Ala Tyr Gly Val Lys Thr Thr Asn Arg Gly Ser Val Tyr
            100                 105                 110

Tyr Arg Val Val Ser Met Asp Gly Lys Tyr Arg Gly Tyr Val Tyr Gly
        115                 120                 125

Gly Lys Ser Asp Thr Ala Phe Ala Gly Gly Ile Lys Ser Ala Asp Thr
```

-continued

```
    130                 135                 140

Thr Thr Thr Ala Thr Thr Pro Thr Arg Thr Thr Gly Tyr Tyr Leu Lys
145                 150                 155                 160

Asp Val Ser Lys Asn Thr Leu Trp Thr Ala Pro Lys Asn Thr Gln Tyr
                165                 170                 175

Lys Ala Ser Lys Val Ser Leu Tyr Gly Val Lys Ser Thr Asp Thr Phe
            180                 185                 190

Lys Val Asp Ser Ala Ala Thr Lys Thr Arg Glu Gly Ser Leu Tyr Tyr
        195                 200                 205

His Val Thr Asp Thr Gln Asn Thr Ser Val Ser Gly Trp Ile Tyr Ala
    210                 215                 220

Gly Lys Gly Tyr Val Ala Gly Ala Thr Thr Gln Asp Leu Gly Gly Leu
225                 230                 235                 240

Ser Leu Thr Met Ser Asp Ala Ala Ala Thr Ser Asp Asn Ser Val Lys
                245                 250                 255

Val Val Tyr Arg Ala Ser Gly Ser Gln Val Gly Thr Ala Thr Trp Val
            260                 265                 270

Thr Ala Ala Ala Gly Thr Lys Ala Gly Ala Thr Val Gly Thr Thr Ala
        275                 280                 285

Val Asn Ala Ala Gly Val Lys Leu Ala Asp Phe Val Thr Asn Ser Leu
    290                 295                 300

Pro Ser Gly Tyr Thr Thr Thr Gly Thr Val Asp Thr Ala Ser Ala Thr
305                 310                 315                 320

Tyr Gly Asn Thr Val Tyr Val Asp Val Thr Ala Ala Ala Thr Ser Lys
                325                 330                 335

Val Gln Leu Val Ala Asp Asn Val Asp Asn Thr Ala Ser Thr Thr Asp
            340                 345                 350

Asn Ala Val Ala Gly Val Leu Ala Asn Gly Ala Lys Leu Ser Ser Ser
        355                 360                 365

Asp Leu Ser Ala Thr Leu Lys Glu Ala Gly Ile Lys Ala Leu Thr Gly
    370                 375                 380

Thr Lys Gly Glu Ala Ile Gly Ala Thr Asn Leu Ala Thr Ile Ser Gly
385                 390                 395                 400

Ala Phe Asp Thr Ala Glu Ile Asn Gly Ser Lys Thr Tyr Tyr Ala Ala
                405                 410                 415

Asn Gly Asp Ala Tyr His Tyr Val Phe Thr Tyr Glu Pro Ala Asn Phe
            420                 425                 430

Ala Asn Asp Asn Arg Leu Ala Thr Tyr Gly Asp Thr Leu Thr Ala Ser
        435                 440                 445

Phe Lys Ala Val Leu Thr Lys Gly Ala Pro Ser Ala Ser Ser Ser Asn
    450                 455                 460

Ser Ser Trp Ile Ala
465
```

<210> SEQ ID NO 50
<211> LENGTH: 451
<212> TYPE: PRT
<213> ORGANISM: Artificial Sequence
<220> FEATURE:
<223> OTHER INFORMATION: SlpA protein sequence

<400> SEQUENCE: 50

```
Met Lys Lys Asn Leu Arg Ile Val Ser Ala Ala Ala Ala Ala Leu Leu
1               5                   10                  15

Ala Val Ala Pro Val Ala Ala Ser Ala Val Ser Val Asn Ala Ala Asp
```

-continued

```
            20                  25                  30

Asn Thr Val Ala Thr Thr Thr Asn Thr Ala Asn Thr Val Ile Asn Ala
        35                  40                  45

Asp Gly Thr Ala Ile Asn Thr Pro Ala Asp Ala Lys Tyr Asp Val Asp
    50                  55                  60

Val Thr Pro Asn Leu Thr Ala Thr Ala Ala Ser Thr Val Asn Gly Gln
65                  70                  75                  80

Thr Ile Asn Gly Ser Ile Thr Gly Asn Ile Thr Ala Ser Tyr Asn Gly
                85                  90                  95

Gln Ser Tyr Thr Gly Thr Leu Asp Thr Lys Asn Gly Lys Val Ser Val
            100                 105                 110

Ala Asp Ser Lys Gly Thr Ala Val Thr Asp Phe Ser Lys Leu Thr Asn
        115                 120                 125

Gly Ser Tyr Thr Val Thr Val Ser Gly Val Ser Phe Asn Phe Gly Thr
    130                 135                 140

Ala Asn Ala Asn Lys Thr Ile Thr Leu Gly Ser Lys Asn Ser Asn Val
145                 150                 155                 160

Lys Phe Ala Gly Ala Asp Gly Lys Phe Ala Asp Thr Val Lys Val Glu
                165                 170                 175

Leu Gly Gln Asn Gly Thr Leu Thr Thr Pro Ile Ser Val Gln Val Ser
            180                 185                 190

Asn Val Asn Ala Leu Asp Leu Ser Asn Ala Asn Gly Val Asn Phe Tyr
        195                 200                 205

Asn Ala Ser Asn Gly Ser Gln Val Thr Lys Gly Ser Val Asn Val Thr
    210                 215                 220

Ala Gly Leu Ile Gly Arg Leu Asn Val Ser Thr Val Ala Ser Glu Ile
225                 230                 235                 240

Leu Lys Asn Cys Ala Ala Tyr Gln Val Ser Asn Gly Lys Pro Val Ser
                245                 250                 255

Gln Leu Pro Asp Gln Lys Ala Val Val Ala Asp Val Asn Ala Ala Leu
            260                 265                 270

Lys Ala Ala Asn Ile Pro Val Asp Asn Ala Gly Trp Phe Thr Ala Pro
        275                 280                 285

Ile Ser Leu Ser Val Asn Val Lys Ala Ser Ser Ser Ile Asn Gly Val
    290                 295                 300

Gly Cys Tyr Phe Thr Cys Thr Val Asn Val Ala Asn Gly Lys Asp Met
305                 310                 315                 320

Thr Val Pro Ser Gln Ser Lys Thr Ile Met His Asn Ala Tyr Tyr Tyr
                325                 330                 335

Asp Lys Asp Ala Lys Arg Val Gly Thr Asp Lys Leu Thr Arg Tyr Asn
            340                 345                 350

Ser Val Thr Val Ala Met Asn Thr Thr Thr Ile Asn Gly Lys Ala Tyr
        355                 360                 365

Tyr Glu Val Ile Glu Asn Gly Lys Ala Thr Gly Lys Phe Ile Asn Ala
    370                 375                 380

Asp Asn Ile Asp Gly Thr Lys Arg Thr Leu Lys His Asn Ala Tyr Val
385                 390                 395                 400

Tyr Lys Thr Ser Lys Lys Arg Ala Asn Lys Val Thr Leu Lys Lys Gly
                405                 410                 415

Thr Glu Val Thr Thr Tyr Gly Gly Thr Tyr Thr Phe Lys Asn Gly Lys
            420                 425                 430

Gln Tyr Tyr Lys Ile Gly Asn Asn Thr Asp Lys Thr Tyr Val Lys Ala
        435                 440                 445
```

Ser Asn Phe
450

<210> SEQ ID NO 51
<211> LENGTH: 439
<212> TYPE: PRT
<213> ORGANISM: Artificial Sequence
<220> FEATURE:
<223> OTHER INFORMATION: SlpA protein sequence

<400> SEQUENCE: 51

Met Lys Lys Asn Leu Arg Ile Val Ser Ala Ala Ala Ala Ala Leu Leu
1 5 10 15

Ala Val Ala Pro Val Ala Ala Ala Gly Val Ser Ser Val Thr Ala Ser
20 25 30

Ser Ile Glu Phe Val Gly Ser Ser Asn Ser Ser Leu Leu Pro Glu Val
35 40 45

Asn Asp His Thr Val Asn Phe Gly Ile Asn Phe Asn Ala Ile Gly Ala
50 55 60

Tyr Gly Asn Val Pro Ser Ser Val Ser Ala Thr Ala Glu Val Thr Ile
65 70 75 80

Asn Gly Gln Lys Thr Thr Ile Asn Leu Pro Glu Asn Gln Lys Ser Tyr
85 90 95

Ile Tyr Tyr Ala Thr Thr Asn Glu Ser Val Asp Ala Ser Lys Leu Val
100 105 110

Ala Gly Gln Lys Tyr Tyr Thr Gly Ile Asn Asn Ala Ser Leu Asn Leu
115 120 125

Gly Ser Pro Asn His Asp Lys Asp Ile Thr Leu Glu Gly Ser Asn Val
130 135 140

Ser Phe Lys Thr Asn Asp Ser Asp Pro Tyr Thr Lys Thr Leu Lys Val
145 150 155 160

Asn Thr Asp Lys Asn Gly Val Ile Ser Asn Leu Ser Ile Lys Ser Ala
165 170 175

Asn Phe Asp Ala Val Asp Val Asn Asn Ala Arg Thr Val Ser Phe Tyr
180 185 190

Asp Ala Asp Thr Gly Asn Ile Val Thr Ser Gly Ala Leu Glu Ile Asn
195 200 205

Ala Gly Pro Asn Ala Gln Met Asn Val Gln Thr Ile Leu Ala Lys Phe
210 215 220

Glu Gln Lys Tyr Gln Ala Ala Gln Leu Asn Asn Ala Gly Thr Thr Asn
225 230 235 240

Asn Val Ser Tyr Asn Asn Asp Leu Ile Ser Thr Thr Pro Ala Asp Leu
245 250 255

Ala Ala Gln Leu Lys Lys Ala Gly Tyr Ser Val Asp Asn Asn Gly Tyr
260 265 270

Phe Thr Ala Lys His Ser Phe Thr Val Asn Phe Ser Ala Lys Ser Gly
275 280 285

Gln Asn Gly Tyr Thr Thr Thr Met Pro Val Thr Val Thr Val Pro Asn
290 295 300

Val Ala Glu Glu Thr Val Pro Ser Gln Ile Arg Thr Val Met His Asn
305 310 315 320

Ala Phe Phe Tyr Asp Lys Asn Gly Lys Arg Val Gly Ser Asp Lys Val
325 330 335

Thr Arg Tyr Asn Ser Ala Thr Val Ala Met Asn Thr Thr Thr Ile Ile
340 345 350

```
Gly Lys Ala Tyr Tyr Glu Val Ile Glu Asn Gly Lys Ala Thr Gly Lys
        355                 360                 365

Phe Ile Asn Ala Ala Asn Ile Asp Gly Thr Lys Arg Thr Leu Lys His
    370                 375                 380

Asn Ala Tyr Val Tyr Lys Ser Ser Lys Lys Arg Ala Asn Lys Val Val
385                 390                 395                 400

Leu Lys Lys Gly Glu Thr Val Val Thr Tyr Gly Gly Ala Tyr Thr Phe
                405                 410                 415

Lys Asn Gly Lys Gln Tyr Tyr Lys Ile Gly Asn Asn Thr Asp Lys Thr
            420                 425                 430

Tyr Val Lys Val Ala Asn Phe
        435


<210> SEQ ID NO 52
<211> LENGTH: 442
<212> TYPE: PRT
<213> ORGANISM: Artificial Sequence
<220> FEATURE:
<223> OTHER INFORMATION: SlpA protein sequence

<400> SEQUENCE: 52

Met Lys Lys Asn Leu Arg Ile Val Ser Ala Ala Ala Ala Ala Leu Leu
1               5                   10                  15

Ala Val Ala Pro Val Ala Ala Ser Ala Val Ser Val Asn Ala Ala Ser
            20                  25                  30

Ser Ser Ala Val Gln Thr Ala Thr Asn Ile Gly Thr Val Leu Pro Leu
        35                  40                  45

Thr Asp Gly Ser Thr Val Asn Val Lys Pro Asn Ile Ser Leu Asn Thr
    50                  55                  60

Ser Ala Tyr Glu Gly Val Lys Ala Asn Ile Ser Val Ser Phe Ser Ala
65                  70                  75                  80

Thr Val Asp Gly Thr Thr Ala Thr Ser Asn Phe Thr Pro Asn Ala Ser
                85                  90                  95

Thr Ile Glu Leu Trp Lys Asn Glu Lys Asn Lys Val Thr Gln Val Thr
            100                 105                 110

Tyr Leu Gln Gln Val Thr Ser Ser Asn Ala Gly Ala Thr Tyr Gln Val
        115                 120                 125

Lys Met Thr Gln Val Gly Leu Asn Phe Gly Ser Gln Asn Ala Asn Lys
    130                 135                 140

Lys Val Thr Leu Thr Phe Pro Glu Gly Asp Met Phe Lys Thr Ala Asp
145                 150                 155                 160

Thr Ser Leu Ala Gln Ser His Glu Val Lys Leu Asp Gln Asn Gly Thr
                165                 170                 175

Ile Thr Leu Pro Glu Val Val Met Asn Val Thr Ala Lys Asp Phe Ala
            180                 185                 190

Asn Pro Ala Val Val Asn Trp Tyr Asn Thr Ala Thr Asn Ala Val Val
        195                 200                 205

Ser Thr Gly Asn Ile Glu Leu Phe Ala Gly Ser Asp Ala Gly Lys Met
    210                 215                 220

Asn Val Ala Gln Val Val Ser Ala Thr Glu Lys Lys Tyr His Ala Ser
225                 230                 235                 240

Asn Tyr Gly Thr Lys Ala Asn Gln Glu Ser Ser Thr Ile Ser Tyr Thr
                245                 250                 255

Asn Asn Leu Lys Asp Ala Leu Lys Ala Met Asn Val Asp Val Asp Ala
            260                 265                 270
```

```
Gln Gly Trp Phe Val Ala Pro Lys Ser Phe Thr Phe Asn Met Thr Ala
        275                 280                 285

Lys Ala Asn Asn Asn Asp Ala Ser Ser Thr Leu Ala Val Thr Val Ser
    290                 295                 300

Val Pro Asn Gly Lys Asp Met Thr Val Pro Ser Gln Ser Lys Thr Val
305                 310                 315                 320

Met His Asn Ala Phe Phe Tyr Asp Lys Asn Gly Lys Arg Val Gly Ser
                325                 330                 335

Asp Lys Val Thr Arg Tyr Asn Ser Ala Thr Val Ala Met Asn Thr Thr
            340                 345                 350

Thr Ile Asn Gly Lys Ala Tyr Tyr Glu Val Ile Glu Asn Gly Lys Ala
        355                 360                 365

Thr Gly Lys Phe Ile Asn Ala Ala Asn Ile Asp Gly Thr Lys Arg Thr
    370                 375                 380

Leu Lys His Asn Ala Tyr Val Tyr Lys Ser Ser Lys Lys Arg Ala Asn
385                 390                 395                 400

Lys Val Val Leu Lys Lys Gly Thr Glu Val Val Thr Tyr Gly Gly Ala
                405                 410                 415

Tyr Thr Phe Lys Asn Gly Lys Gln Tyr Tyr Lys Ile Gly Asn Asn Thr
            420                 425                 430

Asp Lys Thr Tyr Val Lys Val Ser Asn Phe
        435                 440
```

<210> SEQ ID NO 53
<211> LENGTH: 322
<212> TYPE: PRT
<213> ORGANISM: Artificial Sequence
<220> FEATURE:
<223> OTHER INFORMATION: SlpA protein sequence

<400> SEQUENCE: 53

```
Ser Val Ser Glu Ser Lys Asp Thr Val Asn Val Thr Pro Ser Phe Thr
1               5                   10                  15

Leu Thr Ser Ala Ile Pro Ala Lys Gly Val Pro Ala Thr Leu Gln Gly
            20                  25                  30

Ser Ile Glu Ala Ser Leu Asn Gly Thr Ser Val Thr Ala Asp Val Ala
        35                  40                  45

Asp Val Ala Lys Asp Val Thr Leu Thr Asp Gly Asn Lys Thr Val Tyr
    50                  55                  60

Ser Tyr Asn Glu Arg Glu Asn Lys Val Asp Asn Asn Leu Ser Ala Val
65                  70                  75                  80

Glu Ala Ser Lys Glu Tyr Thr Met Thr Leu Ser Gly Val Gly Phe Ser
                85                  90                  95

Phe Gly Lys Ala Asn Ala Gly Lys Thr Leu Thr Phe Lys Leu Pro Lys
            100                 105                 110

Asn Val Lys Val Asn Asp Thr Ser Asn Asp Val Lys Val Ser Leu Asp
        115                 120                 125

Gln Tyr Gly Asn Ala Thr Asn Leu Lys Phe Val Ile Ser Asn Ile Lys
    130                 135                 140

Ala Tyr Asp Ser Ala Asn Thr Asn Ala Val Ser Phe Tyr Ala Ala Lys
145                 150                 155                 160

Ser Gly Leu Val Ala Thr Gln Gly Ser Tyr Met Thr Leu Ala Asp Glu
                165                 170                 175

Asn Gly Asn Leu Asn Val Asn Thr Leu Leu Asp Lys Leu Lys Gly Lys
            180                 185                 190
```

Tyr Glu Ala Met Gln Phe Lys Asp Ser Lys Phe Glu Thr Val Asn Val
195 200 205

Asn Thr Thr Ala Asp Asp Val Lys Ala Glu Leu Glu Lys Ala Gly Ile
210 215 220

Lys Val Asp Ala Ala Asn Asn Phe Glu Ala Pro Asp Thr Phe Thr Val
225 230 235 240

Thr Leu Asn Ala Lys Ser Asp Val Asn Gly Lys Thr Ala Ser Leu Pro
245 250 255

Val Val Val Thr Val Pro Asn Gly Lys Ser Thr Val Val Pro Ser Gln
260 265 270

Ser Lys Thr Ile Met His Asn Ala Tyr Tyr Tyr Asp Lys Asp Ala Lys
275 280 285

Arg Val Gly Thr Asp Lys Val Thr Arg Tyr Asn Ala Val Thr Val Ala
290 295 300

Met Asn Thr Thr Lys Leu Ala Asn Gly Ile Ser Tyr Tyr Glu Val Ile
305 310 315 320

Glu Asn

<210> SEQ ID NO 54
<211> LENGTH: 330
<212> TYPE: PRT
<213> ORGANISM: Artificial Sequence
<220> FEATURE:
<223> OTHER INFORMATION: SlpA protein sequence

<400> SEQUENCE: 54

Ala Asp Ser Ala Ile Asn Ala Asn Thr Asn Ala Lys Tyr Asp Val Asp
1 5 10 15

Val Thr Pro Ser Ile Ser Ala Ile Ala Ala Val Ala Lys Ser Asp Thr
20 25 30

Met Pro Ala Ile Pro Gly Ser Leu Thr Gly Ser Ile Ser Ala Ser Tyr
35 40 45

Asn Gly Lys Ser Tyr Thr Ala Asn Leu Pro Lys Asp Ser Gly Asn Ala
50 55 60

Thr Ile Thr Asp Ser Asn Asn Asn Thr Val Lys Pro Ala Lys Leu Glu
65 70 75 80

Ala Asp Lys Ala Tyr Thr Val Thr Val Pro Asp Val Ser Phe Asn Phe
85 90 95

Gly Ser Glu Asn Ala Gly Lys Val Ile Thr Ile Gly Ser Ala Asn Pro
100 105 110

Asn Val Thr Phe Thr Lys Lys Thr Gly Asp Gln Pro Ala Ser Thr Val
115 120 125

Lys Val Thr Leu Asp Gln Asp Gly Val Ala Lys Leu Ser Ser Val Gln
130 135 140

Ile Lys Asn Val Tyr Ala Ile Asp Thr Thr Tyr Asn Ser Asn Val Asn
145 150 155 160

Phe Tyr Asp Val Thr Thr Gly Ala Ile Val Thr Thr Gly Ala Val Ser
165 170 175

Ile Asp Ala Asp Asn Gln Gly Gln Leu Asn Ile Thr Ser Val Val Ala
180 185 190

Ala Ile Asn Ser Lys Tyr Phe Ala Ala Gln Tyr Asp Lys Lys Gln Leu
195 200 205

Thr Asn Asp Val Thr Phe Asp Thr Glu Thr Ala Val Lys Asp Ala Leu
210 215 220

```
Lys Ala Gln Lys Ile Glu Val Ser Ser Val Gly Tyr Phe Lys Ala Pro
225                 230                 235                 240

His Thr Phe Thr Val Asn Val Lys Ala Thr Ser Asn Lys Asn Gly Lys
                245                 250                 255

Ser Ala Thr Leu Pro Val Thr Val Thr Val Pro Asn Val Ala Asp Pro
            260                 265                 270

Val Val Pro Ser Gln Ser Lys Thr Ile Met His Asn Ala Tyr Phe Tyr
        275                 280                 285

Asp Lys Asp Ala Lys Arg Val Gly Thr Asp Lys Val Thr Arg Tyr Asn
    290                 295                 300

Thr Val Thr Val Ala Met Asn Thr Thr Lys Leu Ala Asn Gly Ile Ser
305                 310                 315                 320

Tyr Tyr Glu Val Ile Glu Asn Gly Lys Ala
                325                 330


<210> SEQ ID NO 55
<211> LENGTH: 475
<212> TYPE: PRT
<213> ORGANISM: Artificial Sequence
<220> FEATURE:
<223> OTHER INFORMATION: SlpA protein sequence

<400> SEQUENCE: 55

Met Asp His Val Ser Lys Gly Phe Val His Tyr Arg Leu Leu Ser His
1               5                   10                  15

Ala Glu Pro Met Ala Tyr Tyr Ile Phe Tyr Ile Ser Arg Arg Lys Asp
            20                  25                  30

His Met Lys Lys Asn Leu Arg Ile Val Ser Ala Ala Ala Ala Ala Leu
        35                  40                  45

Leu Ala Val Ala Pro Val Ala Ala Thr Ala Met Pro Val Asn Ala Ala
    50                  55                  60

Thr Thr Ile Asn Ala Asp Ser Ala Ile Asn Ala Asn Thr Asn Ala Lys
65                  70                  75                  80

Tyr Asp Val Asp Val Thr Pro Ser Ile Ser Ala Ile Ala Lys Val Thr
                85                  90                  95

Gly Ser Ala Thr Ile Pro Gly Ser Leu Thr Gly Ser Ile Ser Ala Ser
            100                 105                 110

Tyr Asn Gly Lys Ser Tyr Thr Ala Asn Leu Pro Lys Asp Ser Gly Asn
        115                 120                 125

Ala Thr Ile Ala Asp Lys His Gly Asn Pro Val Lys Pro Ala Asp Leu
    130                 135                 140

Glu Ala Asp Lys Ala Tyr Thr Val Thr Val Pro Asp Val Ser Phe Asn
145                 150                 155                 160

Phe Gly Ser Glu Asn Ala Gly Lys Glu Ile Thr Ile Gly Ser Ala Asn
                165                 170                 175

Gln Asn Val Thr Phe Thr Thr Lys Asp Ser Gln Ser Gly Ser Thr Val
            180                 185                 190

Ser Gly Ser Thr Val Lys Val Thr Leu Asp Gln Asp Gly Val Ala Lys
        195                 200                 205

Leu Ser Ser Val Gln Ile Lys Asp Val Tyr Ala Ile Asp Thr Thr Tyr
    210                 215                 220

Asn Ser Asn Val Asn Phe Tyr Asp Val Thr Thr Gly Ala Ile Val Thr
225                 230                 235                 240

Thr Gly Ala Val Ser Ile Asp Ala Asp Asn Gln Gly Gln Leu Asn Thr
                245                 250                 255
```

```
Ala Ser Val Val Ala Ala Ile Ser Ser Lys Tyr Phe Ala Ala Gln Tyr
            260                 265                 270

Ala Asp Lys Asn Leu Thr Ser Asp Asn Val Thr Tyr Asn Ile Glu Thr
        275                 280                 285

Ala Val Lys Asp Ala Leu Lys Ala Gln Lys Ile Glu Val Ser Ser Val
    290                 295                 300

Gly Tyr Phe Lys Ala Pro His Thr Phe Thr Val Asn Val Lys Ala Thr
305                 310                 315                 320

Ser Asn Lys Asn Gly Lys Ser Ala Thr Leu Pro Val Thr Val Thr Val
                325                 330                 335

Pro Asn Val Ala Asp Pro Val Val Pro Ser Gln Ser Lys Thr Ile Met
            340                 345                 350

His Asn Ala Tyr Phe Tyr Asp Lys Asp Ala Lys Arg Val Gly Thr Asp
        355                 360                 365

Lys Val Thr Arg Tyr Asn Thr Val Thr Val Ala Met Asn Thr Thr Lys
    370                 375                 380

Leu Ala Asn Gly Ile Ser Tyr Tyr Glu Val Ile Glu Asn Gly Lys Ala
385                 390                 395                 400

Thr Gly Lys Tyr Ile Asn Ala Asp Asn Ile Asp Gly Thr Lys Arg Thr
                405                 410                 415

Leu Lys His Asn Ala Tyr Val Tyr Lys Thr Ser Lys Lys Arg Ala Asn
            420                 425                 430

Lys Val Val Leu Lys Lys Gly Thr Glu Val Thr Thr Tyr Gly Gly Ser
        435                 440                 445

Tyr Lys Phe Lys Asn Gly Lys Lys Tyr Tyr Lys Ile Gly Ala Asp Thr
    450                 455                 460

Lys Lys Thr Tyr Val Arg Val Glu Asn Phe Asp
465                 470                 475


<210> SEQ ID NO 56
<211> LENGTH: 467
<212> TYPE: PRT
<213> ORGANISM: Lactobacillus acidophilus

<400> SEQUENCE: 56

Met Lys Lys Asn Leu Arg Ile Val Ser Ala Ala Ala Ala Ala Leu Leu
1               5                   10                  15

Ala Val Ala Pro Val Ala Ala Ser Ala Val Ser Thr Val Ser Ala Ala
            20                  25                  30

Asp Ala Thr Thr Thr Thr Thr Ala Thr Thr Thr Thr Asn Lys Pro Thr
        35                  40                  45

Val Asp Leu Thr Gly Ala Gly Ala Val Thr Asn Ala Ala Lys Thr Val
    50                  55                  60

Thr Val Thr Pro Asn Phe Thr Leu Thr Ala Ala Ile Ala Lys Asp Gly
65                  70                  75                  80

Lys Val Thr Ala Ser Ala Thr Leu Gln Gly Thr Ile Thr Ala Ser Leu
                85                  90                  95

Asn Gly Thr Ser Val Thr Ala Asn Val Ile Asp Ala Ala Lys Gly Ile
            100                 105                 110

Thr Leu Lys Ser Asn Ser Gly Tyr Thr Thr Ile Tyr Lys Tyr Asp Ala
        115                 120                 125

Asn Thr Asn Thr Thr Glu Asn Asn Leu Gly Lys Trp Asn Glu Lys Thr
    130                 135                 140

Asn Asp Val Tyr Val Lys Ala Gly Asn Asp Tyr Gln Val Glu Leu Thr
145                 150                 155                 160
```

-continued

```
Gly Val Gly Phe Ser Phe Gly Ser Ala Asn Ala Asn Lys Glu Val Ser
                165                 170                 175

Leu Lys Leu Pro Ser Asn Val Thr Val Lys Gly Val Lys Asp Asn Lys
            180                 185                 190

Val Thr Leu Asp Gln Tyr Gly Asn Val Thr Asn Leu Thr Phe Ile Val
        195                 200                 205

Lys Asp Ile Lys Ala Tyr Asp Ala Thr Asn Thr Ser Ala Val Gln Phe
    210                 215                 220

Tyr Asn Thr Asn Ser Gly Leu Ile Glu Ser Lys Ala Thr Tyr Met Ala
225                 230                 235                 240

Leu Ala Asp Asn Asn Gly Asn Leu Asn Val Asn Thr Leu Leu Asn Gly
                245                 250                 255

Leu Asn Lys Gln Tyr Lys Ala Val Gln Leu Gln Asn Gly Glu Leu Lys
            260                 265                 270

Asp Val Thr Val Thr Thr Thr Ala Ala Asp Leu Thr Ala Glu Leu Thr
        275                 280                 285

Lys Ala Gly Ile Lys Val Asn Ala Ala Gly Asp Phe Glu Ala Pro Ala
    290                 295                 300

Ser Phe Thr Ala Thr Leu Thr Ala Lys Ser Glu Val Asn Gly Lys Val
305                 310                 315                 320

Ala Thr Leu Pro Val Thr Val Thr Val Pro Asn Gly Lys Val Thr Thr
                325                 330                 335

Val Asp Ser Val Ser Lys Arg Ile Met His Asn Ala Tyr Phe Tyr Asp
            340                 345                 350

Lys Asp Ala Lys Arg Val Gly Thr Asp Ser Val Lys Arg Tyr Ala Ser
        355                 360                 365

Val Ser Val Leu Pro Asn Thr Thr Thr Ile Asn Gly Lys Ala Tyr Tyr
    370                 375                 380

Gln Val Val Glu Asn Gly Lys Ala Val Asp Lys Tyr Ile Asn Ala Ala
385                 390                 395                 400

Asn Ile Asp Gly Thr Lys Arg Thr Leu Lys His Asn Ala Tyr Val Tyr
                405                 410                 415

Ala Ser Ser Lys Lys Arg Ala Asn Lys Val Val Leu Lys Lys Gly Glu
            420                 425                 430

Val Val Thr Thr Tyr Gly Ala Ser Tyr Thr Phe Lys Asn Gly Gln Lys
        435                 440                 445

Tyr Tyr Lys Ile Gly Asn Asn Thr Asp Lys Thr Tyr Val Lys Val Ala
    450                 455                 460

Asn Phe Arg
465
```